US012774484B2

(12) United States Patent
Virdee et al.

(10) Patent No.: US 12,774,484 B2
(45) Date of Patent: Oct. 27, 2026

(54) LIGASE SCREENING ASSAY

(71) Applicant: UNIVERSITY OF DUNDEE, Dundee (GB)

(72) Inventors: Satpal Virdee, Dundee (GB); Kuan-Chuan Pao, Douliu City (TW)

(73) Assignee: UNIVERSITY OF DUNDEE, Dundee (GB)

( * ) Notice: Subject to any disclaimer, the term of this patent is extended or adjusted under 35 U.S.C. 154(b) by 638 days.

(21) Appl. No.: 16/981,607

(22) PCT Filed: Mar. 18, 2019

(86) PCT No.: PCT/GB2019/050751

§ 371 (c)(1),
(2) Date: Sep. 16, 2020

(87) PCT Pub. No.: WO2019/175609

PCT Pub. Date: Sep. 19, 2019

(65) Prior Publication Data

US 2021/0017569 A1 Jan. 21, 2021

(30) Foreign Application Priority Data

Mar. 16, 2018 (GB) ...................................... 1804285

(51) Int. Cl.
*C12Q 1/48* (2006.01)

(52) U.S. Cl.
CPC ....... *C12Q 1/48* (2013.01); *G01N 2333/9108* (2013.01); *G01N 2500/02* (2013.01)

(58) Field of Classification Search
None
See application file for complete search history.

(56) References Cited

U.S. PATENT DOCUMENTS

| | | |
|---|---|---|
| 2006/0040335 A1 | 2/2006 | Butt et al. |
| 2010/0173024 A1 | 7/2010 | Mcdaniel |

FOREIGN PATENT DOCUMENTS

| | | | |
|---|---|---|---|
| CN | 1989411 A | | 6/2007 |
| CN | 102300578 A | | 12/2011 |
| WO | 2016/051174 | | 4/2016 |
| WO | 2016/070129 A1 | | 5/2016 |

OTHER PUBLICATIONS

Yi, J.J., et al. 2007 Pharmacol Rev 59(1): 14-39. (Year: 2007).*
Bachovchin, D.A., et al. 2009 Nature Biotechnology 27(4): 387-785. (Year: 2009).*
Babetto et al., The Phr1 Ubiquitin Ligase Promotes Injury-Induced Axon Self Destruction, Cell Reports, 2013, pp. 1422-1429, vol. 3.
Conforti et al., Wallerian degeneration: an emerging axon death pathway linking injury and disease, Nature Reviews Neuroscience, 2014, pp. 394-409, vol. 15.
Dorr et al., MYCBP2 is a Guanosine Exchange Factor for Ran Protein and Determines its Localization in Neurons of Dorsal Root Ganglia, Journal of Biochemistry, 2015, pp. 25620-25635, vol. 290, No. 42.
Dove et al., Molecular insights into RBR E3 ligase ubiquitin transfer mechanisms, EMBO Reports, 2016, pp. 1221-1235, vol. 17.
Kuan-Chuan et al., Activity-based E3 ligase profiling uncovers an E3 ligase with esterification activity, Nature, 2018, pp. 381-385, vol. 556.
Maeurer et al., Sphingosine-1-phosphate induced mTOR-activation is mediated by the E3-ubiquitin ligase PAM, Cellular Signaling, 2009, pp. 293-300, vol. 21.
Xiong et al., The Highwire Ubiquitin Ligase Promotes Axonal Degeneration by Tuning Levels of Nmnat Protein, PLOS Biology, 2012, p. e1001440, vol. 10.
Written Opinion of the International Searching Authority, in PCT application No. PCT/GB2019/050751, filed on Mar. 18, 2019, 7 pages.
Search Report, filed in application No. GB1804285.3, filed on Dec. 3, 2018, 5 pages.
International Preliminary Report on Patentability received for PCT Patent Application No. PCT/GB2019/050751, mailed on Oct. 1, 2020, 9 pages.
International Search Report and Written Opinion received for PCT Patent Application No. PCT/GB2019/050751, mailed on May 16, 2019, 11 pages.
Office Action received for Chinese Patent Application No. 201980032515.0, mailed on Dec. 26, 2023, 12 pages (5 pages of English Translation and 7 pages of Original Document).
Pao, et al.; "Activity-based E3 ligase profiling uncovers an E3 ligase with esterification activity." Nature 556(7701):381-385, 2018. https://link.edgepilot.com/s/6949bb43/9pzVw0-ASkiVuQRvKPoRpw?u=https://www.ebi.ac.uk/ena/browser/api/embl/AAC39928.1?lineLimit=1000, obtained from the internet Mar. 27, 2024.
"LUBAC synthesizes linear ubiquitin chains via a thioester intermediate", EMBO, vol. 13, No. 9, 2012, 7 pages.
Ali, Y. O., et al., "Screening with an NMNAT2-MSD platform identifies small molecules that modulate NMNAT2 levels in cortical neurons", Sci. Rep., Mar. 7, 2017,13 pages.
Alpi, A. F., et al., "Mechanism and disease association of E2-conjugating enzymes: lessons from UBE2T and UBE2L3", Biochem. J., vol. 473, 2016, pp. 3401-3419.

(Continued)

*Primary Examiner* — Marsha Tsay
(74) *Attorney, Agent, or Firm* — Wolter Van Dyke Davis, PLLC; Eugene J. Molinelli; Martha Cassidy

(57) ABSTRACT

The present invention relates to a method for identifying a MYCBP2 modulator. Suitable modulators are identified by modulation of MYCBP2 ubiquitin E3 ligase activity via covalent modification of either of two catalytic cysteines (C4520 and C4572) or by impeding the motion of a newly presented dynamic, so-called, mediator loop region where C4520 resides. The present invention also relates to the use of hydroxy group-containing small molecules and peptides as proxy substrates for measuring MYCBP2 ligase activity and their use in the method of identifying modulators.

13 Claims, 26 Drawing Sheets

Specification includes a Sequence Listing.

(56) References Cited

OTHER PUBLICATIONS

Borodovsky, A., et al., "Chemistry-Based Functional Proteomics Reveals Novel Members of the Deubiquitinating Enzyme Family", Chemistry & Biology, vol. 9, Oct. 2002, pp. 1149-1159.
Brownell, J. E., et al., "Substrate-Assisted Inhibition of Ubiquitin-like Protein-Activating Enzymes: The NEDD8 E1 Inhibitor MLN4924 Forms a NEDD8-AMP Mimetic In Situ", Molecular Cell, vol. 37, Jan. 15, 2010, pp. 102-111.
Byrne R., et al., "Activity-Based Probes for Hect E3 Ubiquitin Ligases", Chem. Bio. Chem., vol. 18, 2017, pp. 1415-1427.
Cadwell, et al., "Ubiquitination on Nonlysine Residues by a Viral E3 Ubiquitin Ligase", Science, vol. 309, Jul. 1, 2005, pp. 127-130.
Chen, B., et al., "Dynamic Imaging of Genomic Loci in Living Human Cells by an Optimized CRISPR/Cas System", Cell., vol. 155, No. 7, Dec. 19, 2013, pp. 1479-1491.
Cho, S. W., et al., "Analysis of off-target effects of CRISPR/Cas-derived RNA-guided endonucleases and nickases", Genome Res, vol. 24, 2014, pp. 132-141.
Davis, et al., "Homology-directed repair of DNA nicks via pathways distinct from canonical double-strand break repair", PNAS, Feb. 20, 2014, pp. E924-E932.
Deshaies, R. J., et al., "Ring Domain E3 Ubizuitin Ligases", Annu. Rev. Biochem., vol. 78, 2009, pp. 399-434.
Dou, H., et al., "Structure of BIRC7-E2 ubiquitin conjugate reveals the mechanism of ubiquitin transfer by a Ring dimer", Nat Struct Mol Biol., vol. 19, No. 9, Sep. 2012, 21 pages.
Dove, K. K., et al., "Structural Studies of HHARI/UbcH7~Ub Reveal Unique E2~Ub Conformational Restriction by RBR Ring1", Structure, vol. 25, 2017, pp. 890-900.
Emsley, P., et al., "Features and development of Coot", Biological Crystallography, vol. D66, 2010, pp. 486-501.
Feng, Z., et al., "Efficient genome editing in plants using a CRISPR/Cas system", Cell Research, vol. 23, Aug. 20, 2013, pp. 1229-1232.
Fu, Y., et al., "High-frequency off-target mutagenesis induced by CRISPR-Cas nucleases in human cells", Nature Biotechnology, vol. 31, No. 9, Sep. 2013, pp. 823-827.
Fu, Y., et al., "Improving CRISPR-Cas nuclease specificity using truncated guide RNAs", Nature Biotechnology, vol. 32, No. 3, Mar. 2013, 9 pages.
Gasiunas, G., et al., "Cas9-crRNA ribonucleoprotein complex mediates specific DNA cleavage for adaptive immunity in bacteria", PNAS, Sep. 4, 2012, pp. E2579-2586.
Gilbert, L. A., et al., "CRISPR-Mediated Modular RNA-Guided Regulation of Transcription in Eukaryotes", Cell., vol. 154, No. 2, Jul. 18, 2013, pp. 442-451.
Gong, C., et al., "Mechanism of nonhomologous end-joining in mycobacteria: a low-fidelity repair system driven by Ku, ligase D and ligase C", Nature Structural & Molecular Biology, Mar. 20, 2005, 9 pages.
Grill, B., et al., "The PHR proteins: intracellular signaling hubs in neuronal development and axondegeneration", Neural Development, vol. 11, No. 8, 2016, pp. 1-18.
Hershko, A., et al., "The Ubiquitin System", Annu. Rev. Biochem., vol. 67, 1998, pp. 425-479.
Hewings, D. S., et al., "Activity-based probes for the ubiquitin conjugation-deconjugation machinery: new chemistries, new tools, and new insights", The FEBS Journal, vol. 284, 2017, pp. 1555-1576.
Hsu, P. D., et al., "DNA targeting specificity of RNA-guided Cas9 nucleases", Nature Biotechnology, vol. 31, No. 9, Sep. 2013, 8 pages.
Hu, J., et al., "Direct activation of human and mouse Oct4 genes using engineered TALE and Cas9 transcription factors", Nucleic Acids Research, vol. No. 7, 2014, pp. 4375-4390.
Huibregtse, J. M., et al., "A family of proteins structurally and functionally related to the E6-AP ubiquitin-protein ligase", Proc. Natl. Acad. Sci., vol. 92, Mar. 1995, pp. 2563-2567.
Hwang, W. Y., et al., ""Heritable and precise zebrafish genome editing using a CRISPR-Cas system"", PLoS One, vol. 8, No. 7, 2013, e68708.
Jinek, M., et al., "A Programmable Dual-RNA-Guided DNA Endonuclease in Adaptive Bacterial Immunity", Science, vol. 337, No. 6096, Jun. 28, 2012, pp. 816-821.
Kimple, M. E., et al., "Affinity Tag for Protein Purification and Detection Based on the Disulfide-Linked Complex of InaD and NorpA", BioTechniques, vol. 33, No. 2, 2002, 2002, 9 pages.
Kuan-Chuan, P., et al., "Probes of Ubiquitin E3 ligases distinguish different stages of Parkin activation", Nat Chem Biol., vol. 12, No. 5, May 2016, pp. 324-331.
Langer, G., et al., "Automated macromolecular model building for X-ray crystallography using ARP/wARP version 7", Nature Protocols, vol. 3, 2008, pp. 1171-1179.
Lechtenberg, B. C., et al., "Structure of a HOIP/E2~ubiquitin complex reveals RBR E3 ligase mechanism and regulation", Nature, 529, 2016, pp. 546-550.
Lovell, S. C., et al., "Structure validation by Ca geometry: ?,? and Cß deviation", Proteins, Jan. 8, 2003, 14 pages.
Maeder, M. L., et al., "CRISPR RNA-guided activation of endogenous human genes", Nat Methods., vol. 10, No. 10, Oct. 2013, pp. 977-979.
Maeder, M. L., et al., "Rapid "open-source" engineering of customized zinc-finger nucleases for highly efficient gene modification", Mol Cell, vol. 31, No. 2, Jul. 25, 2008, pp. 294-301.
Mali, P., "RNA-Guided Human Genome Engineering via Cas9", Science, vol. 339, No. 6121, Feb. 2013, 8 pages.
Milde, S., et al., "Subcellular Localization Determines the Stability and Axon Protective Capacity of Axon Survival Factor Nmnat2", Plos Biology, Apr. 16, 2013, 19 pages.
Miller, J. C., et al., "A TALE nuclease architecture for efficient genome editing", Nature Biotechnology, vol. 29, 2011, pp. 143-148.
Murshudov, G. N., "REFMAC5 for the refinement of macromolecular crystal structures", Acta Cryst., vol. D67, 2011, pp. 355-367.
Mussolino, C., et al., "A novel TALE nuclease scaffold enables high genome editing activity in combination with low toxicity", Nucleic Acids Research, vol. 39, No. 21, Nov. 1, 2011, pp. 9283-9293.
Niphakis, M. J., et al., "Enzyme Inhibitor Discovery by Activity-Based Protein Profiling", Annual Review of Biochemistry, vol. 83, 2014, pp. 341-377.
Olsen, K. S., et al., "Structure of a ubiquitin E1-E2 complex: insights to E1-E2 thioester transfer", Mol Cell., vol. 49, No. 5, Mar. 7, 2013, pp. 884-896.
Overballe-Petersen, S., et al.,"Bacterial natural transformation by highly fragmented and damaged DNA", Biological Sciences, vol. 110, No. 49, Dec. 3, 2013, pp. 19860-19865.
Perez-Pinera, P., et al., "Synergistic and tunable human gene activation by combinations of synthetic transcription factors", Nature Methods, vol. 10, No. 3, Mar. 2013, pp. 239-242.
Plechanovova, A., et al., "Structure of a Ring E3 ligase and ubiquitin-loaded E2 primed for catalysis", Nature, vol. 489, 2012, pp. 115-120.
Pruneda, N. J., et al., "Structure of an E3:E2~Ub complex reveals an allosteric mechanism shared among Ring/U-box ligases", Mol Cell., vol. 47, No. 6, Sep. 28, 2012, pp. 933-942.
Qi, L. S., et al., "Repurposing CRISPR as an RNA-Guided Platform for Sequence-Specific Control of Gene Expression", Cell., vol. 152, No. 5, Feb. 28, 2013 pp. 1173-1183.
Ran, F. A., "Double nicking by RNA-guided CRISPR Cas9 for enhanced genome editing specificity", Cell, vol. 154, No. 6, Sep. 12, 2013, 19 pages.
Sander, J. D., et al., "ZiFiT (Zinc Finger Targeter): an updated zinc finger engineering tool", Nucleic Acids Research, vol. 38, Apr. 30, 2010, pp. W462-W468.
Sander, J. D., et al., "Zinc Finger Targeter (ZiFiT): an engineered zinc finger/target site design tool", Nucleic Acids Research, vol. 35, No. 2, Jul. 2007, pp. W599-W605.
Scheffner, M., et al., "Protein ubiquitination involving an E1-E2-E3 enzyme ubiquitin thioester cascade", Nature, vol. 373, Jan. 1995, pp. 81.83.

(56) References Cited

OTHER PUBLICATIONS

Shimizu, Y., et al., "Ubiquitylation of an ERAD substrate occurs on multiple types of amino acids", Mol Cell., vol. 40, No. 6, Dec. 22, 2010, 19 pages.
Stanley, M., et al., "Orthogonal Thiol Functionalization at a Single Atomic Center for Profiling Transthiolation Activity of E1 Activating Enzymes", American Chemical Society, 2015, 13 pages.
Stieglitz, B., et al., "Structural basis for ligase-specific conjugation of linear ubiquitin chains by HOIP", Nature, vol. 503, Nov. 21, 2013, 17 pages.
Wan, H. I., et al., "Highwire Regulates Synaptic Growth in *Drosophila*", Neuron, vol. 26, May 2000, pp. 313-329.
Wang, X., et al., "Ubiquitination of Substrates by Esterification", Traffic, vol. 13, 2012, pp. 19-24.
Wenzel, D. M., et al., "UbcH7 reactivity profile reveals Parkin and HHARI to be Ring/Hect hybrids", Nature, vol. 474, No. 7349, Jun. 2, 2011, pp. 105-108.
Wu, P. Y., et al., "A conserved catalytic residue in the ubiquitin-conjugating enzyme family", The EMBO Journal, vol. 22, No. 19, 2003, pp. 5241-5250.
Yang, B., et al., "Identification of cross-linked peptides from complex samples", Nature Methods, vol. 9, Jul. 8, 2012, 6 pages.
You, J., et al., "A Hect Domain E3 Enzyme Assembles Novel Polyubiquitin Chains", The Journal of Biological Chemistry, vol. 276, No. 23, Jun. 8, 2001, pp. 19871-19878.
Yunus, A. A., et al., "Lysine activation and functional analysis of E2-mediated conjugation in the SUMO pathway", Nature Structural & Molecular Biology, vol. 13, 2006, pp. 491-499.
Zhen, M., et al., "Regulation of Presynaptic Terminal Organization by C. elegans RPM-1, a Putative Guanine Nucleotide Exchanger with a Ring-H2 Finger Domain", Neuron, vol. 26, May 2000, pp. 331-343.
Zheng, N., et al., "Structure of a c-Cbl-UbcH7 Complex: Ring Domain Function in Ubiquitin-Protein Ligases", Cell, vol. 102, Aug. 18, 2000, pp. 533-539.
Zhou, J., et al., "Dual sgRNAs facilitate CRISPR/Cas9-mediated mouse genome targeting", The Febs Journal, Feb. 3, 2014, 9 pages.

* cited by examiner

| | + | ++ | +++ |
|---|---|---|---|
| b1 | 114.0913 | 57.5493 | 38.702 |
| b2 | 277.1547 | 139.081 | 93.0564 |
| b3 | 414.2136 | 207.6104 | 138.7427 |
| b5 | 625.3083 | 313.1583 | 209.1079 |
| b6 | 739.3933 | 369.7003 | 246.8026 |
| b7 | 852.4363 | 426.7218 | 284.8169 |
| b8 | 939.4683 | 470.2378 | 313.8276 |
| b9 | 1053.5112 | 527.2592 | 351.8419 |
| b10 | 1110.5327 | 555.77 | 370.8491 |
| b11 | 1197.5647 | 599.286 | 399.8598 |
| b12 | 1310.6488 | 655.828 | 437.5544 |
| b17 | 2894.4037 | 1447.7055 | 965.4727 |
| B3 | 2637.3025 | 1319.1549 | 879.7723 |
| B4 | 2766.3451 | 1383.6762 | 922.7865 |
| B6 | 2894.4037 | 1447.7055 | 965.4727 |
| y1 | 175.119 | 88.0631 | 59.0445 |
| y2 | 288.2030 | 144.6051 | 96.7392 |
| y3 | 401.2871 | 201.1472 | 134.4339 |
| y4 | 516.3140 | 258.6606 | 172.7762 |
| y5 | 629.3981 | 315.2027 | 210.4709 |
| y6 | 1756.8738 | 879.9406 | 586.9628 |
| y7 | 1871.9579 | 936.4826 | 624.6575 |
| y8 | 1958.9899 | 979.9986 | 653.6682 |
| y9 | 2016.0114 | 1008.5093 | 672.6753 |
| y10 | 2130.0543 | 1065.5308 | 710.6896 |
| y11 | 2217.0863 | 1109.0468 | 739.7003 |
| y12 | 2331.1283 | 1166.0683 | 777.7146 |
| y13 | 2444.2133 | 1222.6103 | 815.4093 |
| y14 | 2558.2563 | 1279.6318 | 853.4238 |
| y15 | 2655.3090 | 1328.1582 | 885.7745 |
| y16 | 2792.3679 | 1396.6876 | 931.4608 |
| Y1 | 175.1190 | 88.0631 | 59.0445 |
| Y2 | 232.1404 | 116.5738 | 78.0517 |
| Y3 | 303.1775 | 152.0924 | 101.7307 |
| Y4 | 432.2201 | 216.6137 | 144.7449 |
| Y5 | 503.2572 | 252.1322 | 168.4239 |
| Y6 | 618.2842 | 309.6457 | 206.7662 |

Tris(hydroxymethyl)aminomethane

Glycerol

FIG. 15

| | $MYCBP2_{4378-4640}$ |
|---|---|
| Data collection | |
| Space group | $P 6_1$ |
| Cell dimensions | |
| a, b, c (Å) | 82.58, 82.58, 103.30 |
| α, γ, β (°) | 90.00, 90.00, 120.00 |
| Resolution (Å) | 40-1.75 (1.78-1.75) |
| $R_{merge}$ | 0.051 (0.404) |
| I / σI | 18.3 (2.4) |
| Completeness (%) | 99.3 (93.3) |
| Redundancy | 6.9 (3.0) |
| | |
| Refinement | |
| Resolution (Å) | 40.0–1.75 |
| No. reflections | 40007 |
| $R_{work}$ / $R_{free}$ | 0.172/0.196 |
| No. atoms | |
| Protein | 1988 |
| Ligand/ion | 6 |
| Water | 257 |
| B-factors | |
| Protein | 28.2 |
| Ligand/ion | 26.6 |
| Water | 35.5 |
| R.m.s. deviations | |
| Bond lengths (Å) | 0.019 |
| Bond angles (°) | 1.9 |

Values in parentheses are for highest-resolution shell.

LIGASE SCREENING ASSAY

CROSS-REFERENCE TO RELATED APPLICATIONS

This application is a 371 U.S. national phase application which claims the benefit International PCT application No. PCT/GB2019/050751, filed 18 Mar. 2019, which claims priority from United Kingdom application No. 1804285.3, filed 16 Mar. 2018. The entire contents of these applications are hereby incorporated by reference as if fully set forth herein.

REFERENCE TO SEQUENCE LISTING SUBMITTED VIA EFS-WEB

This application includes an electronically submitted sequence listing in .txt format. The .txt file contains a sequence listing entitled "SequenceListingPE959024_ST25" created on Sep. 16, 2020 and is 163 KB in size. The sequence listing contained in this .txt file is part of the specification and is hereby incorporated by reference herein in its entirety.

FIELD OF THE INVENTION

The present invention relates to a method for identifying a MYCBP2 modulator. Suitable modulators are identified by modulation of MYCBP2 ubiquitin E3 ligase activity via covalent modification of either of two catalytic cysteines (C4520 and C4572) or by impeding the motion of a newly presented dynamic, so-called, mediator loop region where C4520 resides. The present invention also relates to the use of hydroxy group-containing small molecules and peptides as proxy substrates for measuring MYCBP2 ligase activity and their use in the method of identifying modulators.

BACKGROUND

Protein modification with ubiquitin (Ub) and ubiquitin-like modifiers (Ubls) regulates most aspects of eukaryotic biology. Ub/Ubl conjugation is carried out by an enzymatic cascade consisting of E1 activating (E1), E2 conjugating (E2) and E3 ligating (E3) enzymes. Conjugation requires an initial ATP-dependent thioesterification step and up to two subsequent transthioesterification steps via the juxtaposition of catalytic cysteines in E1s, E2s and E3s. Ubiquitination is typically considered a posttranslational modification of lysine residues.

Homologous to E6-AP Carboxy Terminus (HECT) E3s undergo a catalytic cysteine-dependent transthiolation reaction with the E2-ubiquitin covalently linked intermediate to form a covalently linked E3-ubiquitin intermediate. Additionally, RING-between-RING (RBR) E3s have a canonical RING domain that is linked to an ancillary domain. This contains a catalytic cysteine enabling a hybrid RING/HECT mechanism.

The ubiquitin conjugation enzymatic cascade has been implicated in a broad spectrum of diseases. Although numerous different E2 and E3 enzymes and classes have been identified, little is known about some of these enzymes. There therefore remains a need to profile, or further profile the activity of these enzymes.

The present invention has been devised with these issues in mind.

SUMMARY OF THE INVENTION

The present invention is based on studies by the inventors into the mechanism of action of the E3 ubiquitin ligase MYCBP2. The inventors have surprisingly found that this ligase exhibits esterification activity towards, for example, hydroxy containing substrates. The inventors also believe that transthiolation occurs between E2 conjugating enzyme (E2) and a cysteine residue within MYCBP2. This leads to the intramolecular relay of ubiquitin from the cysteine residue to a further cysteine residue within MYCBP2 and then to its substrate.

Based upon the identification of the mechanism of action, the interaction of the active MYCBP2 protein with a substrate, whether artificial or endogenous, can be studied. This interaction can advantageously be exploited to screen test substances for their effect upon this interaction. It is therefore an object of the present invention to provide a screening assay based upon this interaction. It is a further object of the present invention to identify and/or provide modulators of MYCBP2 for use in therapy and/or prophylaxis, for example in the therapy and/or prophylaxis of axon degeneration-associated injury and disorder.

It will be appreciated that any of the features described herein (including any accompanying claims and drawings), may be combined with any of the below aspects in any combination, unless otherwise indicated.

According to a first aspect there is provided a method for identifying a MYCBP2 modulator, the method comprising:

a) contacting MYCBP2, an orthologue, mutant or fragment thereof with a test substance;
b) providing a probe which is capable of interacting with C4520, C4572 and/or the mediator loop region (residues 4515-4531) of active MYCBP2; and
c) detecting whether or not the level of interaction of the probe with MYCBP2, the orthologue, mutant or fragment thereof is modulated as compared to the level of interaction in the absence of the test substance.

For the avoidance of doubt, C4520 is present within the sequence motif GEARCDAEA (SEQ ID NO. 1) and C4572 is present within the sequence motif AVFFCFGTT (SEQ ID NO. 2).

Typically the test substance may be a small molecule electrophile, such as an acrylamide, acrylonitrile or an acrylate, when targeting either identified cysteine residue. As a thiol group is present on a cysteine residue which can react with an electrophile, MYCBP2 activity is postulated to be modulated by:

a) covalent modification of C4520 with an electrophilic small molecule ligand; or
b) covalent modification of C4572 with an electrophilic small molecule ligand;

Alternatively test small molecules may act by disruption of the mobility of the mediator loop region (residues 4515-4531). Disruption of mediator loop mobility may be determined, for example, by a suitable biophysical technique such as nuclear magnetic resonance (NMR) spectroscopy, electron paramagnetic resonance (EPR) spectroscopy or Fluorescence Resonance Energy Transfer (FRET).

The authors have established that MYCBP2 has unexpectedly high and promiscuous esterification activity towards hydroxy-containing small molecules and peptides. Therefore, the use of small molecule hydroxy compounds as proxy substrates can be used for identifying the electrophilic small molecule ligands. We describe such proxy substrates herein as hydroxy probes.

Without wishing to be bound by theory, the inventors believe that the residues C4520 and C4572 of the full-length native MYCBP2 protein are required for the transthiolation between E2-ubiquitin and MYCBP2, and the subsequent relay of ubiquitin, and so one or more of these residues will be understood to comprise the active site. C4572 operates down-stream and interacts with hydroxy probes. In some embodiments the active site comprises at least the residue C4520. In such embodiments, alternative probes are capable of interacting with the residue C4520 (such as those reported in WO 2016/051174).

In embodiments where the level of interaction of said probes with MYCBP2, the orthologue, mutant or fragment thereof is modulated as compared to the level of interaction in the absence of the test substance, the test substance will be understood to be a MYCBP2 modulator.

MYCBP2 is an 0.5 MDa protein found in humans which contains a C-terminal RING domain. The protein plays a role in axon guidance and synapse formation in the developing nervous system, in mammalian cells, this protein regulates the cAMP and mTOR signaling pathways, and may additionally regulate autophagy. In the context of the present invention it will be understood that MYCBP2, the orthologue, mutant or fragment thereof refers to the nucleic acid sequence or expression product thereof, for example DNA, cDNA, mRNA, protein or peptide fragment thereof.

Typically, the MYCBP2, orthologue, mutant or fragment thereof comprises a protein or peptide fragment thereof. Advantageously, this enables the screening of the protein-substrate interaction between the MYCBP2 orthologue, mutant or fragment thereof and the probe.

As used herein, active MYCBP2 will be understood to refer to the enzymatically active MYCBP2 protein.

By "interacting" or "interaction", this will be understood to refer to the association of said probe with an active site of MYCBP2, the orthologue, mutant or fragment thereof. The probes described herein may be covalently modified with a ubiquitin molecule.

Hence, the term probe is used herein to refer to a molecule which is capable of interacting with the active site(s) of active MYCBP2.

It will be appreciated that the residue numbering of MYCBP2 as used herein is in relation to the native full-length MYCBP2 canonical isoform (Uniprot accession number 075592: uniprot.org/uniprot/075592), or as described in Pao et al. *Nature.* 2018 April; 556(7701):381-385. Reference to "C" is with reference to the standard amino acid coding. Hence "C" refers to cysteine residue. Subsequent to the first filing of this application, the SWISSPROT entry for MYCBP2 has been amended to include an insertion, which is outside of the catalytic region discussed herein. However, this has the effect of altering sequence numbering by 38 residues. However, we have retained the original numbering as described in the priority application and the Pao et al paper, and the skilled reader can easily identify the relevant cysteine residues and loop region described herein, from the updated sequence numbering, by adding 38 thereto.

Interaction may comprise specific binding of the hydroxyl probe, or alternative probe to the active site of MYCBP2, the orthologue, mutant or fragment thereof.

As an enzyme, it will be appreciated that there are endogenous substrates of active MYCBP2. The probe may comprise a native substrate of MYCBP2, i.e. an endogenous substrate known to be capable of interacting with the active site of MYCBP2 in vivo. In some embodiments, the probe comprises a non-endogenous substrate of active MYCBP2. By non-endogenous, it will be understood that this includes modified endogenous substrates, as well as substrates which are not known to interact with MYCBP2 in vivo (i.e. artificial substrates).

The probe may be modified or unmodified. For example, the probe may comprise a modified E2, such as an E2-ubiquitin conjugate probe. Examples of such modified probes are provided in WO 2016/051174, the details of which are hereby incorporated by reference. Alternatively, in light of our newly presented promiscuous esterification activity demonstrated by MYCBP2, the probe molecule could be an artificial hydroxy containing substrate such as a small molecule or peptide. Activity can be assessed by measuring MYCBP2 and proxy substrate dependent discharge of ubiquitin from upstream E2 conjugating enzyme, or, direct esterification of the proxy substrate with ubiquitin, as described herein.

By "modulator", as used herein, it will be understood that the MYCBP2 modulator increases or decreases the activity of MYCBP2, the orthologue, mutant or fragment thereof relative to normal levels (i.e. the level in the absence of the test substance). A modulated level of interaction as compared to the level of interaction in the absence of the test substance may be as a result of a modulated level of activity of MYCBP2.

In some embodiments the modulator functions by disrupting the nucleic acid sequence encoding the MYCBP2, orthologue, mutant or fragment thereof. In some embodiments the modulator functions by disrupting the nucleic acid sequence encoding the active site of the MYCBP2, orthologue, mutant or fragment thereof. For example, step a) may comprise contacting the nucleic acid sequence of MYCBP2, an orthologue, mutant or fragment thereof with a test substance and expressing the protein or peptide product thereof of the contacted nucleic acid sequence. The activity of the expressed protein or peptide product can then be measured. In such embodiments, step c) comprises detecting whether or not the level of interaction of the probe with the expressed protein or peptide product of MYCBP2, the orthologue, mutant or fragment thereof is modulated as compared to the level of interaction in the absence of the test substance. In such embodiments, "absence of the test substance" will be understood to refer to wherein the nucleic acid sequence of MYCBP2, an orthologue, mutant or fragment thereof is not contacted with the test substance in step a).

In other embodiments, step a) may comprise contacting the MYCBP2, orthologue, mutant or fragment thereof with a test substance, wherein the MYCBP2, orthologue, mutant or fragment thereof comprises a protein or peptide fragment thereof. In such embodiments, step c) comprises detecting whether or not the level of interaction of the probe with the protein or peptide fragment thereof of MYCBP2, the orthologue, mutant or fragment thereof is modulated as compared to the level of interaction in the absence of the test substance.

The modulator may be an inhibitor, i.e. it decreases the activity of MYCBP2. In such embodiments, step c) comprises detecting whether or not the level of interaction of the probe with MYCBP2, the orthologue, mutant or fragment thereof is reduced as compared to the level of interaction in the absence of the test substance. The activity of MYCBP2 may be reduced by the modulator by at least 10%, at least 20%, at least 30%, at least 40%, at least 50%, at least 60%, at least 70%, at least 80%, at least 90% or 100%.

The inhibitor may function by covalent inactivation of the active site. Alternatively, or in addition to, the inhibitor may function by disrupting binding of the probe to MYCBP2, the orthologue, mutant or fragment thereof. In some embodiments the inhibitor functions by disrupting the nucleic acid sequence encoding the MYCBP2, orthologue, mutant or fragment thereof.

Disrupting a nucleic acid sequence may comprise cleavage of the nucleic acid sequence, deletion of a portion of the nucleic acid sequence, degradation of the nucleic acid sequence, destabilization of the nucleic acid sequence and/or insertion of a further nucleic acid sequence into the nucleic acid sequence.

Any suitable substance may be tested as a possible MYCBP2 modulator. It is, however, envisaged, that the method may be used for identifying MYCBP2 modulators for use in therapy and/or prophylaxis, for example in the therapy and/or prophylaxis of neuronal damage, for example, axon degeneration-associated injury and disease. In some embodiments, the test substance comprises an siRNA, an miRNA, a CRISPR/Cas system, a peptide, a protein, an enzyme, a small molecule, an aptamer, an antibody or an antibody fragment (such as a Fab or F(ab')2) fragment, an scFV antibody or any other functional antigen-binding fragment.

As used herein, a "small molecule" is a chemical compound having a molecular weight of no more than 2 Kilo Daltons (kDa). In some embodiments the small molecule has a molecular weight of no more than 1 KDa, or 900 daltons (Da). In some embodiments, the small molecule has a molecular weight of no more than 700 or no more than 500 Da. The small molecule may be an organic compound. Exemplary compounds may include acrylamides, acrylonitriles and acrylates.

In some embodiments the test substance comprises a peptide, a protein, an enzyme, a small molecule, an aptamer, an antibody or an antibody fragment (such as a Fab or F(ab')2) fragment, an scFV antibody or any other functional antigen-binding fragment.

The test substance may comprise an aptamer, an antibody or an antibody fragment (such as a Fab or F(ab')2) fragment, an scFV antibody or any other functional antigen-binding fragment.

In some embodiments, the test substance comprises a CRISPR/Cas system, an siRNA or an miRNA. In such embodiments, step a) comprises contacting the nucleic acid sequence of MYCBP2, an orthologue, mutant or fragment thereof with the test substance and expressing the protein or peptide product thereof of the MYCBP2, orthologue, mutant or fragment thereof contacted with the test substance. In such embodiments, step c) comprises detecting whether or not the level of interaction of the probe with the protein or peptide product of step a) is modulated as compared to the level of interaction in the absence of the test substance. It will be appreciated that in such embodiments, a modulator functions by modulating the nucleic acid sequence of MYCBP2, an orthologue, mutant or fragment thereof such that the interaction of the probe with the resulting protein or peptide product is modulated.

As the skilled person will be aware, the CRISPR/Cas system is a molecular tool by which a target nucleic acid sequence, typically DNA, can be targeted and cleaved. The target nucleic acid sequence is targeted by a guide RNA (CRISPR RNA or crRNA), the guide RNA forming a duplex with a further small RNA known as trans-activating RNA (tracrRNA). The duplex forms a complex with a Cas protein, such that the Cas protein acts upon the target nucleic acid sequence, for example by cleaving the selected nucleic acid sequence.

For the guide RNA to target the target nucleic acid sequence, a "protospacer adjacent motif" (PAM) region downstream of the target nucleic acid sequence is required. Hence, the CRISPR/Cas system will be understood to refer to a guide RNA which is specific for a target nucleic acid sequence, a CAS protein and a PAM region. The CRISPR/Cas system will be understood to also comprise the further small RNA. In some embodiments the CRISPR/Cas system comprises a single guide RNA (sgRNA), the sgRNA comprising the crRNA and the tracrRNA. In some embodiments the CRISPR/Cas system further comprises a repair template. As the skilled person will appreciate, a repair template is a nucleic acid sequence which comprises a specific nucleic acid sequence for insertion into a cleavage site.

In the context of the present invention the target nucleic acid sequence will be understood to be a nucleic acid sequence of the MYCBP2, the orthologue, mutant or fragment thereof. The target nucleic acid sequence may be at least 20 base pairs. In some embodiments the target nucleic acid sequence is no more than 70 base pairs. In some embodiments the target nucleic acid sequence is at least 20 base pairs and no more than 55 base pairs.

Advantageously, therefore, the CRISPR/Cas system may be used to modify a nucleic acid sequence of the MYCBP2, the orthologue, mutant or fragment thereof by cleavage and/or insertion of a specific nucleic acid sequence. The activity of the modified expressed protein or peptide can then be detected.

In embodiments wherein the test substance comprises a CRISPR/Cas system, various methods can be envisaged for contacting the MYCBP2, orthologue, mutant or fragment target nucleic acid sequence. For example, contacting the MYCBP2, orthologue, mutant or fragment target nucleic acid sequence may comprise contacting a cell with the CRISPR/Cas system by, for example, electroporation, transfection or transduction.

The contacted MYCBP2, orthologue, mutant or fragment target nucleic acid sequence can then be isolated from the cell, or provided in the form of a cell lysate.

Suitable methods for incorporating the PAM region proximal to the target nucleic acid sequence, the generation of specific guide RNA(s), tracrRNA(s) and/or sgRNA(s), and the method of using the CRISPR/Cas system will be known to the skilled person and will also be readily available from various references such as references 42-63.

Web-based tools, as detailed in references 64-66, may also be utilised to help identify suitable CRISPR target sequences In some embodiments, the Cas protein has endonuclease activity. Thus, in such embodiments, the Cas protein is capable of cleaving the selected nucleic acid region. In other embodiments, the Cas protein is nuclease dead (i.e. has reduced or no nuclease activity). When the Cas protein is nuclease dead, the Cas protein may be attached to a transcription activator or a transcription repressor, such that the expression of the selected nucleic acid is capable of being upregulated or downregulated, respectively.

Desirably, the Cas protein comprises the Cas9 protein.

The method is suitable for testing a plurality of test substances. Advantageously, this provides a high-throughput screening assay for the fast and accurate identification of MYCBP2 modulators.

In some embodiments the probe comprises a hydroxyl group, the probe capable of interacting with active MYCBP2 via the hydroxyl group. In embodiments where the probe comprises a hydroxyl group, the probe may be capable of interacting with the residue C4520 and optionally the residue C4572. The hydroxyl group may be present on an amino acid.

The interaction may comprise esterification by MYCBP2, the orthologue, mutant or fragment thereof of the hydroxyl group with ubiquitin.

Thus, in some embodiments, the method further comprises providing ubiquitin.

The probe may comprise a peptide. In some embodiments the probe comprises a small molecule. Exemplary proxy substrates tested herein and shown as being functional are glycerol, tris(hydroxymethyl)aminomethane, HEPES (4-(2-hydroxyethyl)-1-piperazineethanesulfonic acid), serine, threonine, and small serine/threonine containing peptides. However, any small molecule with an exposed hydroxy group maybe expected to serve as a proxy substrate.

In embodiments wherein the probe comprises a hydroxyl group, the level of interaction between the probe and MYCBP2, the orthologue, mutant or fragment thereof may be determined indirectly, for example by monitoring the esterification of the probe molecule with ubiquitin.

Most known E3 ligases exhibit selectivity for lysine residues. Consequently, many E3 ligases ubiquitinate a lysine residue(s) on a substrate. Surprisingly, the present inventors have found the MYCBP2 exhibits selectivity for threonine, and, to a lesser extent, serine, rather than lysine. Hence, in some embodiments, the probe may comprise threonine or serine, preferably threonine.

In some embodiments the method further comprises providing one or more other components of the ubiquitin enzymatic cascade. Other components of the ubiquitin enzymatic cascade include ATP, E1 activating enzyme, E2 conjugating enzyme (also referred to as E2 or E2 enzyme) and/or ubiquitin. By providing one or more of these components, the endogenous enzymatic cascade can be recreated in full or part. Preferably, in embodiments wherein the probe comprises a hydroxyl group, the method further comprises providing one or more of the other components of the ubiquitin enzymatic cascade. In some embodiments the method comprises providing ATP, E1 activating enzyme, E2 and ubiquitin. The E2 enzyme may be selected from variants of UBE2D1, UBE2D2, UBE2D3, UBE2D4 and UBE2E1. In some embodiments the E2 enzyme is selected from UBE2D1, UBE2D1 C86, UBE2D1 C86 AzF3(X) and UBE2D3.

In other embodiments, the probe comprises an activated biological molecule corresponding to the formula (I)

(I)

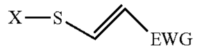

wherein X is a biological molecule and EWG is an electron withdrawing group. In this embodiment, the probe is capable of interacting with active MYCBP2 by being capable of forming a covalent bond by click-like thiol addition reaction when in proximity with a cysteine group of the active site of the active MYCBP2. In such embodiments, step c) comprises detecting formation of one or more conjugates which may be formed, wherein a modulated formation of one or more conjugates is indicative of a modulated level of interaction as compared to the level of interaction in the absence of the test substance.

Preferably a sulphur containing moiety of the biological molecule is derivatised in order to form the activated biological molecule. Typically the biological molecule may be a protein or peptide and the sulphur containing moiety is a cysteine, especially an internal cysteine present within the protein or peptide. The cysteine may be a naturally occurring cysteine in the biological molecule, or may be introduced into the molecule In a preferred embodiment the biological molecule is a ubiquitin conjugating enzyme (E2). Preferably one or more catalytically active cysteine residues is/are derivatised. The E2 enzyme may be selected from UBE2D1, UBE2D2, UBE2D3, UBE2D4 and UBE2E1. In some embodiments the E2 enzyme is selected from UBE2D1, UBE2D1 C86, UBE2D1 C86 AzF3(X) and UBE2D3.

In embodiments wherein the probe comprises an activated biological molecule, the probe may be capable of interacting with residue C4520. The activated biological molecule may or may not be capable of interacting with residue C4572.

In embodiments wherein the biological molecule is E2, the level of interaction between the probe and MYCBP2, the orthologue, mutant or fragment thereof may be determined by probe- and MYCBP2-dependent discharge of ubiquitin from E2.

The electron withdrawing group (EWG) may be any suitable EWG known to the skilled addressee. Examples of suitable EWGs include —$NO_2$, —$NR_3^+$, —$CF_3$, or other trihalide, —CN, —SOOR, —SOOH, —COOH, —COOR, —CHO, —COR, wherein R is typically H, NH, or C1-C4 alkyl (e.g. methyl) or alkenyl. In a preferred embodiment EWG is —CN, or —$CO_2Me$. In one embodiment the EWG is not further substituted. In another embodiment the EWG may be further substituted in order to, for example, provide a functional group which is capable of reacting with a moiety of another molecule and forming a covalent bond.

For example, the EWG group may be substituted with a molecule comprising an alyknyl group. Such an alkynyl group may react by a click chemistry type cycloaddtion reaction with an azide moiety to form a 1,2,3-triazole.

In accordance with this embodiment of the invention there may be provided an activated biological molecule conjugate probe, wherein the activated biological molecule conjugate probe corresponds to formula (II):

(II)

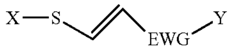

wherein X is a first biological molecule, EWG is an electron withdrawing group and Y is a further biological molecule.

In one embodiment the EWG is bound to the biological molecule Y by way of a triazole group. In accordance with this embodiment, conjugate (II), more specifically conforms to conjugate (III) below:

(III)

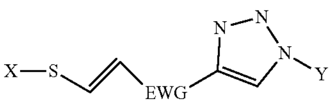

Such a conjugate may be formed in accordance with the following reaction:

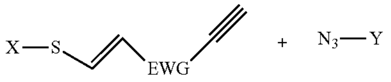

The first biological molecule X may be an enzyme and the further biological molecule Y may, for example, be a substrate or ligand for the enzyme. For example, the enzyme may be an E2 ubiquitin conjugating enzyme and the substrate is ubiquitin. In embodiments where the enzyme is an E2 ubiquitin conjugating enzyme and the substrate is ubiquitin, there is no requirement for the method to provide ATP, E1, unmodified E2 or the endogenous protein substrate.

The probe may be conjugated to a surface. The probe may be conjugated to the surface by passive adsorption, for example hydrophobic or hydrophobic/ionic interaction between the probe and the surface. In some embodiments the probe comprises a moiety for conjugation to the surface. For example, the probe may comprise a functional group as the moiety, which is capable of reacting with a moiety on the surface to form a covalent bond. In such embodiments the functional group of the probe may comprise an amine or sulfhydryl group. The surface moiety may comprise an amine or carboxyl group. In some embodiments the probe is conjugated to the surface by high-affinity non-covalent reactions.

The surface may comprise one or more multi-well plates, which conveniently enable high-throughput analysis. In such embodiments, active MYCBP2, the orthologue, mutant or fragment thereof can interact with the probe so that the active MYCBP2, the orthologue, mutant or fragment thereof becomes tethered to the surface. This enables detection, for example, by antibody-based detection technology such as ELISA.

The probe of the present invention may comprise a label, for example an affinity tag. The term "label" as used herein denotes a biochemical marker or tag, i.e. an easily recognizable chemical moiety, e.g. a protein, peptide, or small molecule. The label may be covalently attached to the probe. In embodiments wherein the probe comprises an N and a C terminus, for example where the probe comprises a peptide, the label may be covalently attached to the N or C terminus, preferably the N-terminus. Numerous labels are known to the skilled addressee and include affinity labels, e.g. affinity tags (Kimple and Sondek, BioTechniques (2002), 33:578-590), fluorophores (such as TAMRA, DAPI, fluorescein, Cy3, Cy5, SYBR green and the like), biotin, epitope tags or radioactive labels.

In some embodiments, the method is carried out in the absence of endogenous MYCBP2 protein substrate. The method may be carried out in the absence of one or more other components of the ubiquitin enzymatic cascade, for example one or more of ATP, E1 and/or E2 ligases. In some embodiments, the method does not comprise providing an endogenous MYCBP2 substrate, ATP, E1 and/or E2. Advantageously, this provides a method requiring only minimal reagents that can be carried out with minimum cost and complexity.

The method may further comprise the preliminary step of providing the MYCBP2, orthologue, mutant or fragment thereof. In some embodiments, the MYCBP2, orthologue, mutant or fragment thereof is endogenous, for example provided in the form of a cell lysate. This provides physiological context to the method. For example, in embodiments where step a) comprises contacting a mutant of MYCBP2 with a test substance, the mutant may have been isolated from a particular subject. The method can therefore advantageously be used to identify MYCBP2 modulators specific for the particular subject. Where the modulator(s) can be used in the therapy and/or prophylaxis of the subject, this provides a method of obtaining personalised therapy for the subject.

In other embodiments, the MYCBP2, orthologue, mutant or fragment thereof may be recombinant. By "recombinant" it will be understood that this refers to MYCBP2, the orthologue, mutant or fragment thereof which has been genetically engineered, for example comprising or being expressed from a nucleic acid construct.

The skilled person will therefore appreciate that the term "recombinant" defines the endogenous MYCBP2, orthologue, mutant or fragment thereof provided and/or expressed in a nucleic acid construct, and/or a modified MYCBP2, orthologue, mutant or fragment thereof provided and/or expressed in a nucleic acid construct.

In some embodiments, the MYCBP2, orthologue, mutant or fragment thereof may be provided in overexpressed form in the method. Overexpressed will be understood to refer to increased expression levels relative to the endogenous expression levels.

Typically, overexpression is achieved by expressing a nucleic acid construct comprising the MYCBP2, orthologue, mutant or fragment gene or cDNA thereof.

In some embodiments step a) comprises contacting a fragment of MYCBP2 with a test substance. By fragment, we include that the fragment of MYCBP2 can vary from the naturally occurring nucleotide or peptide sequence with the proviso that the fragment substantially retains the biological activity of MYCBP2. By retain the biological activity of MYCBP2 it is meant that the fragment retains at least a portion of the enzymatic activity as compared to the native MYCBP2. Typically the fragment retains at least 50%, such as 60%, 70%, 80% or 90% activity. In some instances the fragment may have a greater enzymatic activity than the native MYCBP2. In some embodiments the fragment may display an increase in another physiological feature as compared to the native enzyme. For example, the fragment may possess a greater half-life in vitro and/or in vivo, as compared to the native enzyme.

Without wishing to be bound by theory, the inventors believe that the residues C4520 and C4572 of the full-length native MYCBP2 protein are required for the transthiolation between E2-ubiquitin and MYCBP2, and the subsequent relay of ubiquitin. Hence, it will be understood that the fragment comprises at least the active site of the MYCBP2 active protein. Thus, the fragment comprises one or more of the residues C4520 and C4572. Preferably, the fragment comprises at least the residues C4520 to C4572 of the full-length native MYCBP2 protein. Without wishing to be bound be theory the inventors believe that the new teaching and unique nature of the cooperative mechanism adopted by C4520 and C4572, and the reactivity of the cysteine residues, makes these sites privileged features for targeting with modulators that may have therapeutic benefit.

In addition to the active site, it is preferred if the fragment has a sequence which has at least 5%, at least 10%, at least 20%, at least 30%, at least 40%, at least 50%, at least 60%, at least 70%, at least 80% or at least 90% of the native sequence.

In some embodiments, the fragment further comprises the RING domain of MYCBP2, which is understood to be residues 4390-4441 of the full-length native MYCBP2 protein.

In some embodiments, the fragment's C-terminus is truncated relative to the full-length native MYCBP2 protein.

In some embodiments, the fragment comprises or consists of residues 4390 to 4572 of the full-length native MYCBP2 protein.

Preferably, the fragment's N-terminus comprises or consists of residue 4390. In other embodiments, the fragment's N terminus comprises or consists of residue 4378.

In some embodiments, the fragment comprises or consists of residues 4378 to 4572.

In some embodiments, the fragment's N terminus comprises or consists of residue 3224 of the full-length native MYCBP2 protein. In other embodiments, the fragment's N terminus comprises or consists of residue 3156 of the full-length native MYCBP2 protein.

In some embodiments, the fragment's C-terminus comprises or consists of any residue of from 4572 to 4640 of the full-length native MYCBP2 protein.

In some embodiments, the fragment comprises or consists of residues 4390 to 4640 of the full-length native MYCPB2 protein.

In some embodiments, the fragment comprises or consists of residues 4378-4640 of the full-length MYCBP2 protein. This fragment comprises the RING domain, the active site and the subsequent C-terminal residues. The inventors have found that this fragment will efficiently esterify the hydroxyl probes of the present invention, for example a probe comprising a hydroxyl group, with ubiquitin.

In some embodiments, the fragment comprises or consists of isoform 2 of MYCBP2. This will be understood to refer to the full-length canonical isoform of MYCBP2 minus residues 3901 to 3903.

The fragment may comprise a fragment of an orthologue.

Various orthologues of MYCBP2 will be known to the skilled person. For example, orthologues of MYCBP2 may include, but not be limited to mouse MYCBP2, zebrafish Esrom/phr1, *Drosophila* Highwire and *C.elegans* RPM-1.

In some embodiments step a) comprises contacting an orthologue of MYCBP2 with a test substance. The orthologue may be selected from mouse Phr1, zebrafish Esrom/phr1, *Drosophila* Highwire and *C.elegans* RPM-1. In some embodiments the orthologue comprises or consists of *Drosophila* Highwire.

Preferably, the method is an in vitro method.

Detection of the level of interaction of the probe with MYCBP2, the orthologue, mutant or fragment thereof may be any suitable analytical technique, various techniques being known to the skilled person.

Detection may be using magnetic separation, immunological separation, gel filtration chromatography, affinity chromatography, column chromatography, displacement chromatography, electro chromatography, gas chromatography, high performance liquid chromatography, ion chromatography, micellar electrokinetic chromatography, normal phase chromatography, paper chromatography, reversed-phase chromatography, size exclusion chromatography, thin layer chromatography, gel electrophoresis, centrifugation, adhesion, flow cytometry, or other techniques known to the skilled addressee.

The detection may be carried out, for example by reducing SDS gel electrophoresis and immunoblotting with an antibody specific for the probe or tag bound thereto. Alternatively detection may be carried out by performing mass spectrometry.

In embodiments where the interaction comprises esterification of the hydroxyl group of the probe with ubiquitin (by MYCBP2, the orthologue, mutant or fragment thereof), any suitable techniques that allow the resolution of unmodified ubiquitin from the ubiquitin adducted probe may be used. For example, the hydroxyl group may be labelled with an appropriate reporter and the reporter detected. The reporter may include, but may not be limited to, a fluorophore, epitope tag or biotin.

Alternatively, a "catch and release" detection technique may be suitable in embodiments where the interaction comprises esterification by MYCBP2, the orthologue, mutant or fragment thereof of the hydroxyl group of the probe with ubiquitin. Without wishing to be bound by theory, the inventors believe that following interaction, the ester linkage between ubiquitin and the hydroxyl group is labile. A catch and release detection technique could employ this lability by facilitating ester cleavage. For example, ester cleavage could be mediated by a base such as hydroxide or hydroxylamine. The cleaved ubiquitin and/or hydroxyl probe may be detected by any suitable analytical technique, for example by ELISA or fluorescence methods such as FRET or fluorescence polarization.

In embodiments where the probe comprises an activated biological molecule, detection may be by any suitable technique which can resolve the unmodified activated biological molecule from activated biological molecule bound to the MYCBP2, orthologue, mutant or fragment thereof. For example, the activated biological molecule may comprise a label which can be detected by fluorescence polarisation. In embodiments wherein the activated biological molecule comprises an E2-ubiquitin conjugate probe, detection may be by resolving the discharged ubiquitin from E2 using any suitable analytical technique.

Other forms of detection could include that the activated biological molecule and the MYCBP2, orthologue, mutant or fragment thereof may each comprise a label. Once both labels are in close proximity, binding of the activated molecule to the MYCBP2, orthologue, mutant or fragment thereof may be detected by FRET (Fluorescence Resonance Energy Transfer) AlphaScreen (Perkin Elmer) or HTRF (Homogenous Time-Resolved Fluorescence) technology.

According to a second aspect there is provided a method for identifying a MYCBP2 modulator, the method comprising:

a) contacting MYCBP2, an orthologue, mutant or fragment thereof with a test substance;
b) providing a probe which is capable of interacting with active MYCBP2, the probe comprising a hydroxyl group which is capable of interacting with C4520 and optionally C4572 of MYCBP2; and
c) detecting whether or not the level of interaction of the probe with MYCBP2, the orthologue, mutant or fragment thereof is modulated as compared to the level of interaction in the absence of the test substance.

The present invention also provides a method for identifying a MYCBP2 modulator, the method comprising:

a) contacting MYCBP2, an orthologue, mutant or fragment thereof with a test substance;
b) providing a probe which is capable of interacting with active MYCBP2; the probe comprising an activated biological molecule according to the formula (I)

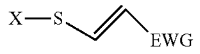

(I)

wherein X is a biological molecule and EWG is an electron withdrawing group; and c) detecting whether or not the level of interaction of the probe with MYCBP2, the orthologue, mutant or fragment thereof is modulated as compared to the level of interaction in the absence of the test substance.

In a further aspect there is provided a kit comprising a probe as defined herein together with MYCBP2, an orthologue, mutant or fragment thereof for use in accordance with the present invention. Advantageously, a kit may be used to analyse the activity of MYCBP2 isolated in a sample from a subject. A level of activity analysed may be used as a biomarker for the subject. The biomarker may be used to determine whether or not a subject has a particular disease or condition. For example, a level of activity above or below a particular activity threshold level may be indicative of the subject having a particular disorder. In some instances, a level of activity above a particular activity threshold level may be indicative of the subject having a particular disorder, for example a neurological disorder.

An MYCBP2 modulator as identified in accordance with the invention may find use in a method of treating or preventing neuronal damage, wherein the MYCPB2 modulator is capable of interacting with the active site of MYCBP2.

As described above, the inventors believe that the residues C4520 and C4572 of the full-length native MYCBP2 protein are required for the transthiolation between E2-ubiquitin and MYCBP2, and the subsequent relay of ubiquitin. Hence, the active site will be understood to refer to residue C4520 and/or C4572.

The inventors have observed that MYCBP2 can ubiquitinate the non-lysine serine, and preferably threonine residues of endogenous substrates. For example, the inventors have found that MYCBP2 can ubiquitinate Nicotinamide Mononucleotide Adenyltransferase (NMNAT2), an enzyme implicated in axonal degeneration, by esterification. The inventors' observations reveal potential new roles for MYCBP2 in neuronal damage. Accordingly, the present invention contemplates the use of modulators of MYCBP2 which are capable of modulating MYCBP2 activity, for example, as may be identified from the method of identifying modulators described above.

Without wishing to be bound by any particular theory, neuronal damage such as axonal degeneration may be due at least in part to the ability of MYCBP2 to ubiquitinate neuronal-associated molecules such as NMNAT2. Desirably, therefore, the modulator may be an inhibitor of MYCBP2.

Hence, in some teachings the modulator decreases the activity of MYCBP2. The activity of MYCBP2 may be reduced by the modulator by at least 10%, at least 20%, at least 30%, at least 40%, at least 50%, at least 60%, at least 70%, at least 80%, at least 90% or 100%.

As used herein "treating" or "treatment" refers to reducing or alleviating symptoms associated with the neuronal damage. As used herein "preventing" or "prevention" refers to protecting a subject from neuronal damage.

The modulator is capable of interacting with the residue C4520 and/or C4572 of MYCBP2, for example by binding. Preferably, by interacting with one or more of these residues, the active site of MYCBP2 is blocked and so MYCBP2 activity is reduced or prevented.

The neuronal damage may be from trauma or as a side-effect of a neurotoxic therapy, for example chemotherapy. As used herein, "trauma" will be used to define neuronal injury, for example as a result of a physical force to the subject, such as a fall or being struck with an object. Neuronal damage may also be acquired such as from side effects from clinically used neurotoxic medicines such as those employed in cancer chemotherapy In some embodiments the neuronal damage is as an effect of a disorder such as a neurological disorder, diabetes, HIV (Human immunodeficiency virus) infection, AIDS (acquired immunodeficiency syndrome) and/or ischemia.

In some embodiments the neuronal damage is from one or more neurological disorder(s). "Neurodegenerative disorder" will be understood to refer to disorder in which neurons degenerate in function and/or structure and/or die. Degeneration is typically gradual but in some instances may be sudden. Example neurodegenerative diseases include, but are not limited to, Alzheimer's disease, Diffuse Lewy Body disease, Fronto-temporal dementia (FTD) (Pick's disease) (including FTD subtypes behavioural variant/frontal variant Fronto-temporal dementia, semantic dementia and progressive non-fluent aphasia), Corticobasal degeneration, Argyrophilic Grain disease, Parkinson's disease, Parkinson's disease dementia, Perry syndrome, Familial British dementia, Familial Danish dementia, Progressive Supranuclear Palsy, Multiple System Atrophy, Lewy Body disease (Dementia with Lewy bodies), Huntington's disease, Spinobulbar Muscular Atrophy (Kennedy's disease), Dentatorubral-pallidoluysian Atrophy, Spinocerebellar ataxias 1, 2, 3, 6, 7 and 17, Motor Neurone disease (Amyotrophic Lateral Sclerosis), Multiple Sclerosis (MS), Prion diseases including Creutzfeldt-Jakob disease, variant Creutzfeldt-Jakob disease (Bovine spongiform encephalopathy), Kuru, Fatal Familial Insomnia, Gertsmann-Straussler-Scheinker syndrome, Charcot-Marie Tooth diseases, optic neuropathies such as Glaucoma, and Variable Protease Sensitive prionopathy. Other neurodegenerative diseases will be known to a skilled person.

Human symptoms of neurodegenerative disorder may include dementia (including memory loss and/or a reduction in cognitive capacity as measured by standard tests known to a skilled person) mood changes, reduced mobility, reduced or no speech quality, clumsiness, difficulty balancing, uncontrolled movements, trembling limbs, stiff limbs or decreased speed of movement. In the context of human symptoms, "reduced" refers to a decreased value, relative to individuals without the neurodegenerative disease. Other human symptoms will be known to a skilled person.

The neurodegenerative disorder may be selected from one or more of Alzheimer's disease, Diffuse Lewy Body disease, Amyotrophic Lateral Sclerosis (ALS), Fronto-temporal dementia (FTD) (Pick's disease) (including FTD subtypes behavioural variant/frontal variant Fronto-temporal dementia, semantic dementia and progressive non-fluent aphasia), Corticobasal degeneration, Argyrophilic Grain disease, Parkinson's disease, Parkinson's disease dementia, Perry syndrome, Familial British dementia, Familial Danish dementia, Progressive Supranuclear Palsy, Multiple System Atrophy, Lewy Body disease (Dementia with Lewy bodies), Huntington's disease, Spinobulbar Muscular Atrophy (Kennedy's disease), Dentatorubral-pallidoluysian Atrophy, Spinocerebellar ataxias 1,2,3,6,7 and 17, Motor Neurone disease (Amyotrophic Lateral Sclerosis), Multiple Sclerosis (MS), Prion diseases including Creutzfeldt-Jakob disease, variant Creutzfeldt-Jakob disease (Bovine spongiform encephalopathy), Kuru, Fatal Familial Insomnia, Gertsmann-Straussler-Scheinker syndrome, Charcot-Marie Tooth diseases, optic neuropathies such as Glaucoma, and Variable Protease Sensitive prionopathy.

In some embodiments the neurodegenerative disorder is selected from one or more of Alzheimer's disease, Parkinson's disease, Amyotrophic Lateral Sclerosis (ALS) Huntington's disease, Motor Neurone disease, Gertsmann-Straussler-Scheinker syndrome, Charcot-Marie Tooth diseases, optic neuropathies such as Glaucoma, Creutzfeldt-Jakob (prion) disease and Multiple Sclerosis (MS).

In some embodiments, the neurodegenerative disorder is selected from one or more of Alzheimer's disease, Parkinson's disease, Amyotrophic Lateral Sclerosis (ALS) Huntington's disease, Motor Neurone disease, Creutzfeldt-Jakob (prion) disease and Multiple Sclerosis (MS).

The neurodegenerative disorder may be selected from one or more of Alzheimer's disease, Parkinson's disease, Amyotrophic Lateral Sclerosis (ALS) Huntington's disease and Motor Neurone disease.

In some embodiments the neurodegenerative disorder is selected from one or more of Alzheimer's disease, Parkinson's disease and Huntington's disease.

The neurodegenerative disorder may be selected from one or more of Alzheimer's disease, Parkinson's disease, Amyotrophic Lateral Sclerosis (ALS) and Huntington's disease. In some embodiments, the neurodegenerative disorder is selected from Alzheimer's disease or Parkinson's disease.

some embodiments, the modulator comprises a peptide, a protein, an enzyme, an aptamer, an antibody or an antibody fragment (such as a Fab or F(ab')2) fragment, an scFV antibody or any other functional antigen-binding fragment.

In some embodiments the modulator comprises or consists of an antibody, an antibody fragment, a peptide or an aptamer.

The modulator may be an antibody or an antibody fragment

In embodiments wherein the modulator comprises an aptamer, the aptamer may comprise DNA or RNA.

MYCBP2 modulators identified in accordance with the present invention may find use in a method of treating or preventing neuronal damage, wherein the MYCPB2 modulator is capable of disrupting the binding of MYCBP2 to its natural substrate or ligand Disrupting a nucleic acid sequence may comprise cleavage of the nucleic acid sequence, deletion of a portion of the nucleic acid sequence, degradation of the nucleic acid sequence, destabilization of the nucleic acid sequence and/or insertion of a further nucleic acid sequence into the nucleic acid sequence.

In some embodiments the modulator comprises an siRNA, an miRNA or a CRISPR/Cas system. In some embodiments, the modulator comprises a CRISPR/Cas9 system.

In embodiments where the modulator comprises an siRNA, an miRNA or a CRISPR/Cas system as described herein, the method of treating or preventing neuronal damage may comprise isolating a cell(s) from a subject, contacting the cell(s) with the siRNA, miRNA or CRISPR/Cas system and administering the contacted cell(s) to the subject.

In a further teaching there is taught a method of treating or preventing neuronal damage in a subject, the method comprising administering an MYCBP2 modulator to the subject.

The neuronal damage may be in a mammalian subject, for example a human. Non-human subjects to which the invention is applicable include pets, domestic animals, wildlife and livestock, including dogs, cats, cattle, horses, sheep, goats, deer and rodents. It will thus be appreciated that the modulator may be provided in a therapeutically effective amount, i.e. an amount of the modulator which, when administered to a subject, is sufficient to eliminate, reduce or prevent neuronal damage.

Administration of the modulator may be by any suitable route, including but not limited to, injection (including intravenous (bolus or infusion), intra-arterial, intraperitoneal, subcutaneous (bolus or infusion), intraventricular, intramuscular, or subarachnoidal), oral ingestion, inhalation, topical, via a mucosa (such as the oral, nasal or rectal mucosa), by delivery in the form of a spray, tablet, transdermal patch, subcutaneous implant or in the form of a suppository. The mode of administration may depend on the neuronal damage being treated.

In embodiments wherein the modulator is a peptide or protein, a nucleic acid sequence encoding the peptide or protein may be provided in a suitable vector, for example a plasmid, a cosmid or a viral vector. Thus, also provided is a vector (i.e. a construct), comprising a nucleic acid sequence which encodes the protein or peptide. The nucleic acid sequence is preferably operably linked to a suitable promoter. The invention further relates to a composition comprising the vector.

Modulators which are nucleic acids, such as siRNAs, miRNAs or the CRISPR/Cas system, may be modified (e.g. via chemical modification of the nucleic acid backbone), or delivered in suitable delivery system which protects the nucleic acids from degradation and/or immune system recognition. Examples of suitable delivery systems include nanoparticles, lipid particles, polymer-mediated delivery systems, lipid-based nanovectors and exosomes.

In some embodiments, a dose of between 0.1 μg/kg of body weight and 1 g/kg of body weight of modulator according to the fifth aspect of the invention may be administered for the treatment or prevention of neuronal damage, depending upon the specific modulator used.

The modulator may be administered as a single dose or as multiple doses. Multiple doses may be administered in a single day (e.g. 2, 3 or 4 doses at intervals of e.g. 3, 6 or 8 hours). The modulator may be administered on a regular basis (e.g. daily, every other day, or weekly) over a period of days, weeks or months, as appropriate.

It will be appreciated that optimal doses to be administered can be determined by those skilled in the art, and will vary depending on the particular modulator in use, the strength of the preparation, the mode of administration and the advancement or severity of the neuronal damage. Additional factors depending on the particular subject being treated will result in a need to adjust dosages, including subject age, weight, gender, diet, and time of administration. Known procedures, such as those conventionally employed by the pharmaceutical industry (e.g. in vivo experimentation, clinical trials, etc.), may be used to establish specific formulations for use according to the invention and precise therapeutic dosage regimes.

Embodiments of the invention will now be described by way of example and with reference to the accompanying figures, in which:

FIG. 1A, FIG. 1B, and FIG. 1C show the activity-based proteomics of E3 ligases;

FIG. 2A, FIG. 2B, FIG. 2C, FIG. 2D, FIG. 2E, and FIG. 2F show the LC-MS characterization of biotinylated ABP intermediates and biotinylated ABPs;

FIG. 3A, FIG. 3B, FIG. 3C, and FIG. 3D show the activity-based proteomic profiling of neuroblastoma SH-SY5Y cells;

FIG. 4A, FIG. 4B, FIG. 4C, FIG. 4D, and FIG. 4E show MYCBP2 is a novel class of E3 ligase and data support of a cysteine relay mechanism, wherein the ABP and E2 sequences shown are of SEQ ID NO. 3 and SEQ ID. NO. 4 respectively;

FIG. 5A, FIG. 5B, and FIG. 5C show ABPs label C4520 within $MYCBP2_{cat}$ with high selectivity, wherein the ABP and E2 sequences shown are of SEQ ID NO. 3 and SEQ ID. NO. 4 respectively;

FIG. 6A, FIG. 6B, FIG. 6C, FIG. 6D, FIG. 6E, and FIG. 6F show the esterification activity of $MYCBP2_{cat}$ and further data in support of a dual cysteine mechanism that operates in cis;

FIG. 7A, FIG. 7B, FIG. 7C, FIG. 7D, and FIG. 7E show that MYCBP2 ubiquitinates serine and threonine with selectivity for threonine, wherein the peptide sequence EGTGN is SEQ ID NO. 5, EGSGN is SEQ ID NO. 6 and EGKGN is SEQ ID NO. 7;

FIG. 8A, FIG. 8B, FIG. 8C, FIG. 8D, FIG. 8E, FIG. 8F, FIG. 8G, FIG. 8H, FIG. 8I, FIG. 8J, and FIG. 8K show that MYCBP2 has serine/threonine Ub esterification activity but has preference for threonine, wherein the peptide sequence EGTGN is SEQ ID NO. 5, EGSGN is SEQ ID NO. 6 and EGKGN is SEQ ID NO. 7;

FIG. 9A, FIG. 9B, and FIG. 9C show the E2 requirements of MYCBP2;

FIG. 10A, FIG. 10B, FIG. 10C, FIG. 10D, FIG. 10E, FIG. 10F, and FIG. 10G are structural comparisons and representative stereo views of the $MYCBP2_{cat}$ crystallographic model, wherein the peptide sequences listed in FIG. 10*g* are of SEQ ID NO. 8 to SEQ ID NO. 14, respectively;

FIG. 11A, and FIG. 11B show the crystal structure of $MYCBP2_{cat}$;

FIG. 12A, FIG. 12B, FIG. 12C, FIG. 12D, and FIG. 12E show the structural basis for threonine selectivity, model of an E2-E3 intermediate and model of Ub relay;

FIG. 13A, FIG. 13B, FIG. 13C, FIG. 13D, and FIG. 13E show the modelling of E2-$MYCBP2_{cat}$ complex; and FIG. 14 is a schematic representation for proposed model for RCR E3 ligase mechanism.

FIG. 15 is a Table providing data for $MYCBP2_{4378-4640}$.

DETAILED DESCRIPTION

Introduction

Ubiquitination is initiated by ubiquitin (Ub) transfer from an E1 activating enzyme (E1) to an E2 conjugating enzyme (E2) producing a covalently linked intermediate (E2~Ub)[1]. E3 ligases (E3s) of the Really Interesting New Gene (RING) class recruit E2~Ub via their RING domain and mediate direct transfer of Ub to substrates[2]. Homologous to E6-AP Carboxy Terminus (HECT) E3s undergo a catalytic cysteine-dependent transthiolation reaction with E2~Ub forming a covalent E3~Ub intermediate[3,4]. Additionally, RING-between-RING (RBR) E3s have a canonical RING domain that is linked to an ancillary domain. This contains a catalytic cysteine enabling a hybrid RING/HECT mechanism[5]. Ubiquitination is typically considered a posttranslational modification of lysine residues as human E3s endowed with non-lysine activity remain to be discovered. Herein, we carry out activity-based protein profiling of HECT/RBR-like E3s and uncover the neuron-associated E3 MYCBP2/Phr1 as a novel class of RING-linked E3 with esterification activity and intrinsic selectivity for threonine over serine. MYCBP2 contains two essential catalytic cysteine residues which relay Ub to substrate via thioester intermediates. Crystallographic characterization of this new class of E3 ligase, which we designate as an RING-Cys-Relay (RCR), reveals insights into its mechanism and threonine selectivity. These findings implicate cellular regulation of higher eukaryotes by non-lysine ubiquitination and unappreciated mechanistic diversity of E3 enzymes.

Materials and Methods

General Materials

All DNA constructs were verified by DNA sequencing, (Medical Research Council Protein Phosphorylation and Ubiquitylation Unit, University of Dundee). DNA for bacterial protein expression was transformed into *E. coli* BL21-DE3 (Merck). All cDNA plasmids and antibodies generated for this study are available to request through our reagents website (mrcppureagents.dundee.ac.uk). All solvents and reagents were purchased from Sigma-Aldrich or VWR unless otherwise stated.

Biotin Functionalized ABP Preparation

Figure 3A:
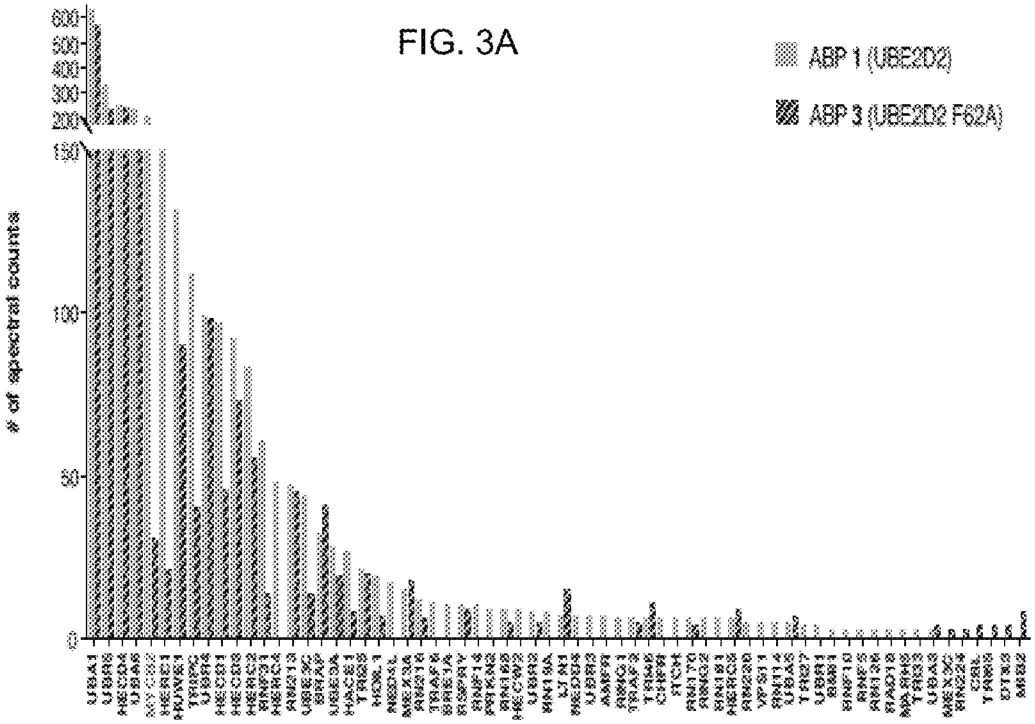
Figure 3B:
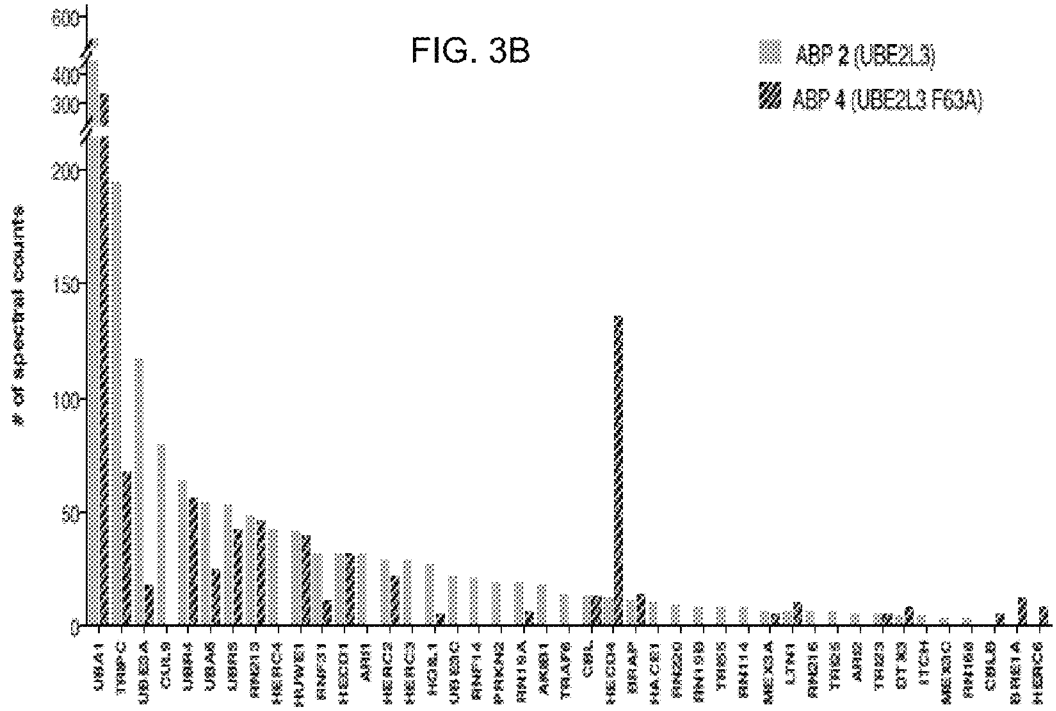
Figure 3C:
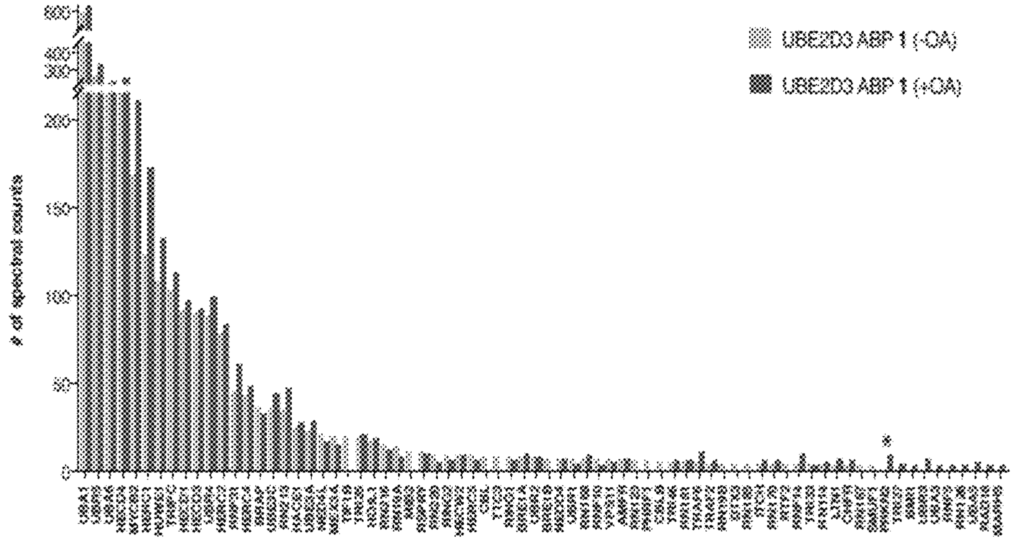
Figure 3D:
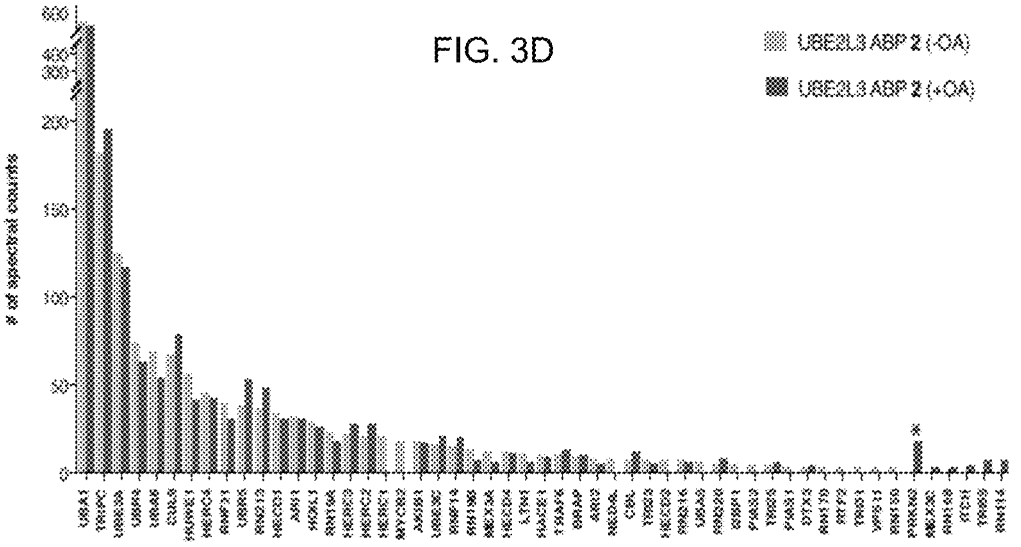

Ub with a GCSSG N-terminal extension was expressed from plasmid pTXB1-UbΔ74-76-T3C plasmid. An equivalent plasmid encoding Ub residues 1-74 (pTXB1-UbΔ75-76-T3C) was also created. Ub thioesters were obtained as described previously generating cysteine tagged Cys-$Ub_{1-73}$-SR and Cys-$Ub_{1-74}$-SR, respectively[7]. The extended $Ub_{1-74}$ was included as this retains Arg74 which forms a favourable electrostatic interaction with the RBR E3 HOIP[31]. Cys-$Ub_{1-73}$-SR (30 mg) was reconstituted by the addition of DMSO (116 µL) followed by $H_2O$ (456 µL). An aqueous stock solution (48 mM) of EZ-link Iodoacetyl-PEG2-biotin (Thermofisher) was prepared and 200 µL was added to the Cys-$Ub_{1-73}$-SR solution (580 µl) followed by the addition of 900 µl degased buffer (50 mM $Na_2HPO_4$ pH 7.5, 150 mM NaCl). The reaction was incubated at 23° C. for 1 hour and monitored by LC-MS. The protein (Biotin-$Ub_{1-73}$-SR) was then further purified by semi-preparative RP-HPLC (Column: BioBasic-4; Part number: 72305-259270). A gradient of 20% buffer A to 50% buffer B was applied at a flow rate of 10 mL $min^{-1}$ over 60 min (buffer A=0.1% TFA in $H_2O$, buffer B=0.1% TFA in acetonitrile). The above procedure was repeated to generate Biotin-$Ub_{1-74}$-SR. HPLC fractions containing Biotin-$Ub_{1-7X}$-SR were pooled and lyophilized (Yield: Biotin-$Ub_{1-73}$-SR 75-85%, Biotin-$Ub_{1-74}$-SR 40-50%) (FIG. 3A and FIG. 3D). Biotin-tagged ABPs containing thioacrylamide warheads were then prepared as previously described[7] employing the E2 recognition elements UBE2D2*, UBE2D2* F62A, UBE2L3* and UBE2L3* F63A furnishing ABPs 1, 3, 2 and 4 (FIG. 3B, FIG. 3C, FIG. 3E, and FIG. 3F). *denotes E2 where non-catalytic Cys residues were mutated to Ser. ABPs based on UBE2D2* and UBE2D3* bearing hexahistidine reporter tags and thioacrylamide warheads (FIG. 5A), were also prepared yielding ABPs 5 and 6, respectively.

Cell Culture and Lysis Protocol

SH-SY5Y cells were cultures as previously described[7]. HEK293 were cultured (37° C., 5% $CO_2$) in Dulbecco's Modified Eagle Medium (DMEM) supplemented with 10% (v/v) Fetal Bovine Serum (FBS), 2.0 mM L-glutamine, and antibiotics (100 units $mL^{-1}$ penicillin, 0.1 mg $mL^{-1}$ streptomycin). Cell transfections were performed using polyethylenimine (Polysciences) according to the manufacturer's instruction. MG-132 (50 µM) was added to cells two hours prior to lysis. Cells were rinsed with ice-cold PBS and extracted in lysis buffer (1% NP-40, 50 mM Tris-HCl pH 7.5, 1.0 mM EGTA, 1.0 mM EDTA, 0.27 M sucrose, 10 mM sodium 2-glycerophosphate, 0.2 mM phenylmethane sulfonyl fluoride (PMSF), 1.0 mM benzamidine, 1.0 mM sodium ortho-vanadate, 50 mM sodium fluoride and 5.0 mM sodium pyrophosphate, 50 mM iodoacetamide and cOmplete™, EDTA-free protease inhibitor cocktail (Roche)). Lysates were then clarified by centrifugation at 4° C. for 30 min at 14,800 rpm. Supernatants were collected (total cell extracts) and protein concentration determined by Bradford assay. For the base-lability test, indicated cell lysates were further incubated with 0.5M hydroxylamine, pH 9.0 at 37° C. for 30 minutes.

Immunoblotting

Samples were mixed with NuPAGE LDS sample buffer (Thermofisher) without boiling, and resolved by SDS-PAGE (4-12% NuPage gel, Thermofisher) with MOPS or MES running buffer and transferred on to 0.45 μm nitrocellulose membranes (GE Life Sciences). Membranes were blocked with PBS-T buffer (PBS+0.1% Tween-20) containing 5% (w/v) non-fat dried skimmed milk powder (PBS-TM) at room temperature for 1 h. Membranes were subsequently probed with the indicated antibodies in PBS-T containing 5% (w/v) Bovine Serum Albumin (BSA) overnight at 4° C. Detection was performed using HRP-conjugated secondary antibodies in PBS-TM for 1 h at 23° C. ECL western blotting detecting reagent (GE Life Sciences) was used for visualization in accordance with the manufacturers protocol.

Antibodies

His-tagged species were probed with 1:10000 anti-His primary antibody (Clontech, #631212). Alpha tubulin (1E4C11) mouse mAb (Proteintech®) was used at 1:10000 dilution. The MYCBP2 antibody was used at 0.5 μg $mL^{-1}$ and raised by in sheep by MRC PPU Reagents and Services and affinity-purified against the indicated antigen: anti-MYCBP2 (2nd bleed of SA357, residues 4378-4640 of human MYCBP2). Mouse monoclonal NMNAT2 antibody (clone 2E4; Sigma Aldrich) was used at 0.5 μg $mL^{-1}$.

Activity-Based Proteomic Profiling of SH-SY5Y Cells

SH-SY5Y total cell lysate (4.5 mg, 550 μL) was mixed with ABPs 1, 2, 3 and 4 (3 μM) and incubated at 30° C. for 4 hours. To induce Parkin activation cells were administered with oligomycin (5 μM) and antimycin A (10 μM) (OA) for 3 hours. Control enrichments were also performed where probe was withheld. Extracts were mixed with 100 μL of Pierce™ Streptavidin Plus UltraLink™ Resin (ThermoFisher Scientific) and diluted with 6% SDS solution (20 μL) to a final concentration of 0.2% in phosphate buffer. Samples were incubated for 4 hours at 4° C. and resin washed (2 ml 0.2% SDS/PBS, 2 ml PBS, 1 ml 4 M urea/PBS, 2 ml PBS) and then resuspended in 190 μl Tris buffer (50 mM Tris pH 8, 1.5 M urea). Resin-bound proteins were reduced with TCEP (5 mM) for 30 minutes at 37° C. and then alkylated with iodoacetamide (10 mM) at 23° C. for 20 minutes. DTT (10 mM) was then added followed by washing with buffer (50 mM Tris pH 8, 1.5 M urea) to a final volume of 300 μL. Trypsin (2 μg) was then added and further incubated at 37° C. for 14 hours. Trifluoroacetic acid was added to a final concentration of 0.1% and samples were desalted with a $C^{18}$ MacroSpin column (The Nest Group Inc). LC-MS/MS analysis was performed on an LTQ Orbitrap Velos instrument (Thermo Scientific) coupled to an Ultimate nanoflow HPLC system (Dionex). A gradient running from 3% solvent B to 99% solvent B over 345 min was applied (solvent A=0.1% formic acid and 3% DMSO in $H_2O$; solvent B=0.08% formic acid and 3% DMSO in 80% MeCN).

Data Processing

Raw files were searched against the Swissprot database and a decoy database using the MASCOT server (Matrix Science). Trypsin specificity with up to three missed cleavages was applied. Cysteine carbamylation was set as a fixed modification and variable modifications were methione oxidation/dioxidation. A PERL script was used to extract the number of rank 1 peptides for each protein from the MASCOT search results and this figure was used as the number of spectral counts. A second PERL script filtered the data by searching the human swisspfam_v30 database using the E3 domain terms RING, HECT, IBR and zf-UBR. Manual curation was also carried out which involved the addition of E1 enzymes. Any proteins with less than 3 spectral counts and less than 14-fold spectral count enrichment, relative to control experiments where ABP was withheld, were omitted from the list. Pairwise datasets were then plotted as column charts in Prism (Graphpad Software).

Cloning of $MYCBP2_{cat}$

Human MYCBP2 (NM_015057.4) sequences were amplified from full-length Addgene plasmid #2570. Wild type and mutant fragments were subcloned as BamHI/Not1 inserts into pGEX6P-1 (GE Life Sciences) for bacterial expression, or a modified version of pcDNA TM5/FRT/TO (ThermoFisher) containing an N-terminal Myc tag for mammalian expression.

UBE1 and E2 Expression and Purification

6His-UBE1 was expressed in Sf21 cells and purified via its tag as previously described[32]. Phosphate Buffered Saline was used throughout the purification and hydroxy containing compounds avoided. UBE2D3 was expressed as an N-terminally 6His-tagged protein in BL21 cells and purified over Ni-NTA-agarose and finally dialysed into 50 mM $Na_2HPO_4$ pH 7.5, 150 mM NaCl, 0.5 mM TCEP. UBE2A was expressed as a GST-fusion in *E. coli* and the GST tag was proteolytically removed. The remaining E2s were expressed as recombinant bacterial proteins and purified via their His-tags and buffer exchanged by size exclusion chromatography into running buffer (50 mM $Na_2HPO_4$ pH 7.5, 150 mM NaCl, 0.5 mM TCEP, 0.015% Brij-35) using a Superdex 75 column (GE Life Sciences).

Expression and Purification of MYCBP2 and GST-MYCBP2

GST-tagged $MYCBP2_{cat}$ (Ser4378-Phe4640), wt and mutants, were expressed at 16° C. overnight and purified against glutathione resin (Expedeon) using standard procedures. GST-tagged constructs were eluted with glutathione and untagged constructs were obtained by on-resin cleavage with Rhinovirus 3C protease. Proteins were buffer exchanged into 50 mM Tris-HCl pH 7.5, 150 mM NaCl, 1.0 mM TCEP buffer and flash frozen for storage at −80° C.

Expression and Purification of NMNAT2

NMNAT2 was expressed with a 6His-SUMO tag in BL21(DE3) cells, induced with 0.1 mM IPTG and incubated for expression at 16° C. The cells were collected and lysed in buffer (50 mM Tris-HCl (pH 7.5), 250 mM NaCl, 0.2 mM EGTA, 20 mM imidazole, 20 mM L-arginine, 0.015% Brij 35, 1 mM Leupeptin, 1 mM Pefabloc, 1 mM DTT using standard protocols and the protein was purified over Ni-NTA-agarose. The eluted protein was incubated with His-SENP1 protease during dialysis against PBS, 20 mM L-arginine, 1 mM DTT. The tag and protease were depeleted against Ni-NTA-agarose and NMNAT2 was concentrated and subjected to chromatography on a Superdex 75 HR 10/30 into buffer (PBS, 20 mM L-arginine).

Activity-Based Protein Profiling of MYCBP2 Cysteine Mutants

The indicated MYCBP2 mutant was diluted into Tris buffer (50 mM Tris-HCl pH 7.5, 150 mM NaCl) to a final concentration of 3 μM. Probe 6 was added (12 μM) and incubated with E3 ligase at 30° C. for four hours. Reactions were quenched by the addition of 4×LDS loading buffer (supplemented with ~680 mM 2-mercaptoethanol) and samples were resolved by SDS-PAGE (4-12% NuPage gel) followed by Coomassie staining or anti-His immunoblotting.

Tryptic MS/MS Sequencing of Probe-Labelled MYCBP2

Crosslinking MS using ABP 6 was carried out as previously described[7]. In summary Coomassie stained SDS-PAGE band corresponding to ABP-labelled WT MYCBP2 was analyzed by LC-MS/MS using an Orbitrap Fusion™ Tribrid™ mass spectrometer (Thermo Scientific) coupled to an Ultimate nanoflow HPLC system (Dionex). A gradient running from 0% solvent A to 60% solvent B over 120 min was applied (solvent A=0.1% formic acid in $H_2O$; solvent B=0.08% formic acid in 80% MeCN). Fragment Ions were generated by HCD and $1^+$, $2^+$ and $3^+$ precursor ions excluded. Raw data was searched using the pLink software[33] against UBE2D3* and MYCBP2 sequences with trypsin specificity (up to 2 missed cleavages). The error window for MS/MS fragment ion mass values was set to the software default of 20 ppm. A crosslinker monoisotopic mass of 306.1805 Da was manually added which accounted for the theoretical mass difference associated with formation of a bisthioether between 2 Cys residues derived from probe 6, which was based on UBE2D3* and contained a thioacrylamide AVS warhead[7].

Tris/Glycerol-Mediated E2 Discharge Assay

Assays were carried out in buffer (50 mM Tris-HCl pH 7.5, 150 mM NaCl, 0.5 mM TCEP, 5 mM $MgCl_2$) containing the indicated MYCBP2 mutant (15 μM), UBE1 (1.5 μM), UBE2D3 (15 μM), Ub (37 μM) and ATP (10 mM). The reactions were incubated at 37° C. for 30 minutes. Reactions were terminated by the addition of 4×LDS loading buffer (with and without ~680 mM 2-mercaptoethanol). A C4572S sample was further incubated with 0.14 N NaOH at 37° C. for 20 minutes and samples were resolved by SDS-PAGE (4-12% NuPage gel) and visualized by Coomassie staining.

LC-MS Analysis of Nucleophile Discharge Assays

Reactions were prepared as described for discharge assay. After 30 minutes, the reaction was analyzed using an Agilent 1200/6130 LC-MS system (Agilent Technologies) using a 10-75% gradient over 20 minutes (buffer A=$H_2O$+0.05% TFA, buffer B=acetonitrile+0.04% TFA).

Preparation of Cy3b-Ub

Ub bearing a TEV protease-cleavable N-terminal hexahistidine tag followed by a ACG motif was expressed in bacteria from a pET plasmid (kindly provide Ronald Hay, University of Dundee). Protein was purified by Ni affinity chromatography, cleaved from the tag with TEV protease then buffer exchanged into reaction buffer (50 mM HEPES, pH 7.5, 0.5 mM TCEP). Protein was concentrated to 2 mg $mL^{-1}$ and 221 μL (50 nmol) was mixed with Cy3b-maleimide (150 nmol, GE Life Sciences) in a final volume of 300 μL and agitated for 2 h at 25° C. Labelled protein was then further purified with a P2 Centri-Pure desalting column (EMP Biotech) with degassed buffer (50 mM $Na_2HPO_4$, 150 mM NaCl).

MYCBP2 Thioester/Ester Trapping Assay

Figure 2A:
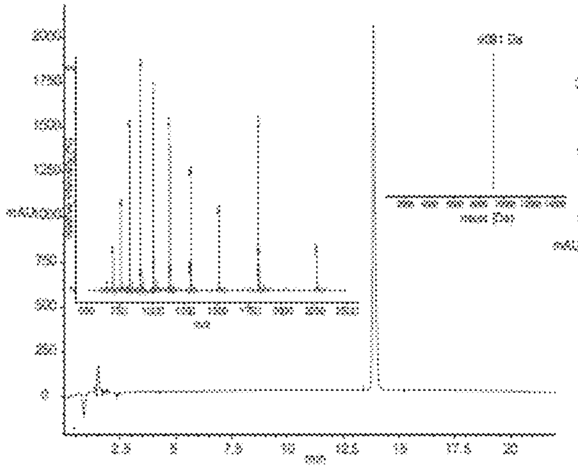
Figure 2B:
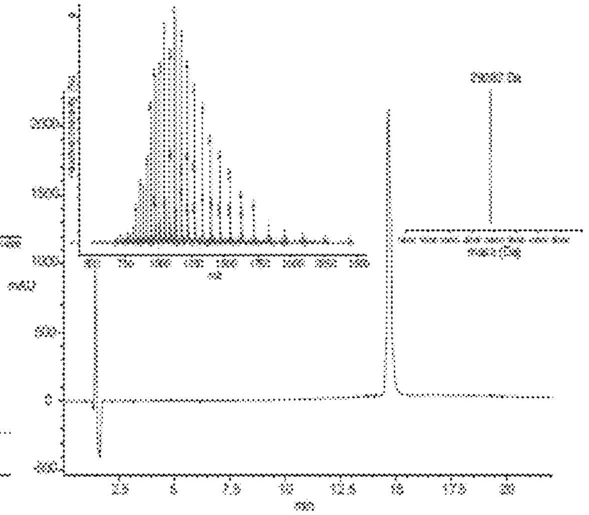
Figure 2C:
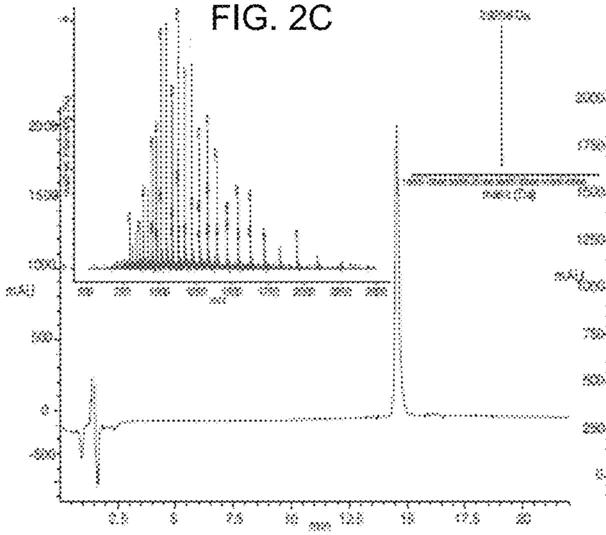
Figure 2D:
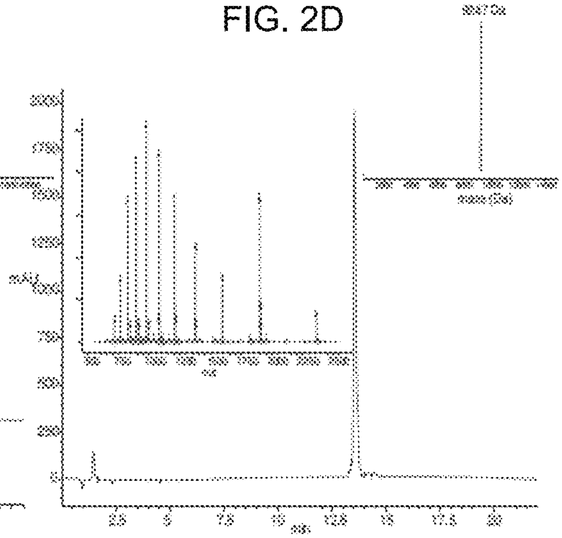
Figure 2E:
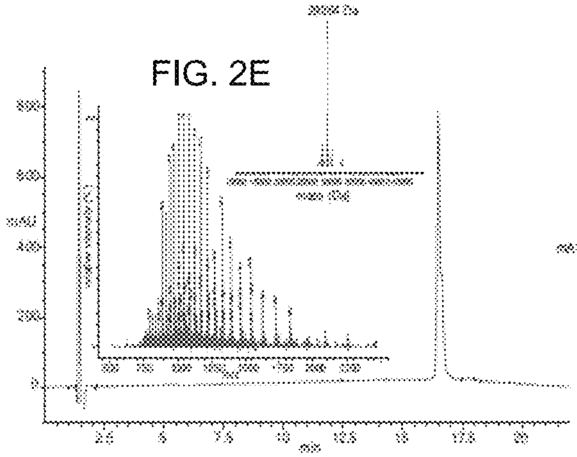
Figure 2F:
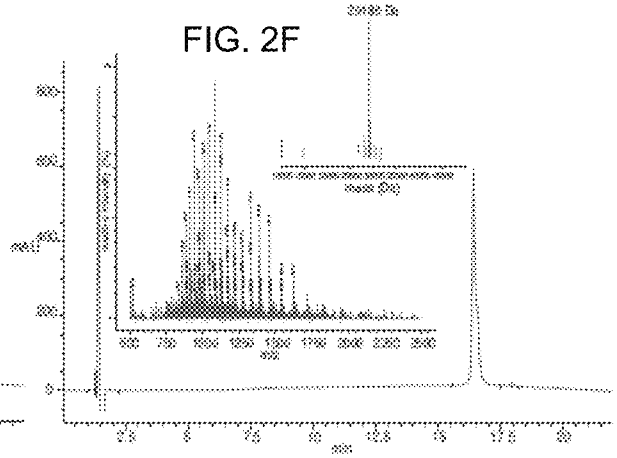

UBE1 (2 μM) was mixed with Cy3b-Ub (1 μM) in buffer (40 mM $Na_2HPO_4$—HCl pH 7.5, 150 mM NaCl, 0.5 mM TCEP, 5 mM $MgCl_2$) (FIG. 2E, lanes 1 and 2). The reaction was then initiated by the addition of ATP (5 mM) and incubated for 10 minutes at 25° C. Samples (lane 3, 4) were taken and combined with UBE2D3 (10 μM). After a further 10 minutes at 25° C., samples (lane 5, 6) were taken and combined with GST-MYCBP2$_{cat}$ (WT, C4520S, C4520A, C4572S, C4572A, C4520A/C4572S or C4520S/C4572A) (15 μM). The reactions were incubated at 25° C. for 30 seconds and terminated by the addition of 4×LDS loading buffer (either non-reducing or reducing). For Ub~GST-MYCBP2$_{cat}$ C4572S ester bond cleavage, 0.14 N NaOH was added after E3 reaction with E1/E2 mixture for 30 seconds and then further incubated at 37° C. for 20 minutes. The gel was then scanned with a Chemidoc Gel Imaging System (BioRad).

Multiple Turnover Amino Acid and Peptide Panel Discharge Assays

Stock solutions (0.5 M) of amino acids were dissolved in MQ water and pH was adjusted to pH ~8. Peptides of the sequence Ac-EGXGN-$NH_2$ (X=K, S or T) were obtained from Bio-Synthesis Inc. Stock peptide solutions (200 mM) were dissolved in MQ water and pH was adjusted to pH ~8. An E2 (UBE2D3) charging reaction was carried out in buffer (40 mM $Na_2HPO_4$—HCl pH 8.0, 150 mM NaCl, 0.5 mM TCEP) containing UBE1 (250-500 nM), UBE2D3 (20 μM), Ub (50 μM), or Cy3B-Ub (25 μM), $MgCl_2$ (5 mM) and ATP 10 (mM). The reaction was incubated at 37° C. for 15 minutes and then equilibrated to 23° C. for 3 minutes. An equivalent volume of nucleophile sample containing small molecule/peptide nucleophile (100 mM) and GST-MYCBP2 (10 μM) was then added and incubated at 23° C. Samples were taken at the specified time points and analyzed as described for Tris/glycerol-mediated E2 discharge assay.

Cy3B-Ub was visualized using a Chemidoc Gel Imaging System (Biorad). LC-MS was carried out as described for Tris/glycerol discharge but amino acid substrate samples were quenched by the addition of 2:1 parts quenching solution (75% acetonitrile, 2% TFA) and peptide substrate samples were quenched by addition of 1:1 parts quenching solution.

Multiple Turnover E2 Discharge Panel

E2s were screened for threonine discharge activity with GST-MYCBP2$_{cat}$ as described for the amino acid panel. E2s were also incubated in the presence of threonine but in the absence of GST-MYCBP2$_{cat}$. These samples provided a reference to distinguish between intrinsic E2~Ub instability and E3-dependent discharge.

Single Turnover E2 Mutant Discharge by in-Gel Fluorescence

E2 mutants[16,17,34-36] (10 μM) were charged with Cy3b-labelled Ub (12.5 μM) in a final volume of 12 μL at 37° C. for 20 minutes then cooled at 23° C. for 3 minutes. E2 recharging was then blocked by the addition of MLN4924 derivative, Compound 1 (25 μM)[37], which inhibits E1, and then incubated for a further 15 minutes. The mixture was then mixed with 12 μL of GST-MYCBP2$_{cat}$ (5 μM) and threonine (100 mM) and incubated at 23° C. for the specified time. Analysis was carried out as for multiple turnover assays. To account for intrinsic E2~Ub instability the mean % discharge (n=2) calculated against a parallel incubation where E3 was withheld. Data were plotted using Prism (Graphpad).

Expression and Purification of ARIH1 and UBE3C

ARIH1 residues 1-394 (Dundee clone DU24260) was expressed as an N-terminally GST-tagged fusion protein in BL21 cells. UBE3C residues 641-1083 (Dundee Clone DU45301) was expressed as a N-terminally GST-tagged fusion protein in Sf21 cells using the baculovirus infection system.

Calculation of Observed Rate Constants for E3-Substrate Dependent Single Turnover E2~Ub Discharge UBE2D3 or UBE2L3 (5 μM) were charged with Cy3b-labelled Ub (8 μM) in a final volume of 30 μL at 37° C. for 25 minutes then incubated at 23° C. for 3 minutes. Single turnover conditions for E2~Ub discharge were achieved by E1 inhibition with MLN4924 derivative, Compound 1 (25 μM) and then incubated for a further 15 minutes. The mixture was then mixed with 30 μL of MYCBP2$_{cat}$ or ARIH1$_{1-394}$ (HHARI) or UBE3C$_{641-1083}$ (1 μM) and threonine (100 mM) and incubated at 23° C. for the specified time. Samples were quenched with non-reducing 4×LDS loading buffer and resolved by SDS-PAGE (Bis-Tris 4-12%). The gel was then scanned with a Chemidoc Gel Imaging System (BioRad) and subsequently Coomassie stained. E2~Ub signals were quantified using the Fiji software. Observed rate constants were obtained by fitting reaction progressive curves to a single exponential function using Prism (Graphpad Software).

MYCBP2 Crystallization

MYCBP2 was expressed as described for untagged protein. After protease cleavage of the tag the protein was further purified by size exclusion chromatography using an ÄKTA FPLC system and a HiLoad 26/600 Superdex 75 μg column (GE Life Sciences). The running buffer consisted of 20 mM HEPES pH 7.4, 150 mM NaCl, 4 mM DTT. Combined fractions were concentrated to 10.4 mg $mL^{-1}$. Sparse matrix screening was carried out and Bipyrimidal crystals were obtained from the Morpheus screen condition C1 (Molecular Dimensions). A subsequent optimization screen yielded multiple crystals (Buffer system 1 (MES/imidazole) pH 6.7, 23.3 mM $Na_2HPO_4$, 23.3 mM $(NH_4)_2SO_4$, 23.3 mM $NaNO_3$, 18% PEG500 MME, 9% PEG20000). A single crystal was soaked in mother liquor and further cryoprotected by supplementation with 5% PEG400 and frozen in liquid $N_2$. Data were collected to 1.75 Å at the European Synchrotron Radiation Facility at Beamline ID23-1. Energy was set to the peak value of 9.669 keV (1.2823 Å), as determined by an absorption edge energy scan. A total of 360° were collected with an oscillation range of Ω=0.1°. The phase problem was solved by locating 6 $Zn^{2+}$ sites in the anomalous signal and solvent flattening with the SHELX suite. An initial model was built by ARP/wARP[38] and subsequently optimized by manual building in COOT[39] and refinement with REFMAC5[40] resulting in the final model with statistics as shown in FIG. 10. Final Ramachandran statistics were favored: 95.55%, allowed: 3.24%, outliers: 1.21%.

Size Exclusion Chromatography with Multi-Angle Light Scattering (SEC-MALS)

SEC-MALS experiments were performed on a Ultimate 3000 HPLC system (Dionex) with an in-line miniDAWN TREOS MALS detector and Optilab T-rEX refractive index detector (Wyatt). In addition, the elution profile of the protein was also monitored by UV absorbance at 280 nm. A Superdex 75 10/300 GL column (GE Life Sciences) was used. Buffer conditions were 50 mM $Na_2HPO_4$ pH 7.5, NaCl 150 mM, 1.0 mM TCEP and a flow rate of 0.3 mL $min^{-1}$ was applied. Sample (50 μL, 5.5 mg $mL^{-1}$) was loaded onto the column with a Dionex autosampler. Molar masses spanning elution peaks were calculated using ASTRA software v6.0.0.108 (Wyatt).

Mediator Loop Modelling

Mediator loop residues where built and geometry optimized within the Bioluminate Software (Schrödinger). Side chains were modified within COOT[39] and figures were generated with Pymol (Schrödinger). Ramachandran analysis was carried with the RAMPAGE server[41].

NMNAT2 Ubiquitination Assay

NMNAT2 (5 μM) was mixed with E1 (500 nM), UBE2D3 (10 μM), $MYCBP2_{cat}$ (10 μM), Ub (50 μM), ATP (10 mM) and made up with 10×pH 7.5 buffer (40 mM $Na_2H_2PO_4$ pH 7.5, 150 mM NaCl, 5 mM $MgCl_2$, 0.5 mM TCEP). The reactions were incubated at 37° C. for 1 hour and terminated by the addition of 4×LDS loading buffer (either non-reducing or reducing). For base lability test, reactions were supplemented with 0.14 N NaOH and then further incubated at 37° C. for 20 minutes.

Bioinformatic Analysis

Proteins belonging to the RCR family were identified by generalized profile searches. Overall 671 such sequences were identified. The sequences were aligned by profile-guided alignment using the pftools package. For identifying representative sequences from various taxa, the Belvu program (Sanger Institute) was used to remove sequences with >80% identity to other sequences. Truncated and misassembled proteins were removed manually, resulting in 130 representative TC domain sequences.

Data Availability Statement

Coordinates have been deposited with the Protein Data Bank (PDB ID 5O6C).

Results

Figures 1A, 1B:
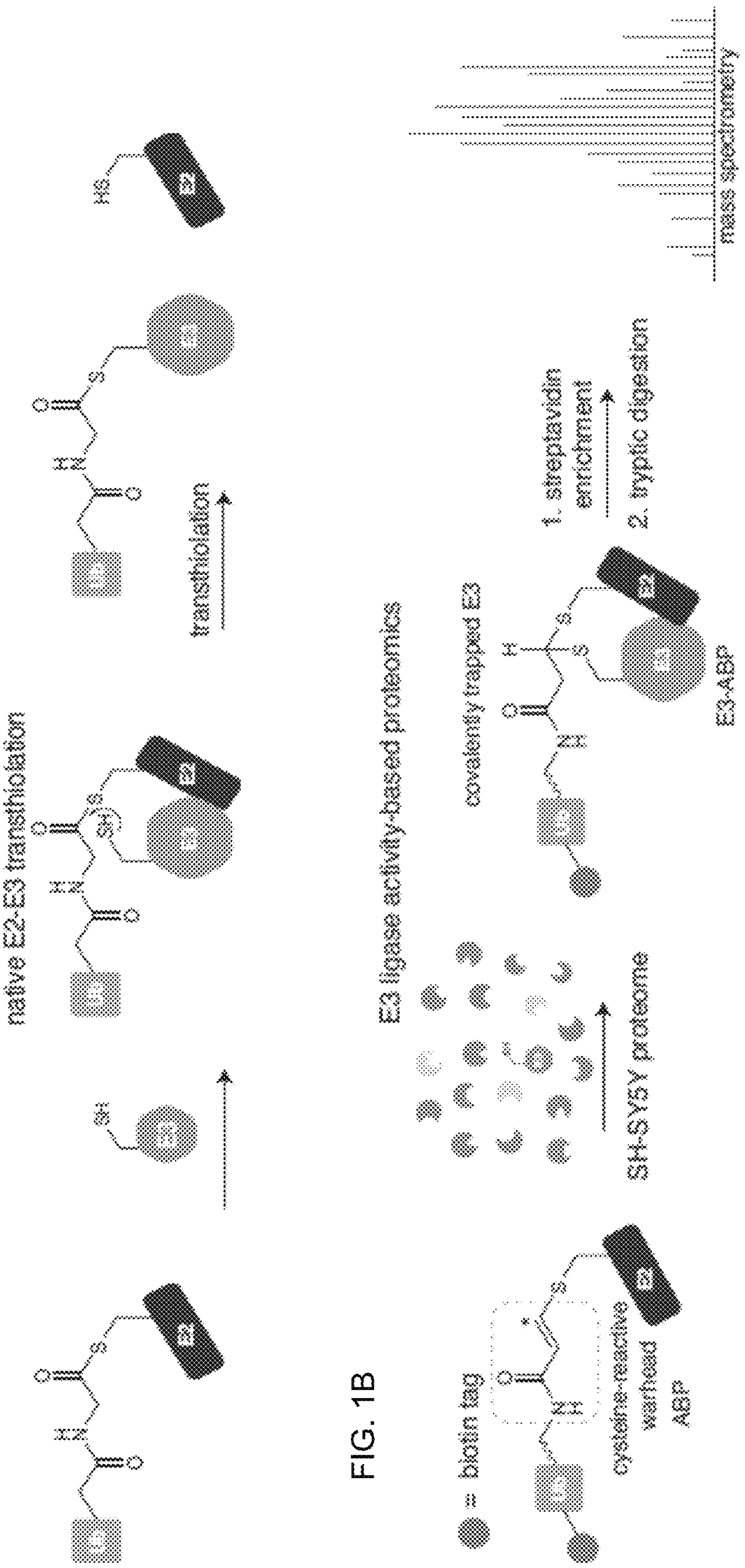
Figure 1C:
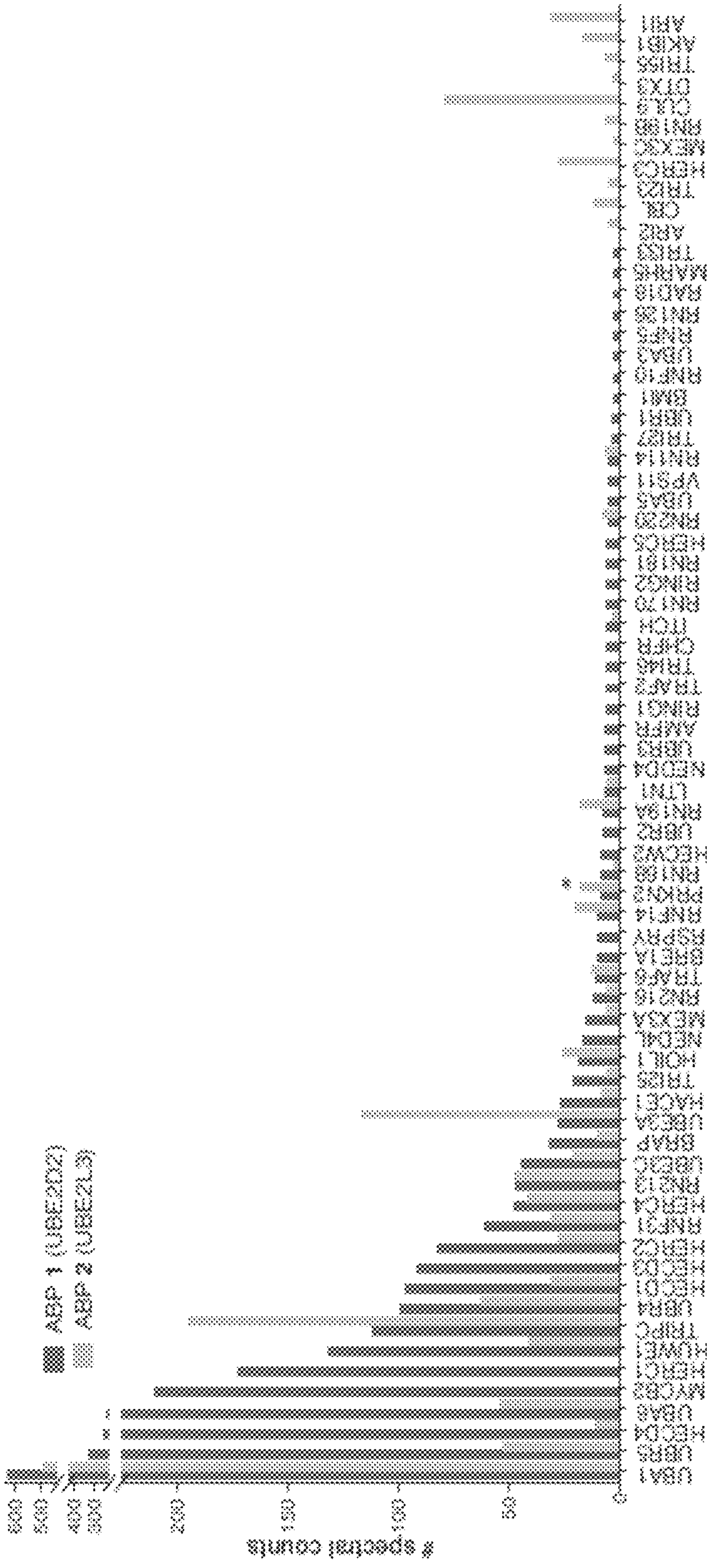

We prepared biotinylated variants of our recently developed activity-based probes (ABPs)[6] which profile the hallmark transthiolation activity of HECT/RBR E3s (FIG. 1A and FIG. 2)[7]. Interfacing the ABP technology with mass spectrometry enabled parallelized profiling of E3 activity in neuroblastoma SH-SY5Y cell extracts[8,9] (FIG. 1B). E3s were filtered using criteria ensuring signals for at least a subset of detected E3s correlated with E3 activity and/or abundance (FIG. 3). Profiling of ~80% of the ~50 known HECT/RBR E3s was achieved but unexpectedly, 33 RING E3s, devoid of HECT or RBR ancillary domains, were also enriched (FIG. 1C through FIG. 1E). To explore the possibility that hitherto undiscovered RING-linked E3s were being labelled we focused on MYCBP2/Phr1 (Myc-binding protein 2; PAM/Highwire/Rpm-1) (FIG. 1C). MYCBP2 is a large 0.5 MDa neuron-associated protein which contains a C-terminal RING domain (FIG. 4A), and is involved in a range of cellular processes including regulation of nervous system development and axon degeneration[10-12].

Figure 4A:
Figure 4B:
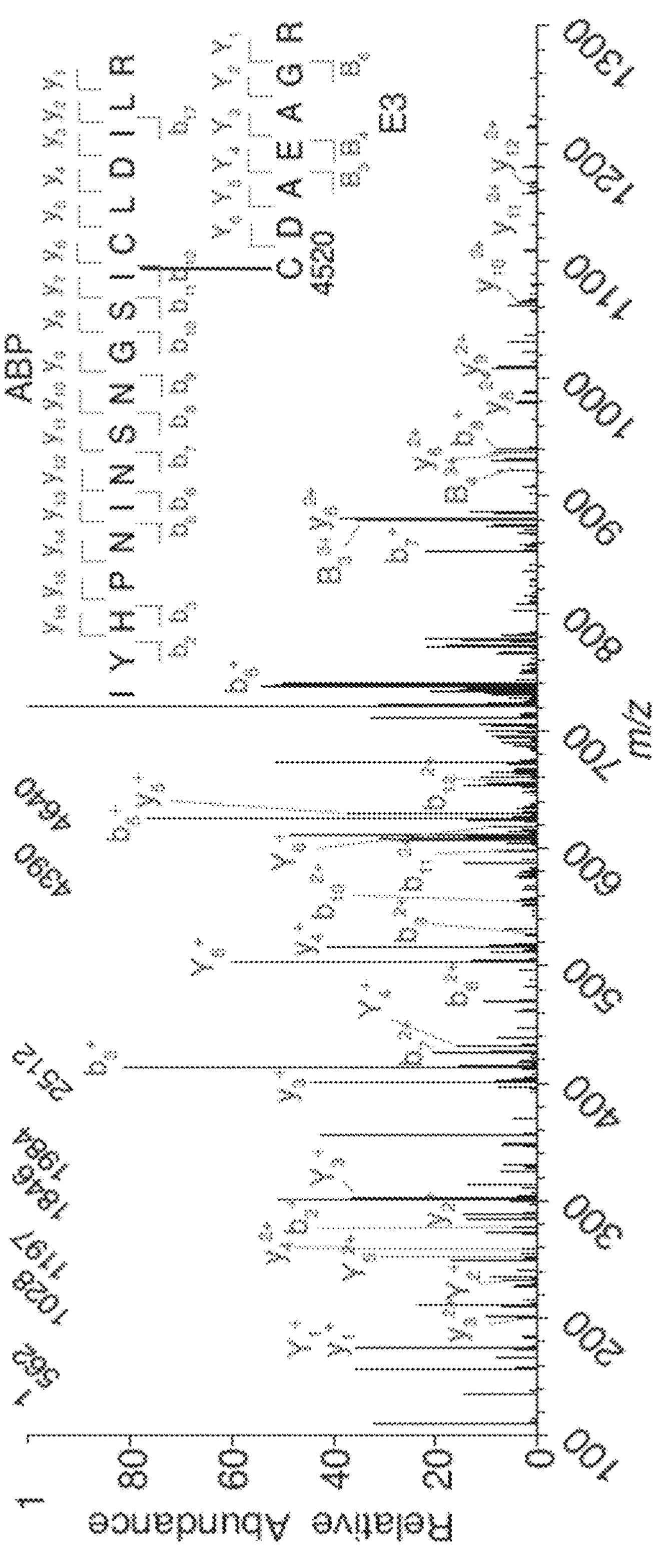
Figures 4C, 4D, 4E:
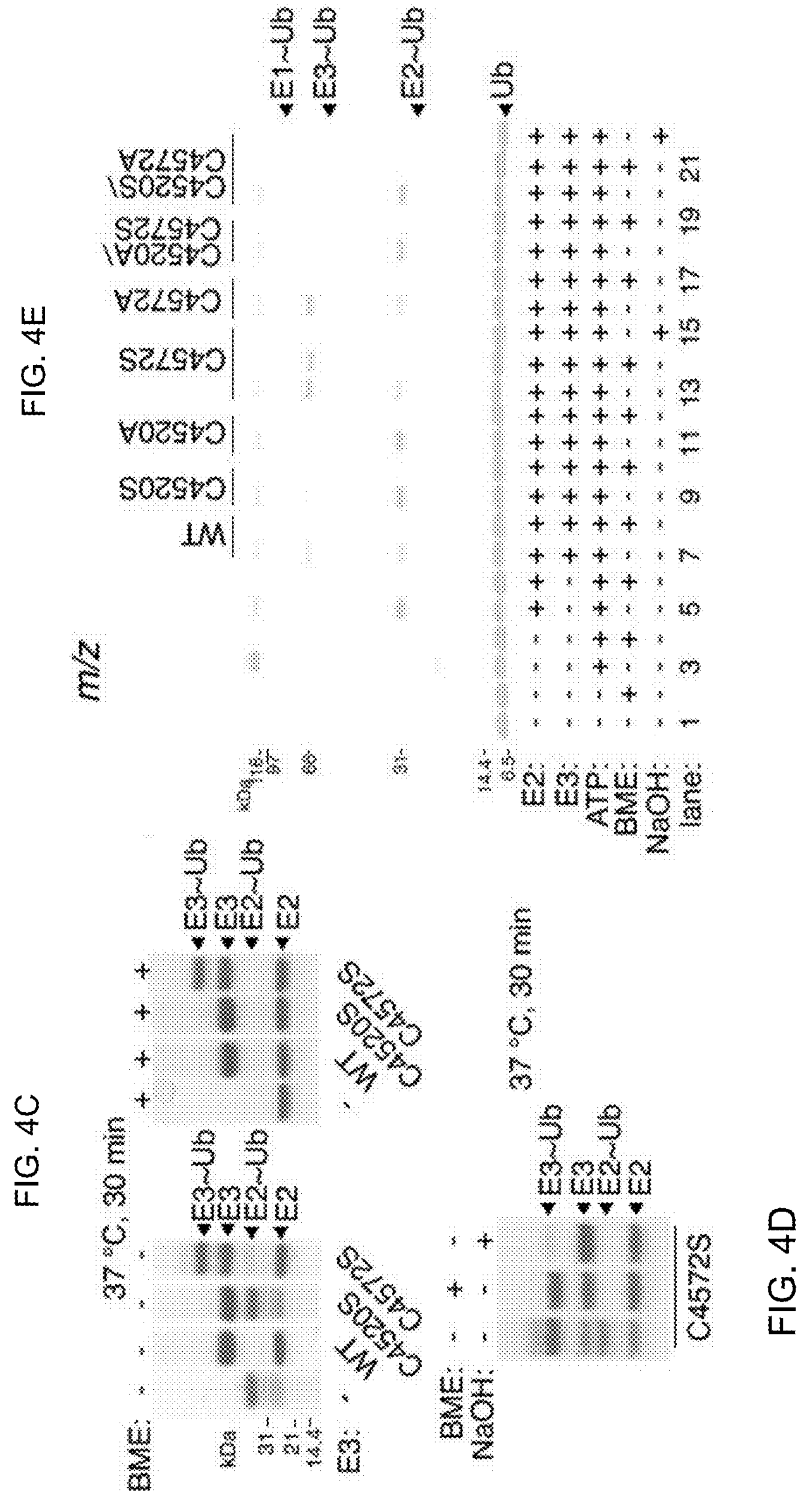
Figure 5A:
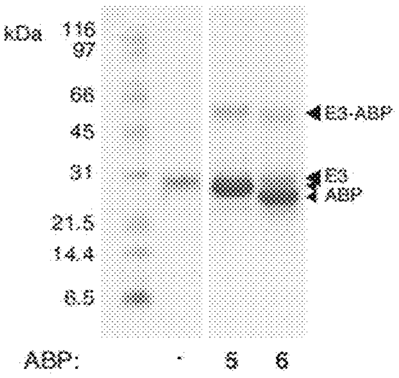
Figure 5B:
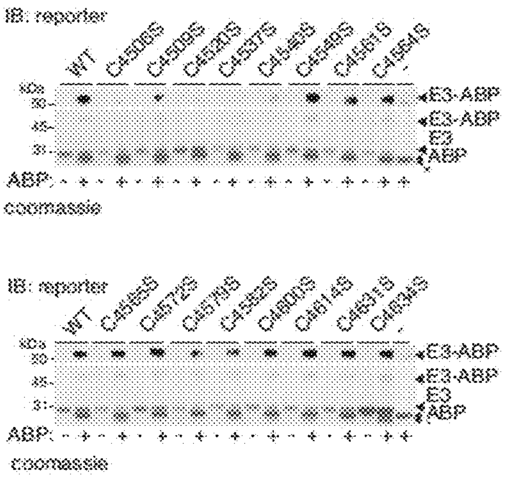
Figure 5C:
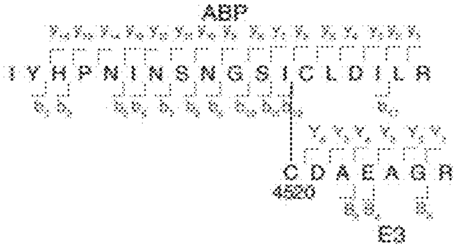
Figures 9A, 9B, 9C:
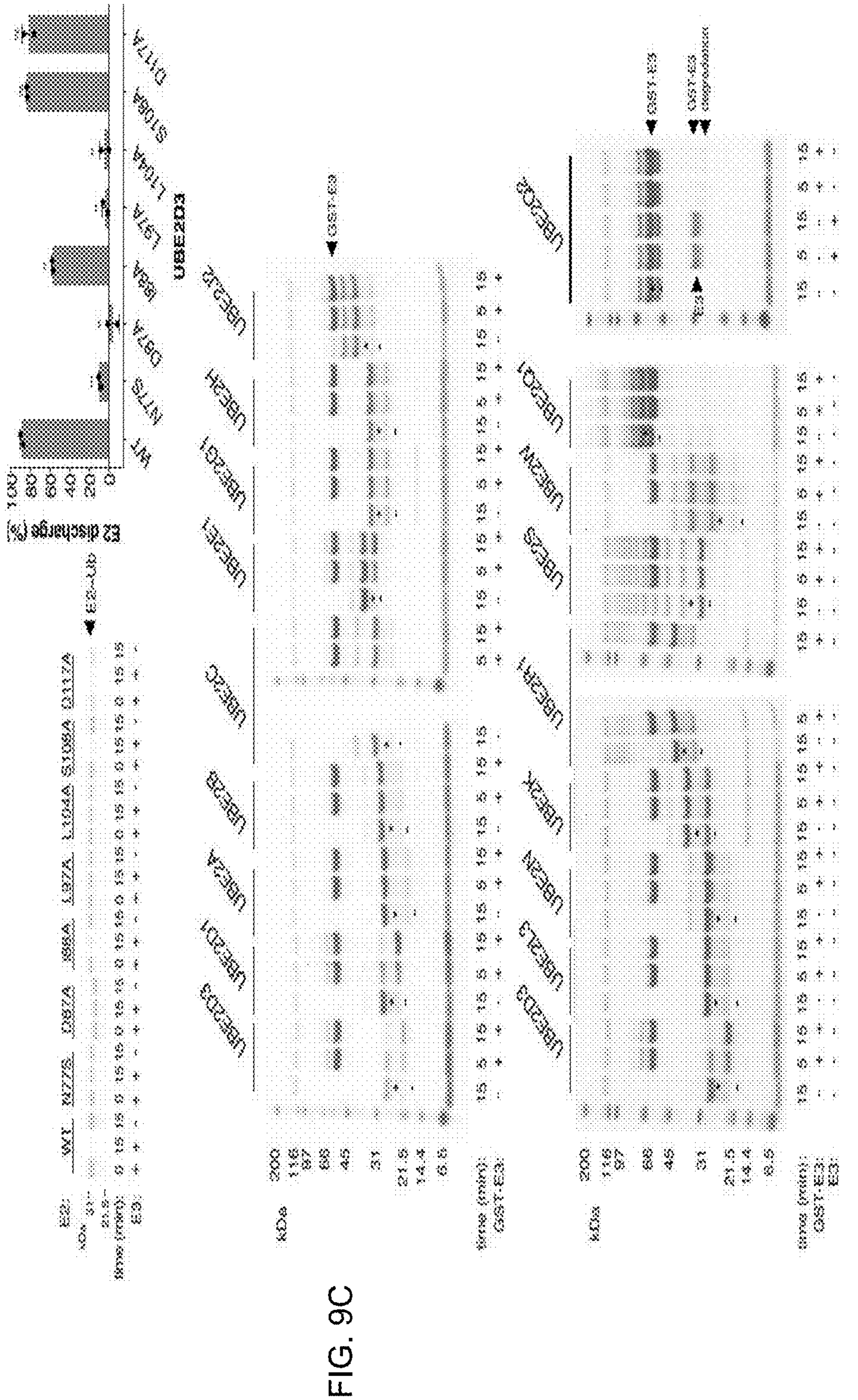

A recombinant C-terminal version of MYCBP2 encompassing the RING domain (residues 4378-4640; $MYCBP2_{cat}$; FIG. 4A) and an uncharacterized C-terminal cysteine-rich region underwent robust ABP labelling with an efficiency comparable to that of E3s known to demonstrate transthiolation activity[7,13] (FIG. 5A). To map the putative catalytic cysteine we used a combination of ABP-based profiling and ABP-crosslinking MS[7] (FIG. 2B, FIG. 5B, and FIG. 5C). Data were in support of C4520 being a putative catalytic residue. We next assayed wild type (WT) E3 activity but were unable to detect autoubiquitination or free Ub chain formation. However, we observed rapid E3-dependent discharge of Ub from E2~Ub suggestive of the presence of an unknown small molecule nucleophilic acceptor (FIG. 2C). Liquid chromatography-mass spectrometry (LC-MS) analysis revealed that Ub was being quantitatively converted into two species with masses corresponding to condensation products with tris(hydroxymethyl)aminomethane (Tris) and glycerol (8639 and 8668 Da), both of which were present in our assay buffer at routinely employed concentrations of 50 mM and ~65 mM, respectively. Due to the common hydroxy functionality within these nucleophiles, MYCBP2 appeared to have esterification activity (FIG. 9A and FIG. 9B). Activity was found to be dependent on C4520, consistent with it forming a thioester-linked E3'~Ub intermediate[4,5] (FIG. 4C).

Figure 6A:
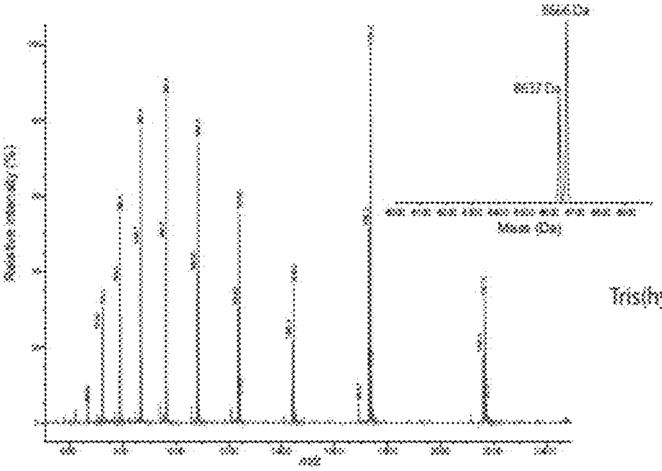
Figure 6B:
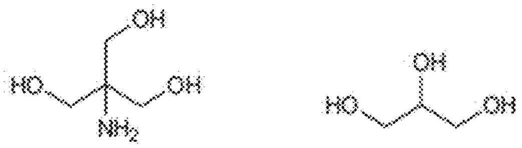
Figure 6C:
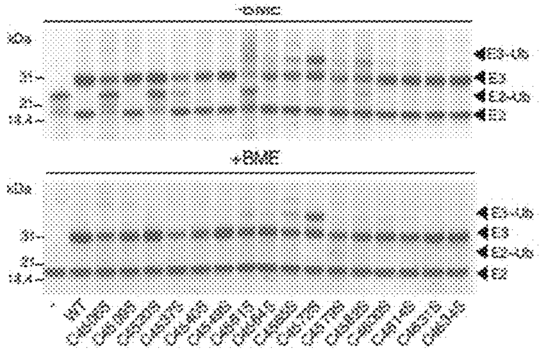
Figure 6D:
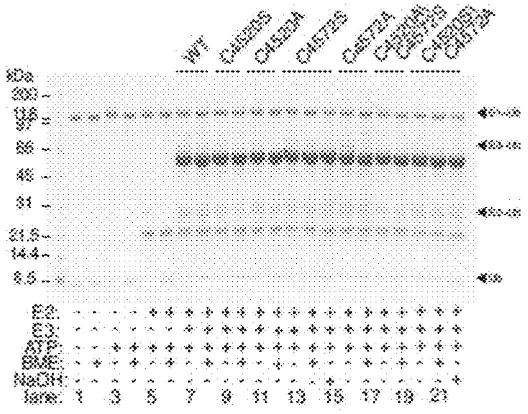
Figure 6E:
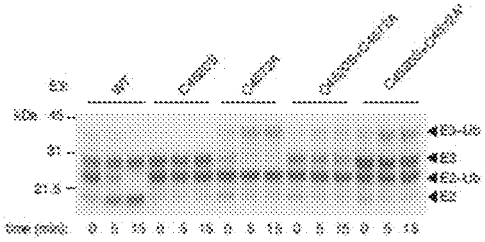
Figure 6F:
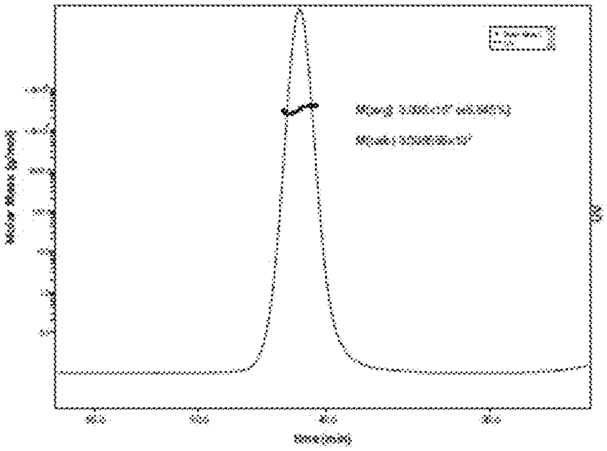

Unexpectedly, a MYCBP2 C4572S mutant retained activity yet formed a discrete mono Ub adduct that was resistant to thiolysis but reversible after base treatment (FIG. 4C, FIG. 4D, and FIG. 6C)[5]. A possibility was the mutated S4572 residue was contributing to catalysis via formation of a less transient (oxy)ester-linked intermediate between Ub and S4572 that retained the ability to modify substrate. We hypothesized that C4520 and C4572 were both catalytic residues that functioned in tandem by relaying Ub from one cysteine to the other through an intramolecular transthiolation reaction. To test this relay mechanism, we carried out gel-based thioester/ester trapping assays[14] (FIG. 4E and FIG. 6D) and observed a thiol-sensitive Ub adduct on WT MYCBP2$_{cat}$ which was not observed with the C4520S mutant (FIG. 4E). Consistent with earlier experiments (FIG. 4C), C4572S underwent adduct formation that was thiol-resistant but base labile (FIG. 4E). Thus, if a transient thioester intermediate was being formed between Ub and C4520, then an unreactive C4572A mutant should stabilize it. Indeed, thiol-sensitive adduct formation was increased on a C4572A mutant relative to that of the wild type and was presumably linked via a thioester bond (FIG. 4E). Adduct formation was not detected with a C4520A/C4572S double mutant in support of it being linked to the C4520 residue (FIG. 4E). In the absence of direct demonstration of Cys-to-Cys Ub transfer we cannot formally exclude other possibilities. However, the existing data are consistent with the essential cysteines functioning in a relay mechanism. Mutational analysis and size exclusion chromatography-multi angle light scattering (SEC-MALS) of MYCBP2$_{cat}$ (FIG. 6E and FIG. 6F) suggests the proposed relay mechanism requires both essential cysteines be in the same molecule, consistent with an intramolecular relay mechanism.

Figures 7A, 7B, 7C, 7D, 7E:
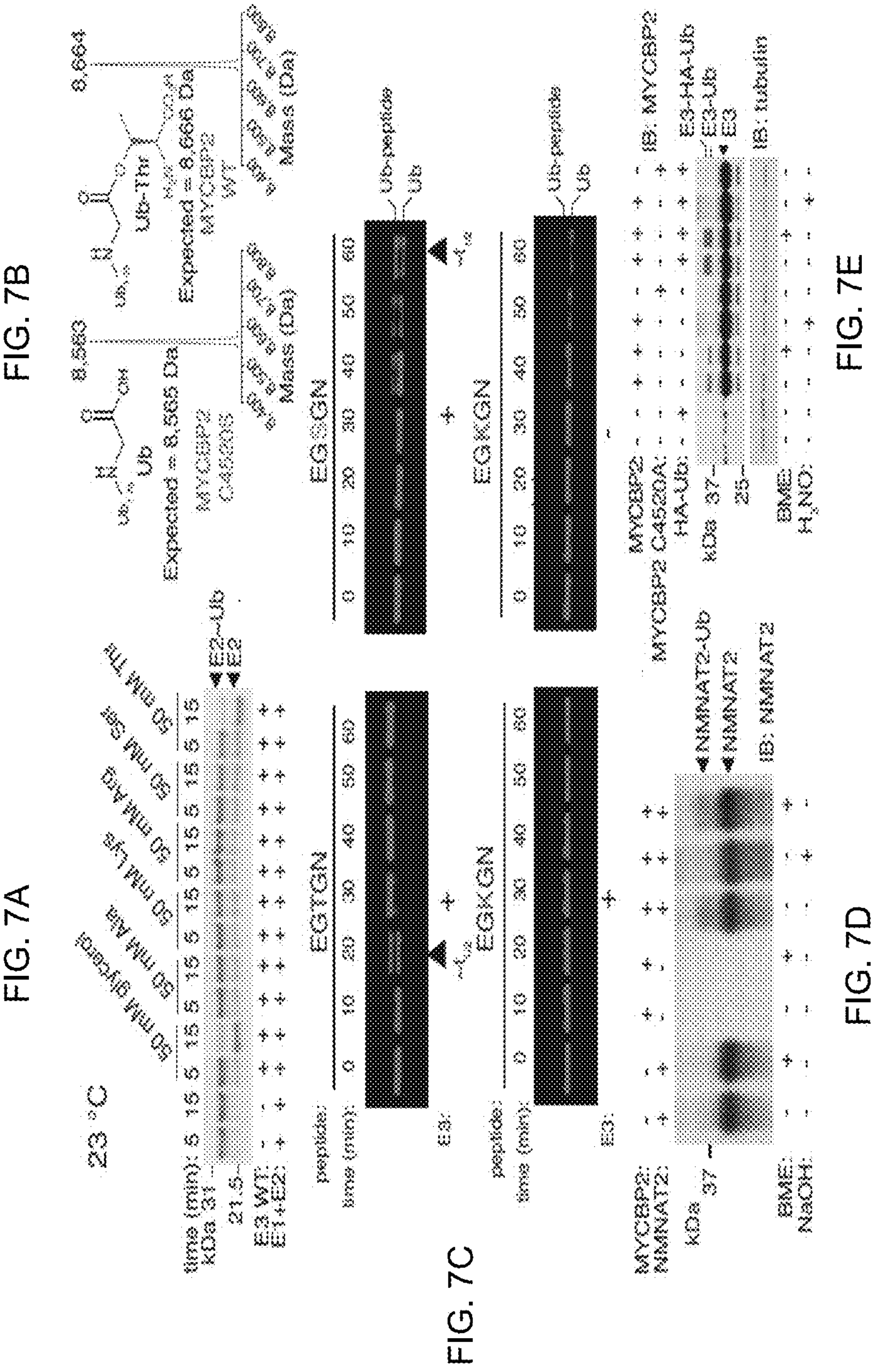
Figures 8A, 8B, 8C, 8D, 8E:
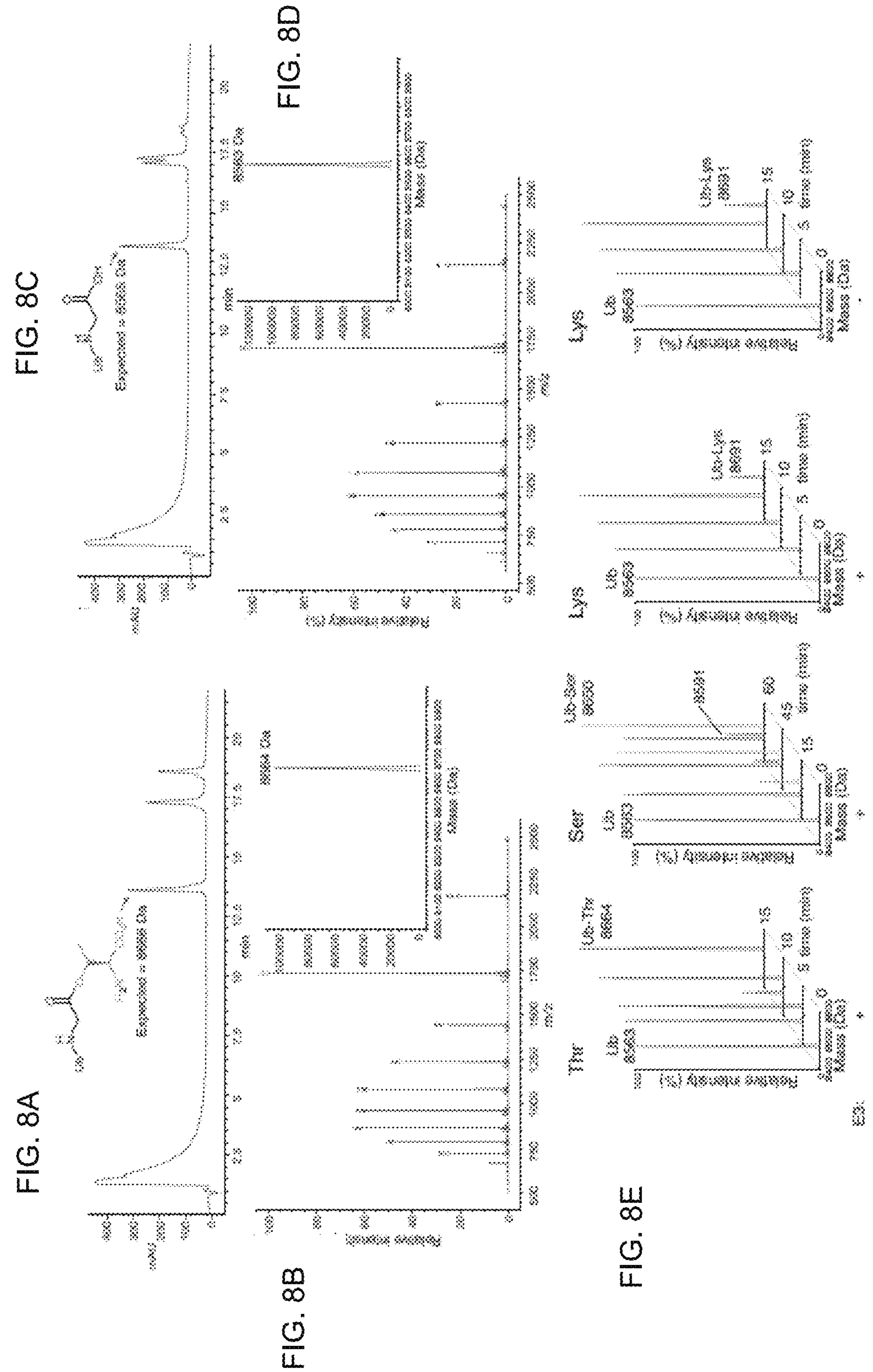
Figures 8F, 8G, 8H, 8I, 8J, 8K:
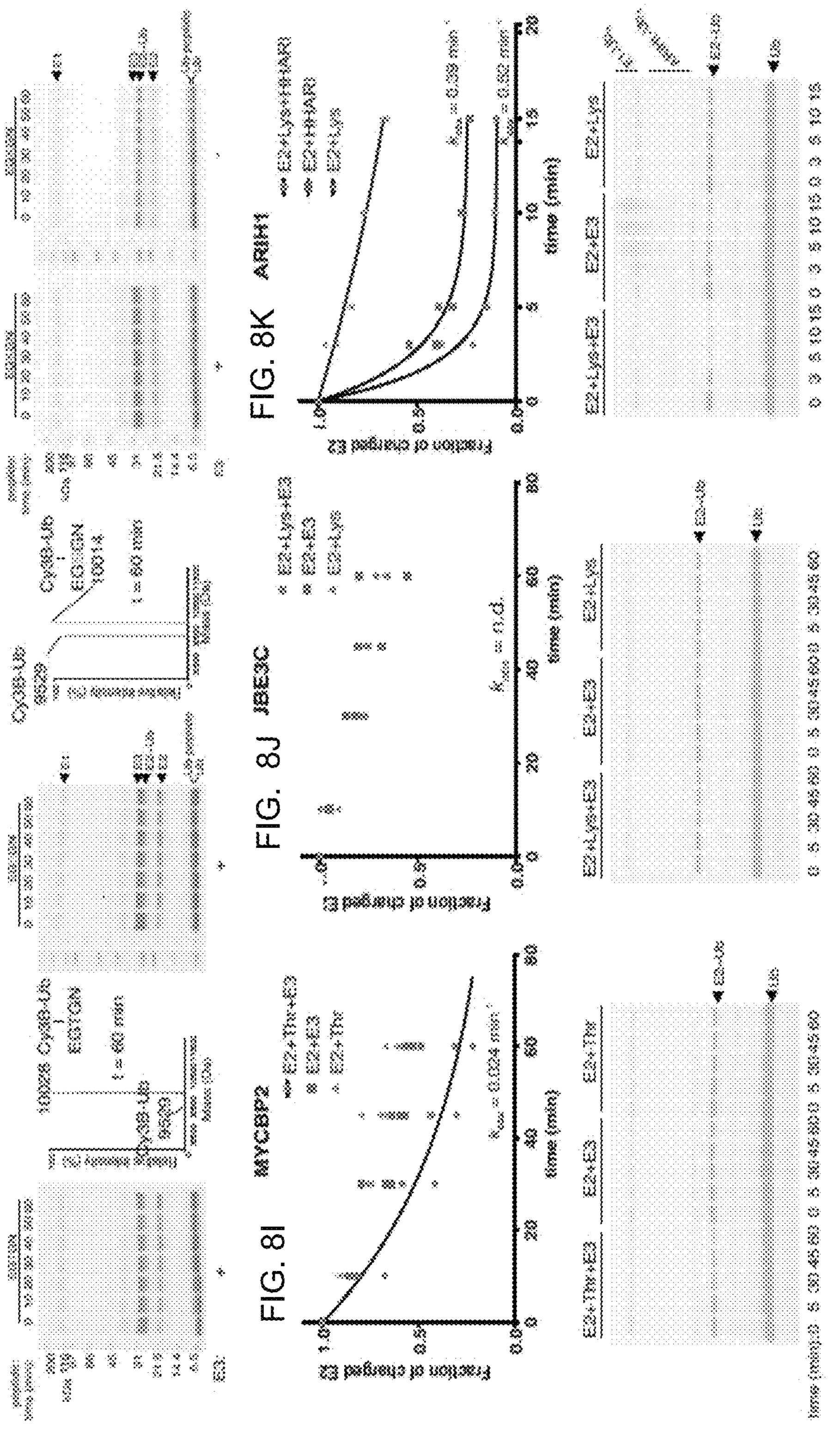

In light of the observed esterification activity we attempted to identify the amino acid substrate of MYCBP2 by screening a panel of amino acids' where discharge activity was strikingly enhanced towards threonine. Product formation was dependent on C4520 (FIG. 7A, FIG. 7B, and FIGS. 8A through 8D). MS-based quantification indicated ~10-fold selectivity for threonine over serine (FIG. 8E). Although a low level of lysine modification was observed, this was independent of MYCBP2$_{cat}$[5]. Threonine selectivity (3-fold) was also maintained in a peptide context (FIG. 7C and FIGS. 8F through 8H). Furthermore, basal ubiquitination of a lysine peptide was partially inhibited in the presence of MYCBP2$_{cat}$ underscoring its lack of lysine activity (FIG. 7C). Taken together, our experiments revealed that MYCBP2 is a novel class of E3 enzyme that operates via two essential cysteines, promotes Ub modification of hydroxyl groups, and esterifies threonine with Ub with selectivity over serine. As MYCBP2 uses a novel mechanism we termed it a RING-Cys-Relay (RCR) E3. We benchmarked the catalytic efficiency of MYCBP2 threonine esterification activity and found it to fall between that of well-characterized HECT and RBR E3 lysine aminolysis activity[5,15] (FIGS. 8I through 8K). E2 mutational analysis[5,16-19], was in further support of MYCBP2$_{cat}$ being a novel class of E3 (FIG. 9A, FIG. 9B, and Methods). To ascertain functional E2 partners, 17 E2s were tested but only UBE2D1, UBE2D3 and UBE2E1 demonstrated robust activity (FIG. 9C).

MYCBP2 promotes Wallerian axon degeneration through destabilization of Nicotinamide Mononucleotide Adenyltransferase (NMNAT2)[20]. We next tested whether MYCBP2$_{cat}$ can ubiquitinate NMNAT2 by esterification in vitro (FIG. 7D). Despite containing 13 lysine residues, NMNAT2 underwent hydroxide labile but thiol resistant ubiquitination, demonstrating that MYCBP2 can target hydroxy residues within one of its putative substrates[20]. Cellular substrate recognition is mediated by a Skp1/Fbox45 substrate receptor co-complex that binds to a site ~1940 residues N-terminal to the MYCBP2$_{cat}$ region (FIG. 7A)[21]. NMNAT2 also undergoes palmitoylation and rapid axonal transport[22] making reconstitution and cellular study of its ubiquitination extremely challenging. However, to establish whether MYCBP2$_{cat}$ retains non-lysine activity in cells we looked at its autoubiquitination after transient transfection into human embryonic kidney 293 cells. Base-labile (but thiol-resistant) ubiquitination was observed that was dependent on C4520 (FIG. 7E). This demonstrates that MYCBP2 can retain specificity for hydroxy amino acids in cells and that this activity remains dependent on the upstream catalytic residue we implicate with a Ub relay mechanism.

Figure 10A:
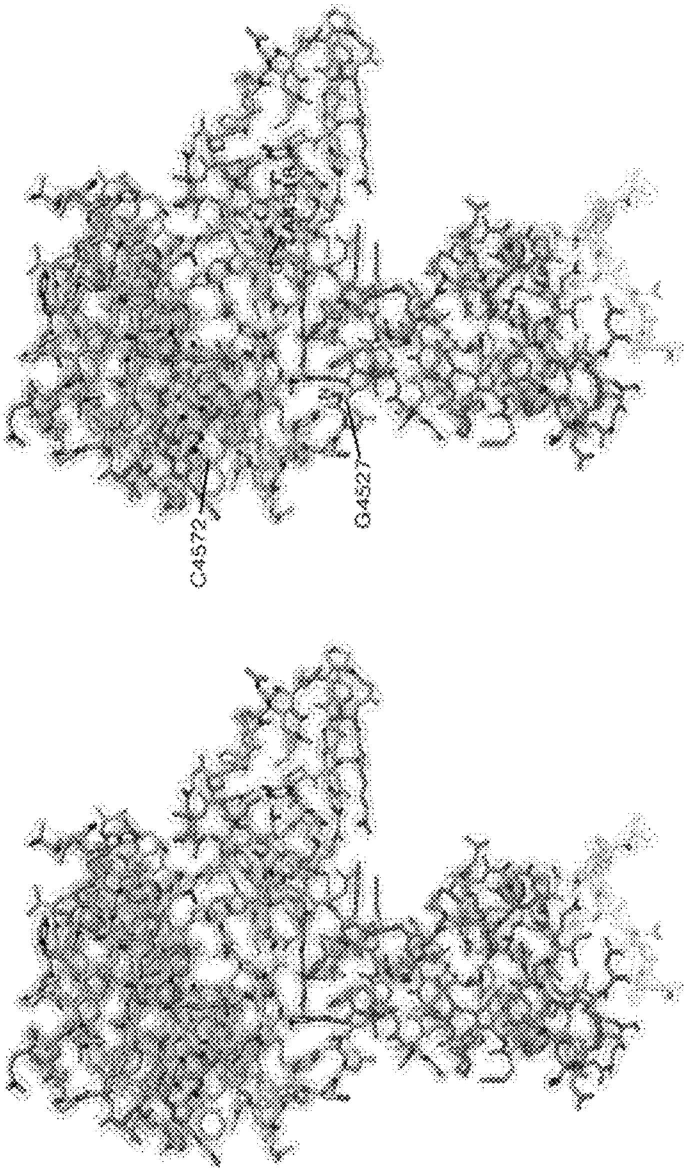
Figure 10C:
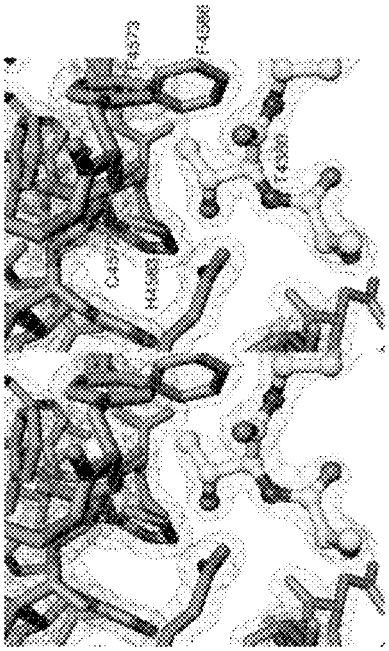
Figure 10B:
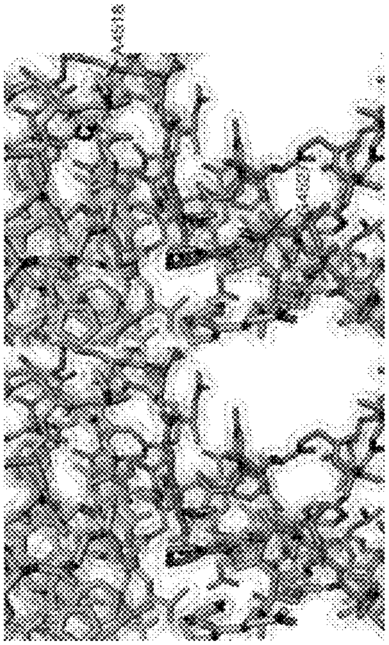
Figure 10D:
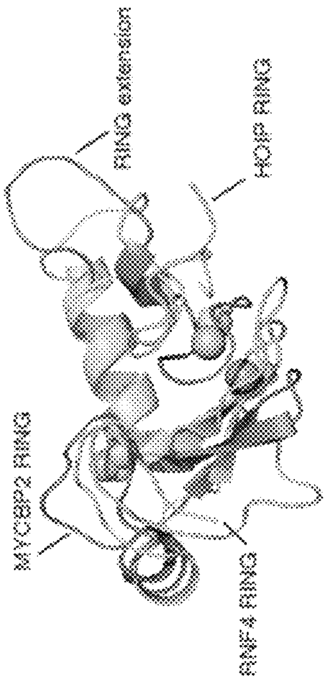
Figure 10E:
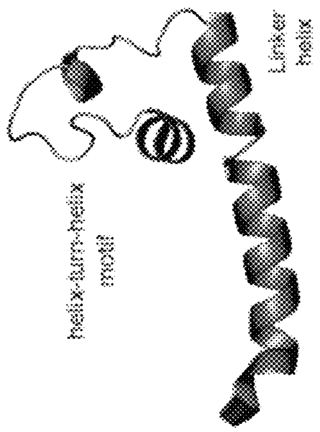
Figure 10G:
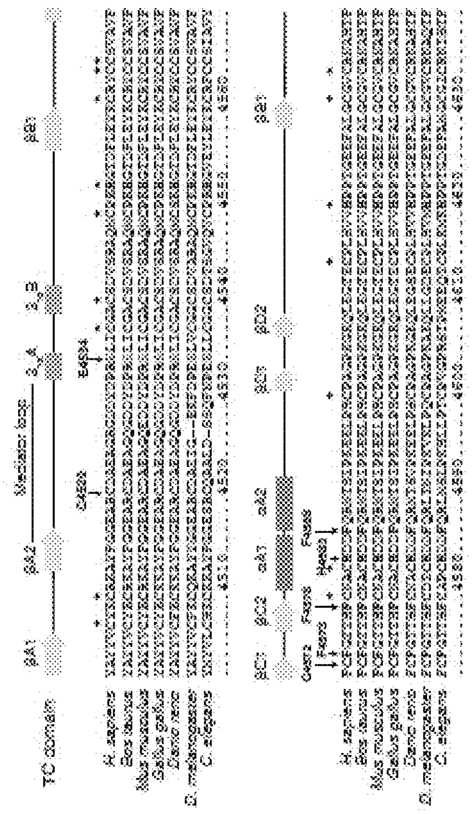
Figure 10F:
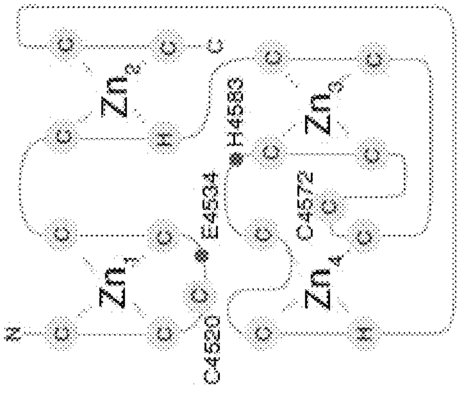
Figure 11B:
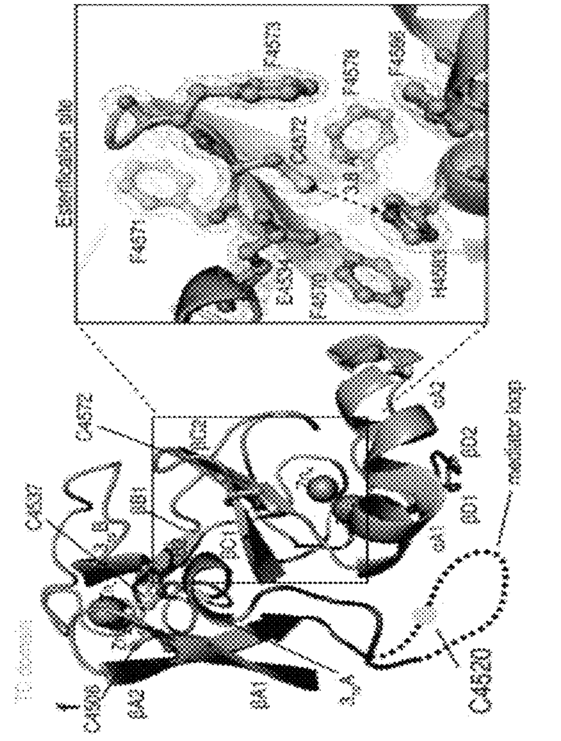
Figure 11A:
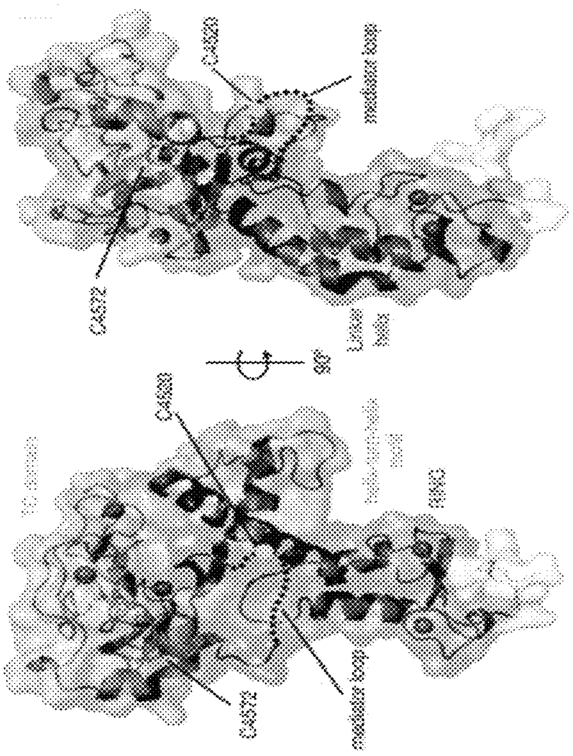

To further validate the RING-Cys-relay model and the serine/threonine activity we crystallized MYCBP2$_{cat}$ (residues 4378-4640) and solved a crystal structure to a resolution 1.75 Å (FIG. 15 and FIGS. 10A through 10C). Residues 4388-4441 at the N-terminus correspond to the predicted cross-brace C3H2C3 RING domain (FIG. 4A and FIG. 10D). Following the RING domain is a long α-helix (4447-4474) that leads into small helix-turn-helix motif (residues 4475-4500) (FIG. 11A and FIG. 10E) and further C-terminal is a structurally unprecedented globular domain that binds four Zn ions (residues 4501-4638) (FIG. 11B, FIG. 10F, and FIG. 10G). Since this domain also contains the two essential catalytic residues we term it the Tandem Cysteine (TC) domain. Between the μA2 strand and helix $3_{10}$A is an unstructured region (4519-4526) which projects out to the side of the core Zn-binding fold. The upstream C4520 residue resides within this unstructured region, which together with flanking residues, forms a mobile region we term the mediator loop. The Zn coordination configuration (C5HC7HC2) of the TC domain is semi-contiguous and does not adopt cross-brace architecture (FIG. 10C).

Figure 12A:
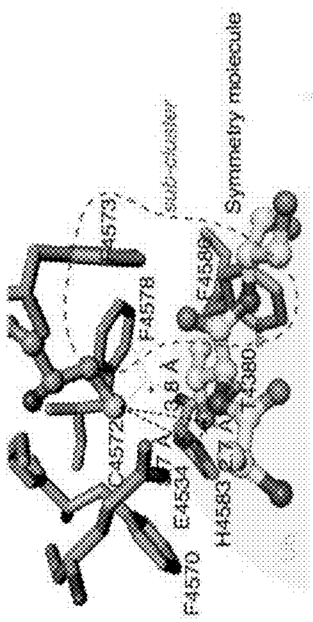
Figure 12B:
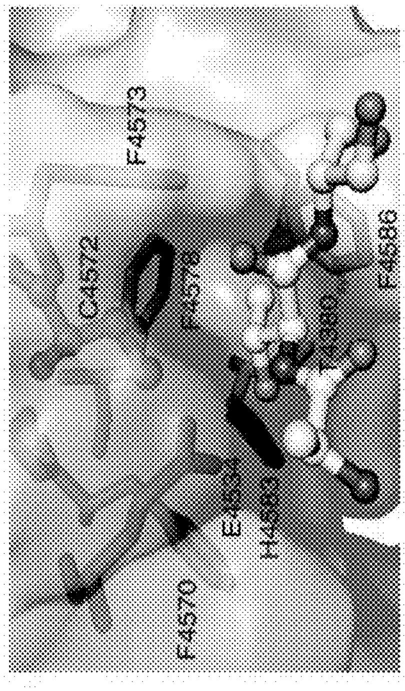
Figure 12C:
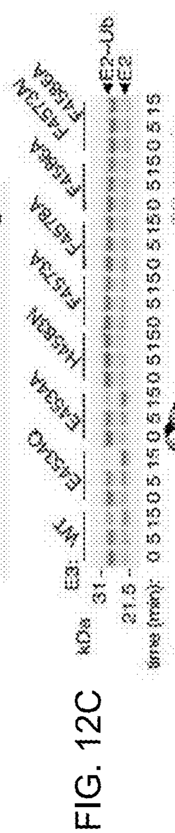

Crystal packing revealed that T4380, within the N-terminus of a symmetry-related MYCBP2$_{cat}$ molecule (T4380$_{sym}$), was placed proximal to the esterification site where it forms a number of substrate-like interactions (FIG. 12A and FIG. 12B). Firstly, the β-hydroxy group of T4380$_{sym}$ complements E4534 and H4583 and forms a potential triad (FIG. 12A). Thus the n-oxygen atom of T4380$_{sym}$ appears to be primed for deprotonation and nucleophilic attack. A catalytically productive electrophilic center is the C-terminus of Ub when thioester-linked to C4572. Even though this Ub molecule is absent in our structure, the C4572 sulfur atom is 3.8 Å away from the β-oxygen atom of T4380$_{sym}$. Thus, the structure appears to accurately reflect a catalytic intermediate poised to undergo threonine ubiquitination by esterification of its β-hydroxy group (FIG. 12A). Furthermore, a sub-cluster of Phe residues (F4573, F4578 and F4586), proximal to the β-methyl group of T4380$_{sym}$, (FIGS. 12A and FIG. 12B) forms a well-defined hydrophobic pocket which the T4380$_{sym}$ δ-methyl group docks into and appears to be a positive selectivity determinant for the threonine side chain. The proposed roles of these residues were validated in threonine discharge assays (FIG. 12C). An H4583N mutation abolished activity consistent with a role as a general base. The H4583N mutant also underwent enhanced, thiol-sensitive, Ub adduct formation in accordance with the anticipated defect in rendering substrate nucleophiles reactive towards the C4572 thioester (FIG. 13A). Conservative perturbation of the phenylalanine cluster also markedly reduced threonine discharge activity (FIG. 5C). Perturbation of E4534 did not reduce activity hence its precise role remains unclear.

Figure 12D:
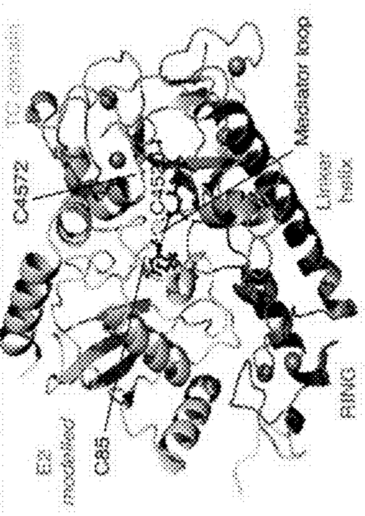
Figure 12E:
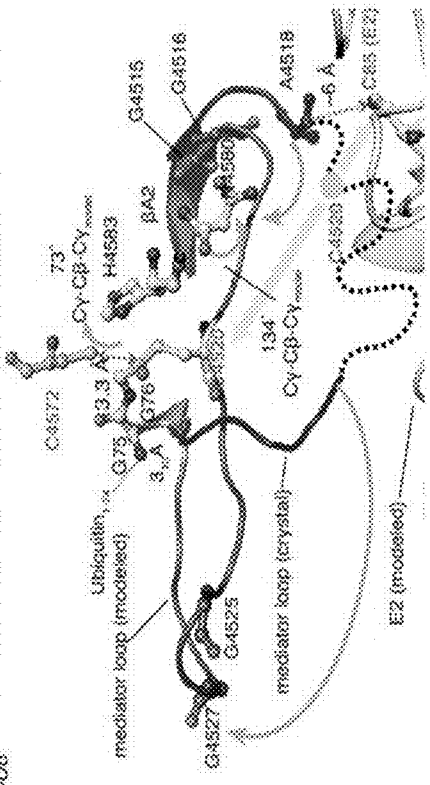
Figure 13B:
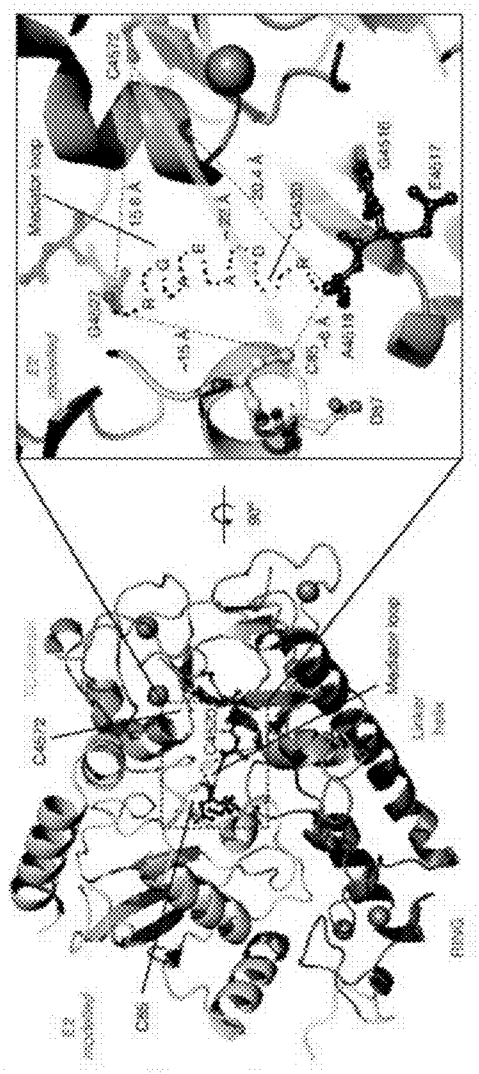
Figure 13A:
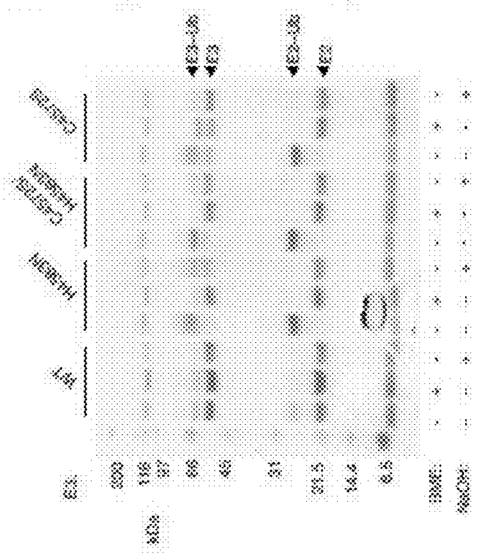
Figure 13D:
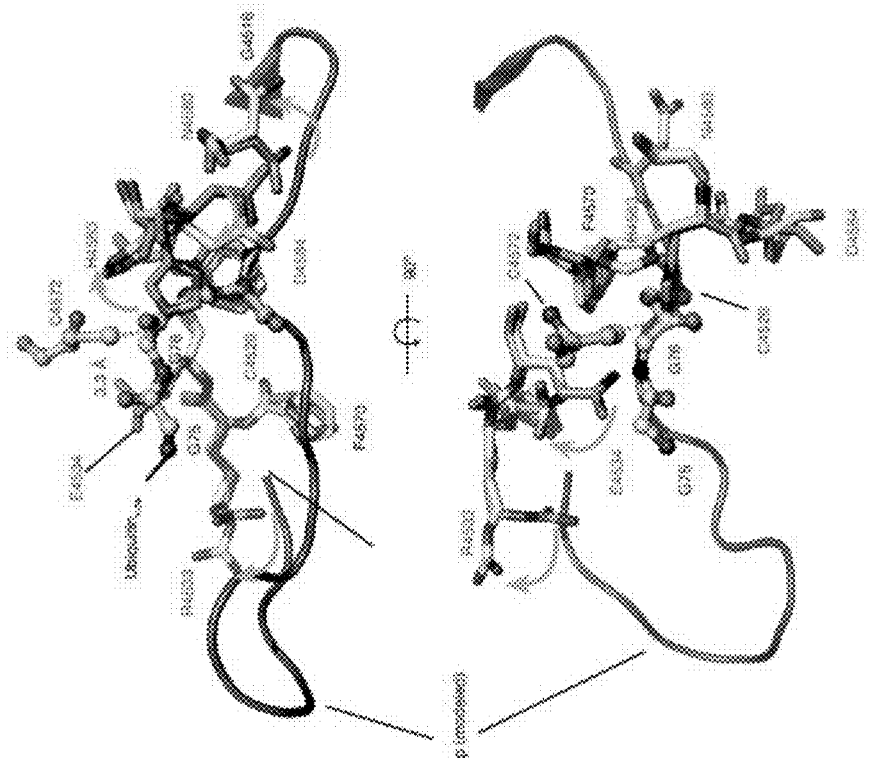
Figure 13C:
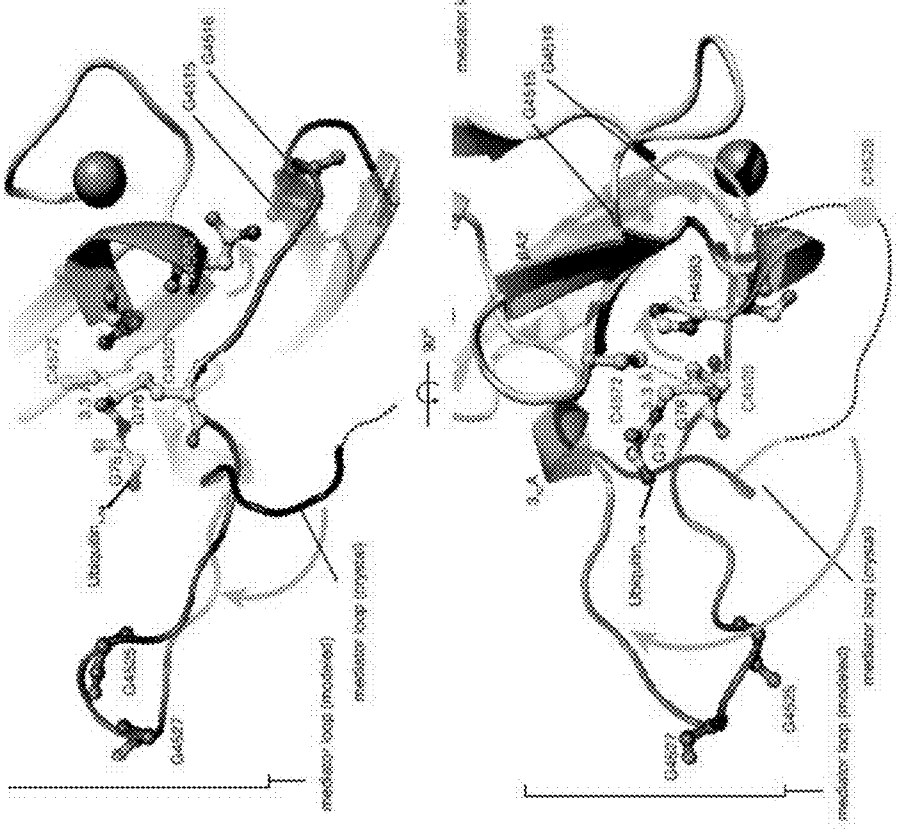
Figure 13E:
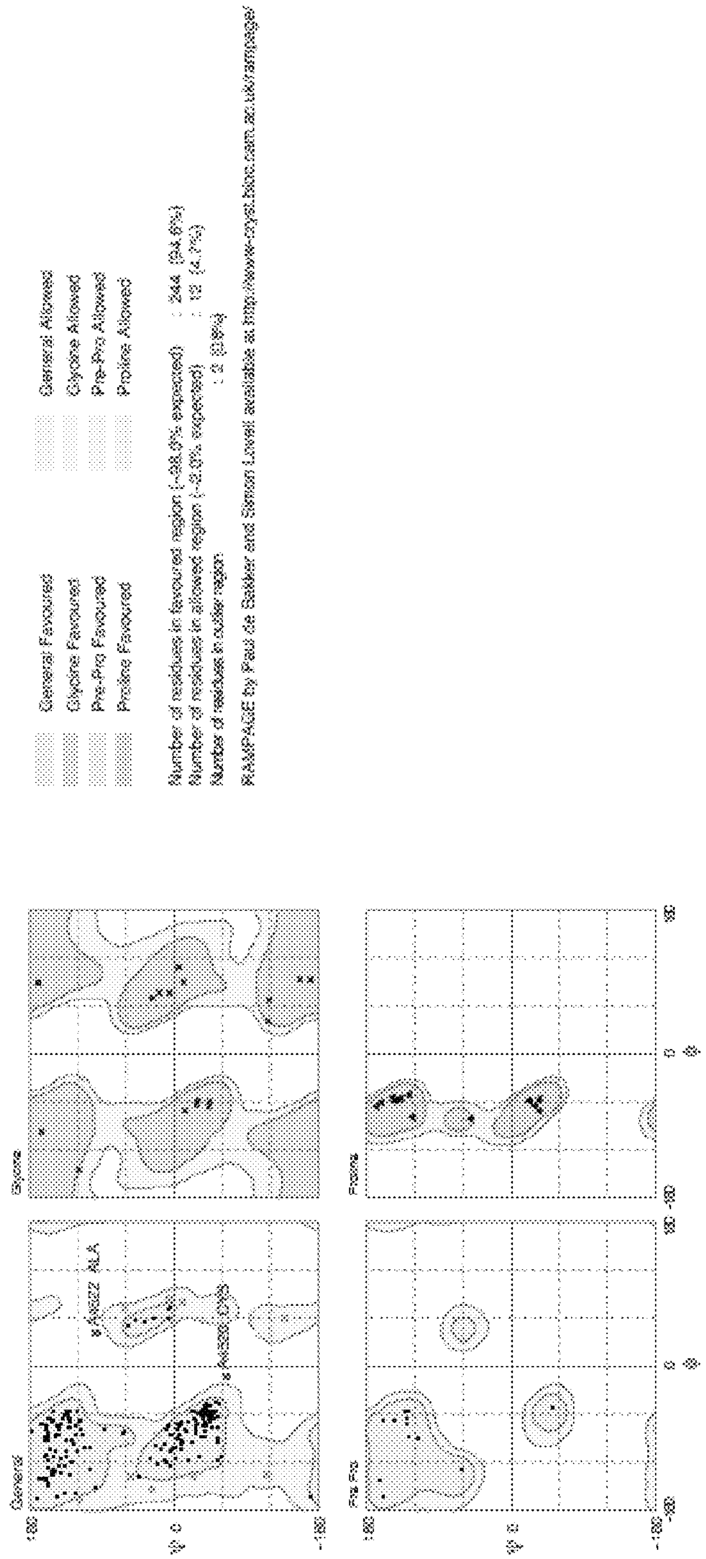

Conservation of RING domain binding to E2[16-18,23] permitted the modelling of an E2-RCR E3 ligase complex which was geometrically compatible with transthiolation between E2~Ub and MYCBP2$_{cat}$ C4520 (FIG. 5D and FIG. 13B). To simulate the conformation required for subsequent Ub relay to C4572 we modelled the missing mediator loop residues with a GlyGly dipeptide thioester linked to C4520, representative of the Ub C-terminus that would be transferred via transthiolation with E2~Ub if our relay model was valid (FIG. 13C, FIG. 12D, and FIG. 13E). In support of this mechanism the carbonyl C atom of the Ub thioester could be positioned in proximity (3.3 Å) of the C4572 sulfhydryl sulfur atom. To adopt this conformation minor twisting of a GlyGly motif (residues 4515-4516) at the tip of the βA2 strand was necessary. Clashes were observed between mediator loop residues further C-terminal with R4533, E4534, N4580, H4583 and D4584 but these could be largely relieved by rotations of their sidechains into available space. As ordered loop residues 4527-4531 required a significant displacement to generate the model, we speculate that the mobile mediator loop region would span residues 4515-4531. As C4520, which resides within this mobile structural element, needs to be engaged by the E2 active site[24] this might account for the uncharacterized E2 residue requirements. An explanation for the inability to render the S4520 mutant catalytic in earlier experiments is its dynamic nature and the absence of a general base which could suppress the $pK_a$ of the otherwise fully protonated S4520 side chain. Hence native C4520 catalytic activity is likely to arise from the sulfhydryl groups intrinsic nucleophilicity (FIG. 13A).

Figure 14:
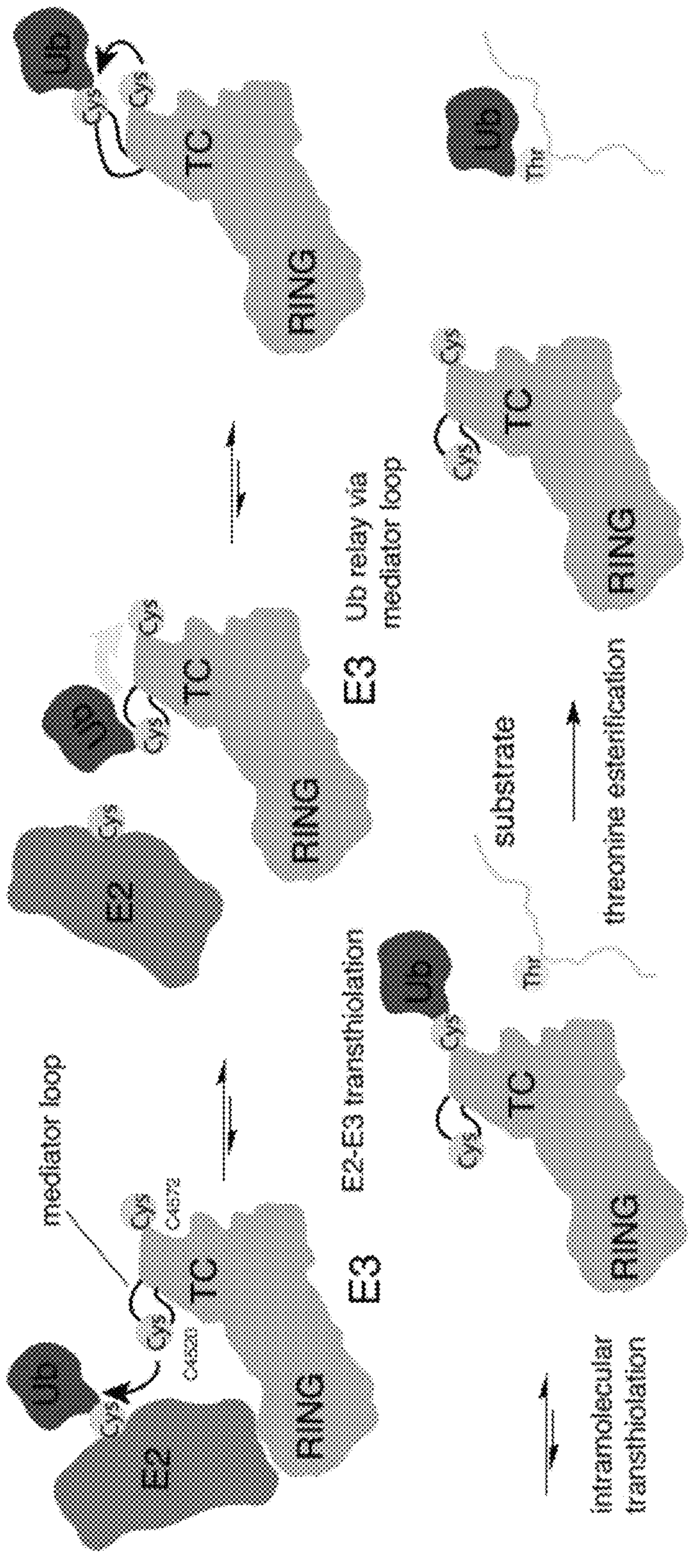
Figure 16A:
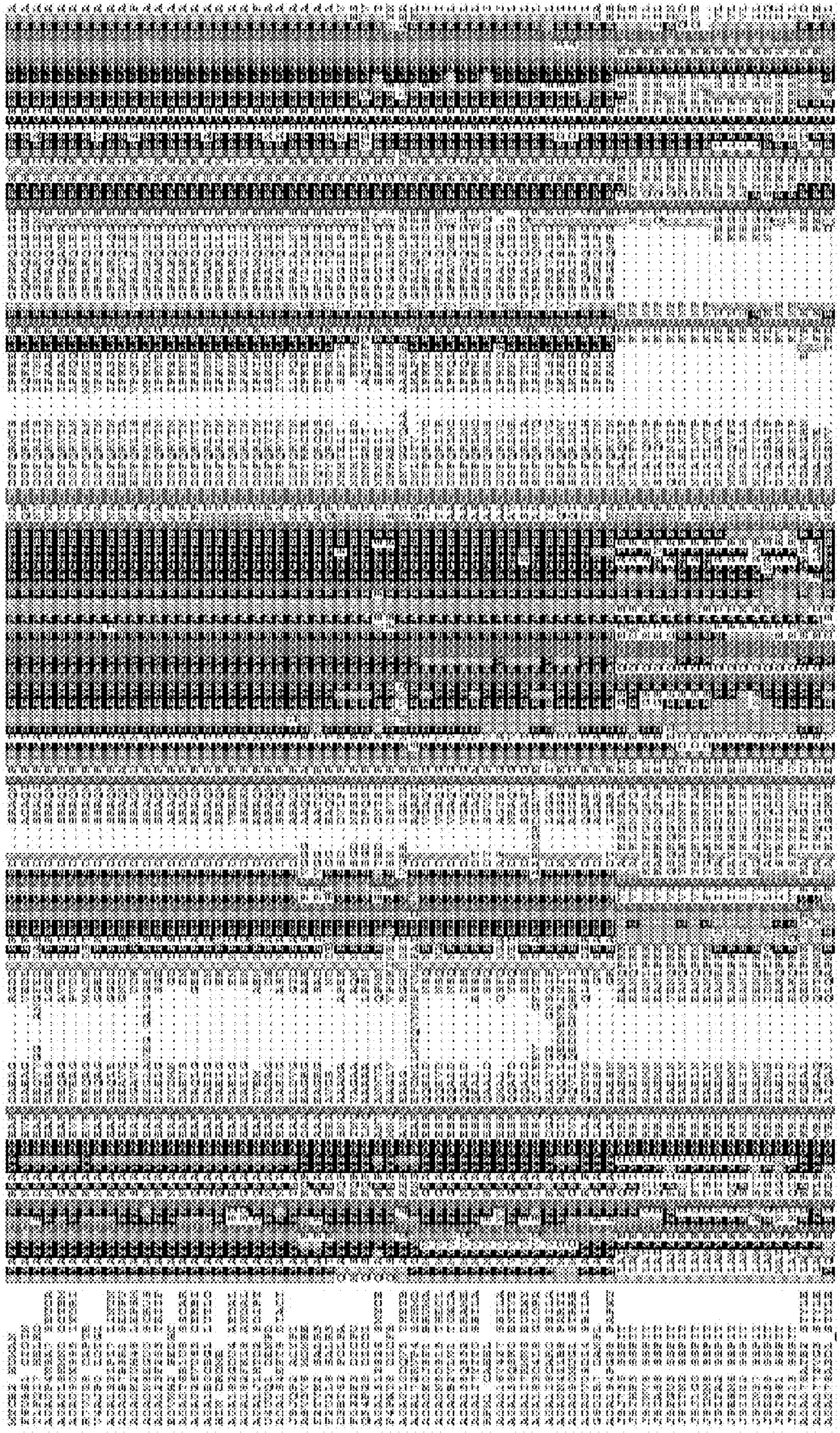
FIG. 16A and FIG. 16B are a Table showing bioinformatic analysis of MYCBP2 orthologues.
Figure 16B:
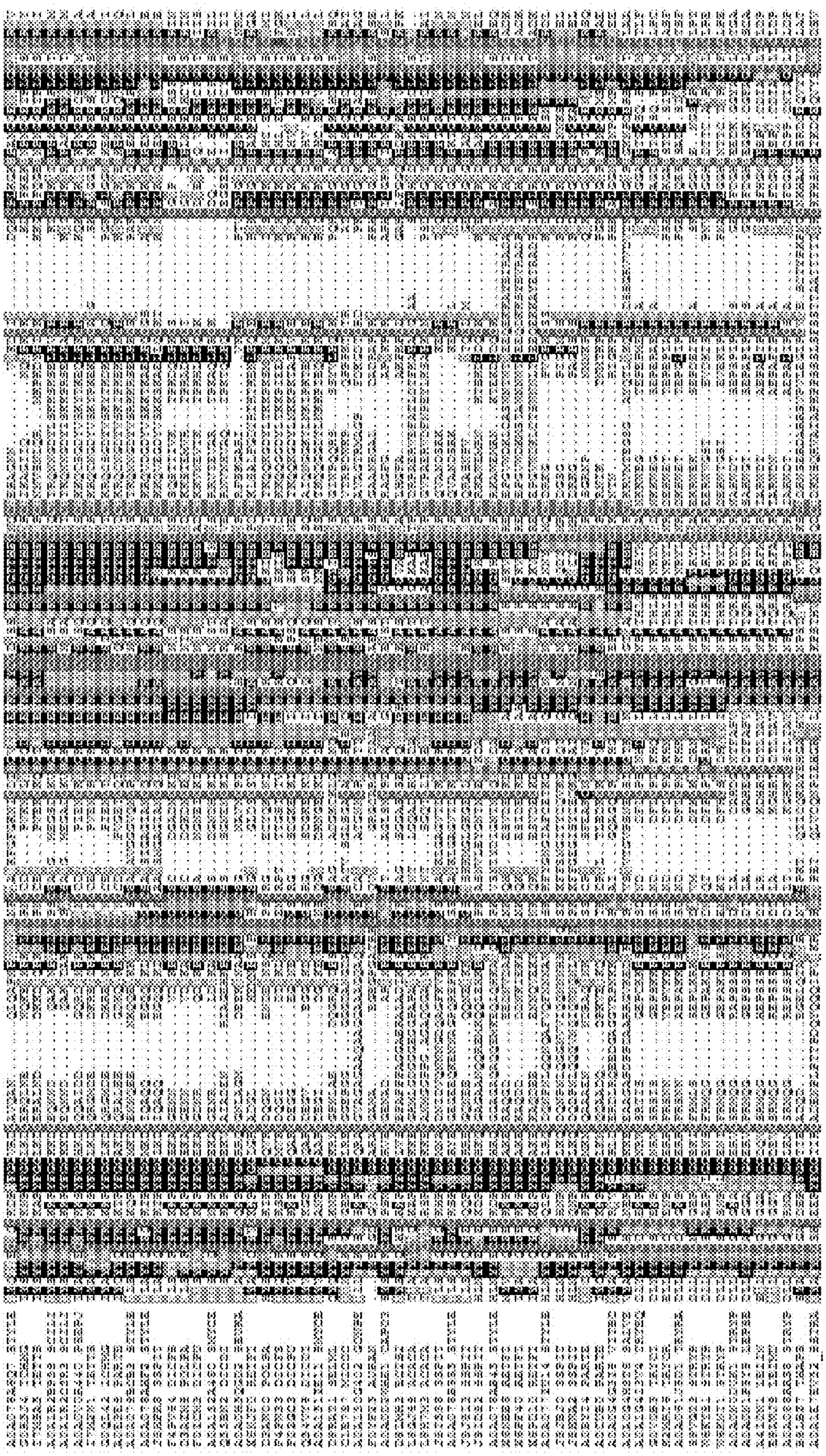

Although non-lysine ubiquitination has been reported[25-27], a human E3 ligase that preferentially carries out this function has remained elusive. Our characterization of the novel RCR E3 ligase found in MYCBP2 suggests that ubiquitination by esterification is intrinsic to higher eukaryotes and may be a regulator of synapse development and axon degradation. Furthermore, non-protein Ub substrates (e.g. lipids, carbohydrates) have not been reported but considering the high esterification activity of MYCBP2 towards small molecule hydroxy compounds, this remains a possibility. It is not immediately clear why the proposed relay (FIG. 14A) mechanism would have evolved. However, transthiolation is a cofactor independent process providing a facile means to shuttle Ub throughout the ubiquitin system1. We speculate that on steric grounds, direct E2-E3 transthiolation with the structurally rigid and highly conserved E2 ubiquitin conjugating domain (Ubc)[28], and serine/threonine activity, are mutually exclusive at the esterification site and evolution of the mediator loop addresses this compatibility issue. Bioinformatic analysis revealed that MYCBP2 orthologues are found in virtually all animals but human homologues are unlikely to exist (FIG. 16A and FIG. 16B).

Discussion

Stabilization of NMNAT2 through MYCBP2 inhibition is a promising therapeutic strategy for mitigating neuron damage after injury and administration of chemotherapeutics[10, 29,30] and slowing the progression of a range of neurodegenerative diseases including Alzheimer's and Parkinson's[29]. The delineation of this apparent Ub relay mechanism and the structural characterization of the molecular machinery responsible opens up new medical potential for treating a range of neurological conditions.

REFERENCES

1 Hershko, A. & Ciechanover, A. The ubiquitin system. *Annu Rev Biochem* 67, 425-479, (1998).
2 Deshaies, R. J. & Joazeiro, C. A. RING domain E3 ubiquitin ligases. *Annu Rev Biochem* 78, 399-434, (2009).
3 Huibregtse, J. M., Scheffner, M., Beaudenon, S. & Howley, P. M. A family of proteins structurally and functionally related to the E6-AP ubiquitin-protein ligase. *Proc Natl Acad Sci USA* 92, 2563-2567 (1995).
4 Scheffner, M., Nuber, U. & Huibregtse, J. M. Protein ubiquitination involving an E1-E2-E3 enzyme ubiquitin thioester cascade. *Nature* 373, 81-83, (1995).
5 Wenzel, D. M., Lissounov, A., Brzovic, P. S. & Klevit, R. E. UBCH7 reactivity profile reveals parkin and HHARI to be RING/HECT hybrids. *Nature* 474, 105-108, (2011).
6 Hewings, D. S., Flygare, J. A., Bogyo, M. & Wertz, I. E. Activity-based probes for the ubiquitin conjugation-deconjugation machinery: new chemistries, new tools, and new insights. *FEBS J* 284, 1555-1576, (2017).
7 Pao, K. C. et al. Probes of ubiquitin E3 ligases enable systematic dissection of parkin activation. *Nat Chem Biol* 12, 324-331, (2016).
8 Niphakis, M. J. & Cravatt, B. F. Enzyme inhibitor discovery by activity-based protein profiling. *Annu Rev Biochem* 83, 341-377, (2014).
9 Borodovsky, A. et al. Chemistry-based functional proteomics reveals novel members of the deubiquitinating enzyme family. *Chem Biol* 9, 1149-1159 (2002).
10 Zhen, M., Huang, X., Bamber, B. & Jin, Y. Regulation of presynaptic terminal organization by *C. elegans* RPM-1, a putative guanine nucleotide exchanger with a RING-H2 finger domain. *Neuron* 26, 331-343 (2000).
11 Wan, H. I. et al. Highwire regulates synaptic growth in *Drosophila. Neuron* 26, 313-329 (2000).
12 Grill, B., Murphey, R. K. & Borgen, M. A. The PHR proteins: intracellular signaling hubs in neuronal development and axon degeneration. *Neural Dev* 11, 8 (2016).
13 Byrne, R., Mund, T. & Licchesi, J. Activity-Based Probes for HECT E3 ubiquitin ligases. *Chembiochem,* 18, 1415-1427 (2017).
14 Stieglitz, B., Morris-Davies, A. C., Koliopoulos, M. G., Christodoulou, E. & Rittinger, K. LUBAC synthesizes linear ubiquitin chains via a thioester intermediate. *EMBO Rep* 13, 840-846, (2012).
15 You, J. & Pickart, C. M. A HECT domain E3 enzyme assembles novel polyubiquitin chains. *J Biol Chem* 276, 19871-19878 (2001).
16 Plechanovova, A., Jaffray, E. G., Tatham, M. H., Naismith, J. H. & Hay, R. T. Structure of a RING E3 ligase and ubiquitin-loaded E2 primed for catalysis. *Nature* 489, 115-120, (2012).
17 Dou, H., Buetow, L., Sibbet, G. J., Cameron, K. & Huang, D. T. BIRC7-E2 ubiquitin conjugate structure reveals the mechanism of ubiquitin transfer by a RING dimer. *Nat Struct Mol Biol* 19, 876-883, (2012).
18 Lechtenberg, B. C. et al. Structure of a HOIP/E2~ubiquitin complex reveals RBR E3 ligase mechanism and regulation. *Nature* 529, 546-550, (2016).
19 Dove, K. K. et al. Structural Studies of HHARI/UbcH7~Ub Reveal Unique E2~Ub Conformational Restriction by RBR RING1. *Structure* 25, 890-900 e895, (2017).
20 Xiong, X. et al. The Highwire ubiquitin ligase promotes axonal degeneration by tuning levels of Nmnat protein. *PLoS Biol* 10, e1001440, (2012).
21 Babetto, E., Beirowski, B., Russler, E. V., Milbrandt, J. & DiAntonio, A. The Phr1 ubiquitin ligase promotes injury-induced axon self-destruction. *Cell Rep* 3, 1422-1429, (2013).
22 Milde, S., Gilley, J. & Coleman, M. P. Subcellular localization determines the stability and axon protective capacity of axon survival factor Nmnat2. *PLoS Biol* 11, e1001539, (2013).

23 Zheng, N., Wang, P., Jeffrey, P. D. & Pavletich, N. P. Structure of a c-Cbl-UbcH7 complex: RING domain function in ubiquitin-protein ligases. *Cell* 102, 533-539 (2000).
24 Olsen, S. K. & Lima, C. D. Structure of a ubiquitin E1-E2 complex: insights to E1-E2 thioester transfer. *Mol Cell* 49, 884-896, (2013).
25 Cadwell, K. & Coscoy, L. Ubiquitination on nonlysine residues by a viral E3 ubiquitin ligase. *Science* 309, 127-130, (2005).
26 Shimizu, Y., Okuda-Shimizu, Y. & Hendershot, L. M. Ubiquitylation of an ERAD substrate occurs on multiple types of amino acids. *Mol Cell* 40, 917-926, (2010).
27 Wang, X., Herr, R. A. & Hansen, T. H. Ubiquitination of substrates by esterification. *Traffic* 13, 19-24, (2012).
28 Alpi, A. F., Chaugule, V. & Walden, H. Mechanism and disease association of E2-conjugating enzymes: lessons from UBE2T and UBE2L3. *Biochem J* 473, 3401-3419, (2016).
29 Conforti, L., Gilley, J. & Coleman, M. P. Wallerian degeneration: an emerging axon death pathway linking injury and disease. *Nat Rev Neurosci* 15, 394-409, (2014).
30 Ali, Y. O., Bradley, G. & Lu, H. C. Screening with an NMNAT2-MSD platform identifies small molecules that modulate NMNAT2 levels in cortical neurons. *Sci Rep* 7, 43846, (2017).
31 Stieglitz, B. et al. Structural basis for ligase-specific conjugation of linear ubiquitin chains by HOI P. *Nature* 503, 422-426, (2013).
32 Stanley, M. et al. Orthogonal thiol functionalization at a single atomic center for profiling transthiolation activity of E1 activating enzymes. *ACS Chem Biol* 10, 1542-1554, (2015).
33 Yang, B. et al. Identification of cross-linked peptides from complex samples. *Nat Methods* 9, 904-906, (2012).
34 Pruneda, J. N. et al. Structure of an E3:E2~Ub complex reveals an allosteric mechanism shared among RING/U-box ligases. *Mol Cell* 47, 933-942, (2012).
35 Wu, P. Y. et al. A conserved catalytic residue in the ubiquitin-conjugating enzyme family. *EMBO J* 22, 5241-5250, (2003).
36 Yunus, A. A. & Lima, C. D. Lysine activation and functional analysis of E2-mediated conjugation in the SUMO pathway. *Nat Struct Mol Biol* 13, 491-499, (2006).
37 Brownell, J. E. et al. Substrate-assisted inhibition of ubiquitin-like protein-activating enzymes: the NEDD8 E1 inhibitor MLN4924 forms a NEDD8-AMP mimetic in situ. *Mol Cell* 37, 102-111, (2010).
38 Langer, G., Cohen, S. X., Lamzin, V. S. & Perrakis, A. Automated macromolecular model building for X-ray crystallography using ARP/wARP version 7. *Nat Protoc* 3, 1171-1179, (2008).
39 Emsley, P., Lohkamp, B., Scott, W. G. & Cowtan, K. Features and development of Coot. *Acta Crystallogr D Biol Crystallogr* 66, 486-501, (2010).
40 Murshudov, G. N. et al. REFMAC5 for the refinement of macromolecular crystal structures. *Acta Crystallogr D Biol Crystallogr* 67, 355-367, (2011).
41 Lovell, S. C. et al. Structure validation by Ca geometry: phi, psi and Cβ deviation. *Proteins* 50, 437-450, (2003).
42 Jinek, M., et al. (2012) *Science,* 337, 816-821.
43 Overballe-Petersen, S., et al. (2013) *Proc. Natl. Acad. Sci. U.S.A.* 110, 19860-19865.
44 Gong, C., et al. (2005) *Nat. Struct. Mol. Biol.* 12, 304-312.
45 Davis, L., Maizels, N. (2014) *Proc. Natl. Acad. Sci USA,* 111, E924-932.
46 Ran, F. A., et al. (2013) *Cell,* 154, 1380-1389.
47 Qi, L. S., et al. (2013) *Cell,* 152, 1173-1183.
48 Gasiunas, G., et al. (2012) *Proc. Natl. Acad. Sci USA,* 109, E2579-2586.
49 Maede, M. L., et al. (2013) *Nat. Methods,* 10, 977-979
50 Gilbert, L. A., et al. (2013) *Cell,* 154, 442-451.
51 Hu, J., et al. (2014) *Nucleic Acids Res.* doi:10.1093/nar/gku109.
52 Perez-Pinera, P., et al. (2013) *Nat. Methods,* 10, 239-242.
53 Chen, B., et al. (2013) *Cell,* 155, 1479-1491.
54 Seung, W., et al. (2014) *Genome Res.* 24, 132-141.
55 Miller, J. C., et al. (2011). *Nat. Biotechnol.* 29, 143-148.
56 Mussolino, C., et al. (2011). *Nucleic Acids Res.* 39, 9283-9293.
57 Maeder, M. L., et al. (2008) *Mol. Cell,* 31, 294-301.
58 Hwang, W. Y., et al. (2013) *PLoS One,* 8:e68708.
59 Feng, Z., et al. (2013) *Cell Res.* 23, 1229-1232.
60 Mali, P., et al. (2013) *Science,* 339, 823-826.
61 Zhou, J., et al. (2014) *FEBS J.* doi:10.1111/febs.12735.
62 Fu, Y., et al. (2013) *Nat. Biotechnol.* 31, 822-826.
63 Fu, Y., et al. (2014) *Nat Biotechnol.* doi: 10.1038/nbt.2808.
64 Hsu, P. D., et al. (2013) *Nat. Biotechnol.* 31, 827-832.
65 Sander, J. D., et al. (2007) *Nucleic Acids Res.* 35, W599-605.
66 Sander, J. D., et al (2010) *Nucleic Acids Res.* 38, W462-468.

The invention claimed is:

1. A method for identifying a modulator of myc-binding protein 2 (MYCBP2) esterification activity towards hydroxy-containing substrates, the method comprising:

(a) contacting (i) a test substance;

(ii) an active MYCBP2 protein selected from (1) native human MYCBP2 or an active fragment thereof which contains the MYCBP2 active site, (2) an active orthologue of MYCBP2 or an active fragment thereof, each of which contains the MYCBP2 active site, and (3) an active mutant of MYCBP2 which contains the MYCBP2 active site, wherein the MYCBP2 active site contains two transthiolation catalytic cysteine residues of human MYCBP2;

(iii) ubiquitin; and (iv) a ubiquitin conjugating enzyme (E2) selected from the group consisting of UBE2D1, UBE2D2, UBE2D3, UBE2D4, and UBE2E1;

(b) providing a hydroxy-containing substrate wherein the hydroxy group of the substrate interacts with the MYCBP2 active site; and (c) detecting whether or not the level of interaction of the hydroxy-containing substrate with the MYCBP2 active site is modulated as compared to the level of interaction in the absence of the test substance, wherein transthiolation of ubiquitin between the E2 and the MYCBP2 active site leads to intramolecular relay of ubiquitin to the hydroxy-containing substrate.

2. The method of claim 1, wherein the active MYCBP2 protein is selected from (1) native human MYCBP2 or an active fragment thereof which contains the sequence GEARCDAEA (SEQ ID NO:1) and AVFFCFGTT (SEQ ID NO:2), (2) an active orthologue of MYCBP2 or an active fragment thereof, each of which contains the sequence GEARCDAEA (SEQ ID NO:1) and AVFFCFGTT (SEQ ID NO:2), and (3) an active mutant of MYCBP2 which contains the sequence GEARCDAEA (SEQ ID NO:1) and AVFFCFGTT (SEQ ID NO:2).

3. The method according to claim 1, wherein the hydroxy-containing substrate comprises a non-endogenous substrate of active MYCBP2.

4. The method according to claim 1, wherein the hydroxy-containing substrate is conjugated to a surface.

5. The method according to claim 1, wherein the hydroxy-containing substrate comprises a peptide.

6. The method according to claim 1, wherein the hydroxy-containing substrate comprises threonine or serine.

7. The method according to claim 1, wherein the hydroxy-containing substrate comprises a small molecule.

8. The method according to claim 1, wherein the hydroxy-containing substrate comprises Tris, glycerol, or 4-(2-hydroxyethyl)-1-piperazineethanesulfonic acid (HEPES).

9. The method according to claim 1, wherein the orthologue is selected from mouse MYCBP2, zebrafish MYCBP2/Esrom, *Drosophila* Highwire, and *C. elegans* regulator of presynaptic morphology 1 (RPM-1).

10. The method according to claim 1, wherein the test substance comprises a peptide, a small molecule, an aptamer, an antibody or an antibody fragment.

11. The method according to claim 1, wherein the hydroxy-containing substrate comprises a label.

12. The method according to claim 11, wherein the label comprises an affinity tag.

13. The method according to claim 1, wherein the MYCBP2, the orthologue, or the fragment thereof is recombinant.

* * * * *

SEQUENCE LISTING

```
<160> NUMBER OF SEQ ID NOS: 143

<210> SEQ ID NO 1
<211> LENGTH: 9
<212> TYPE: PRT
<213> ORGANISM: Artificial Sequence
<220> FEATURE:
<223> OTHER INFORMATION: part of sequence of MYCBP2

<400> SEQUENCE: 1

Gly Glu Ala Arg Cys Asp Ala Glu Ala
1               5


<210> SEQ ID NO 2
<211> LENGTH: 9
<212> TYPE: PRT
```

-continued

```
<213> ORGANISM: Artificial Sequence
<220> FEATURE:
<223> OTHER INFORMATION: part of sequence of MYCBP2

<400> SEQUENCE: 2

Ala Val Phe Phe Cys Phe Gly Thr Thr
1               5


<210> SEQ ID NO 3
<211> LENGTH: 18
<212> TYPE: PRT
<213> ORGANISM: Artificial Sequence
<220> FEATURE:
<223> OTHER INFORMATION: part of sequence of ABP

<400> SEQUENCE: 3

Ile Tyr His Pro Asn Ile Asn Ser Asn Gly Ser Ile Cys Leu Asp Ile
1               5                   10                  15

Leu Arg


<210> SEQ ID NO 4
<211> LENGTH: 7
<212> TYPE: PRT
<213> ORGANISM: Artificial Sequence
<220> FEATURE:
<223> OTHER INFORMATION: part of sequence of E3 ligase

<400> SEQUENCE: 4

Cys Asp Ala Glu Ala Gly Arg
1               5


<210> SEQ ID NO 5
<211> LENGTH: 5
<212> TYPE: PRT
<213> ORGANISM: Artificial Sequence
<220> FEATURE:
<223> OTHER INFORMATION: synthetic peptide

<400> SEQUENCE: 5

Glu Gly Thr Gly Asn
1               5


<210> SEQ ID NO 6
<211> LENGTH: 5
<212> TYPE: PRT
<213> ORGANISM: Artificial Sequence
<220> FEATURE:
<223> OTHER INFORMATION: synthetic peptide

<400> SEQUENCE: 6

Glu Gly Ser Gly Asn
1               5


<210> SEQ ID NO 7
<211> LENGTH: 5
<212> TYPE: PRT
<213> ORGANISM: Artificial Sequence
<220> FEATURE:
<223> OTHER INFORMATION: synthetic peptide

<400> SEQUENCE: 7

Glu Gly Lys Gly Asn
1               5


<210> SEQ ID NO 8
<211> LENGTH: 140
```

```
<212> TYPE: PRT
<213> ORGANISM: Homo sapiens

<400> SEQUENCE: 8

Tyr Ala Tyr Tyr Val Cys Tyr Lys Cys Arg Lys Ala Tyr Phe Gly Gly
1               5                   10                  15

Glu Ala Arg Cys Asp Ala Glu Ala Gly Arg Gly Asp Asp Tyr Asp Pro
            20                  25                  30

Arg Glu Leu Ile Cys Gly Ala Cys Ser Asp Val Ser Arg Ala Gln Met
        35                  40                  45

Cys Pro Lys His Gly Thr Asp Phe Leu Glu Tyr Lys Cys Arg Tyr Cys
    50                  55                  60

Cys Ser Val Ala Val Phe Phe Cys Phe Gly Thr Thr His Phe Cys Asn
65                  70                  75                  80

Ala Cys His Asp Asp Phe Gln Arg Met Thr Ser Ile Pro Lys Glu Glu
                85                  90                  95

Leu Pro His Cys Pro Ala Gly Pro Lys Gly Lys Gln Leu Glu Gly Thr
            100                 105                 110

Glu Cys Pro Leu His Val Val His Pro Pro Thr Gly Glu Glu Phe Ala
        115                 120                 125

Leu Gly Cys Gly Val Cys Arg Asn Ala His Thr Phe
    130                 135                 140


<210> SEQ ID NO 9
<211> LENGTH: 140
<212> TYPE: PRT
<213> ORGANISM: Bos taurus

<400> SEQUENCE: 9

Tyr Ala Tyr Tyr Val Cys Tyr Lys Cys Arg Lys Ala Tyr Phe Gly Gly
1               5                   10                  15

Glu Ala Arg Cys Asp Ala Glu Ala Gly Gln Gly Asp Asp Tyr Asp Pro
            20                  25                  30

Arg Glu Leu Ile Cys Gly Ala Cys Ser Asp Val Ser Arg Ala Gln Met
        35                  40                  45

Cys Pro Lys His Gly Thr Asp Phe Leu Glu Tyr Lys Cys Arg Tyr Cys
    50                  55                  60

Cys Ser Val Ala Val Phe Phe Cys Phe Gly Thr Thr His Phe Cys Asn
65                  70                  75                  80

Ala Cys His Asp Asp Phe Gln Arg Met Thr Ser Ile Pro Lys Glu Glu
                85                  90                  95

Leu Pro His Cys Pro Ala Gly Pro Lys Gly Lys Gln Leu Glu Gly Thr
            100                 105                 110

Glu Cys Pro Leu His Val Val His Pro Pro Thr Gly Glu Glu Phe Ala
        115                 120                 125

Leu Gly Cys Gly Val Cys Arg Asn Ala His Thr Phe
    130                 135                 140


<210> SEQ ID NO 10
<211> LENGTH: 140
<212> TYPE: PRT
<213> ORGANISM: Mus musculus

<400> SEQUENCE: 10

Tyr Ala Tyr Tyr Val Cys Tyr Lys Cys Arg Lys Ala Tyr Phe Gly Gly
1               5                   10                  15

Glu Ala Arg Cys Asp Ala Glu Ala Gly Gln Gly Asp Asp Tyr Asp Pro
```

```
            20                  25                  30

Arg Glu Leu Ile Cys Gly Ala Cys Ser Asp Val Ser Arg Ala Gln Met
        35                  40                  45

Cys Pro Lys His Gly Thr Asp Phe Leu Glu Tyr Lys Cys Arg Tyr Cys
    50                  55                  60

Cys Ser Val Ala Val Phe Phe Cys Phe Gly Thr Thr His Phe Cys Asn
65                  70                  75                  80

Ala Cys His Asp Asp Phe Gln Arg Met Thr Ser Ile Pro Lys Glu Glu
                85                  90                  95

Leu Pro His Cys Pro Ala Gly Pro Lys Gly Lys Gln Leu Glu Gly Thr
            100                 105                 110

Glu Cys Pro Leu His Val Val His Pro Pro Thr Gly Glu Glu Phe Ala
        115                 120                 125

Leu Gly Cys Gly Val Cys Arg Asn Ala His Thr Phe
    130                 135                 140


<210> SEQ ID NO 11
<211> LENGTH: 140
<212> TYPE: PRT
<213> ORGANISM: Gallus gallus

<400> SEQUENCE: 11

Tyr Ala Tyr Tyr Val Cys Tyr Lys Cys Lys Lys Ala Tyr Phe Gly Gly
1               5                   10                  15

Glu Ala Arg Cys Asp Ala Glu Ala Gly Gln Gly Asp Asp Tyr Asp Pro
            20                  25                  30

Arg Glu Leu Ile Cys Gly Ala Cys Ser Asp Val Ser Arg Ala Gln Met
        35                  40                  45

Cys Pro Lys His Gly Thr Asp Phe Leu Glu Tyr Lys Cys Arg Tyr Cys
    50                  55                  60

Cys Ser Val Ala Val Phe Phe Cys Phe Gly Thr Thr His Phe Cys Asn
65                  70                  75                  80

Ala Cys His Asp Asp Phe Gln Arg Met Thr Ser Ile Pro Lys Glu Glu
                85                  90                  95

Leu Pro His Cys Pro Ala Gly Pro Lys Gly Lys Gln Leu Glu Gly Thr
            100                 105                 110

Glu Cys Pro Leu His Val Val His Pro Pro Thr Gly Glu Glu Phe Ala
        115                 120                 125

Leu Gly Cys Gly Val Cys Arg Asn Ala His Thr Phe
    130                 135                 140


<210> SEQ ID NO 12
<211> LENGTH: 140
<212> TYPE: PRT
<213> ORGANISM: Danio rerio

<400> SEQUENCE: 12

Tyr Ala Tyr Tyr Val Cys Phe Lys Cys Lys Lys Ala Tyr Phe Gly Gly
1               5                   10                  15

Glu Ala Arg Cys Asp Ala Glu Ala Gly Gln Gly Asp Asp Tyr Asp Pro
            20                  25                  30

Arg Glu Leu Ile Cys Gly Ala Cys Ser Asp Val Ser Arg Ala Gln Met
        35                  40                  45

Cys Ser Lys His Gly Thr Asp Phe Leu Glu Tyr Lys Cys Arg Tyr Cys
    50                  55                  60

Cys Ser Val Ala Val Phe Phe Cys Phe Gly Thr Thr His Phe Cys Asn
```

```
65                  70                  75                  80

Ala Cys His Asp Asp Phe Gln Arg Met Thr Ser Val Pro Lys Glu Glu
                85                  90                  95

Leu Pro His Cys Pro Ala Gly Pro Lys Gly Lys Gln Leu Glu Gly Ser
            100                 105                 110

Glu Cys Pro Leu His Val Val His Pro Pro Thr Gly Glu Glu Phe Ala
        115                 120                 125

Leu Gly Cys Gly Val Cys Arg Asn Ala His Thr Phe
    130                 135                 140
```

<210> SEQ ID NO 13
<211> LENGTH: 138
<212> TYPE: PRT
<213> ORGANISM: Drosophila melanogaster

<400> SEQUENCE: 13

```
Tyr Ala Tyr Tyr Val Cys Phe Lys Cys Gln Lys Ala Tyr Tyr Gly Gly
1               5                   10                  15

Glu Ala Arg Cys Asp Ala Glu Ile Gly Glu Lys Phe Asp Pro Glu Glu
            20                  25                  30

Leu Val Cys Gly Gly Cys Ser Asp Val Ala Arg Ala Gln Met Cys Pro
        35                  40                  45

Lys His Gly Thr Asp Phe Leu Glu Tyr Lys Cys Arg Tyr Cys Cys Ser
    50                  55                  60

Val Ala Val Phe Phe Cys Phe Gly Thr Thr His Phe Cys Asp Thr Cys
65                  70                  75                  80

His Asp Asp Phe Gln Arg Leu Thr Asn Ile Pro Lys Val Lys Leu Pro
                85                  90                  95

Gln Cys Pro Ala Gly Pro Lys Ala Lys Gln Leu Leu Gly Asp Glu Cys
            100                 105                 110

Pro Leu His Val Met His Pro Pro Thr Gly Glu Glu Phe Ala Leu Gly
        115                 120                 125

Cys Gly Val Cys Arg Asn Ala Gln Thr Phe
    130                 135
```

<210> SEQ ID NO 14
<211> LENGTH: 139
<212> TYPE: PRT
<213> ORGANISM: Caenorhabditis elegans

<400> SEQUENCE: 14

```
Tyr Met Tyr Val Leu Cys His Lys Cys Lys Lys Ala Tyr Phe Gly Gly
1               5                   10                  15

Glu Ser Arg Cys Gln Ala Ala Leu Asp Ser Ser Gln Phe Asn Pro Glu
            20                  25                  30

Glu Leu Leu Cys Gly Gly Cys Ser Asp Thr Ser Gly Val Gln Val Cys
        35                  40                  45

Pro Arg His Gly Val Glu Tyr Leu Glu Tyr Lys Cys Arg Phe Cys Cys
    50                  55                  60

Ser Ile Ala Val Tyr Phe Cys Phe Gly Thr Thr His Phe Cys Ala Pro
65                  70                  75                  80

Cys His Asp Asp Phe Gln Arg Leu Met Ser Leu Pro Lys His Leu Leu
                85                  90                  95

Pro Thr Cys Pro Val Gly Pro Arg Ser Thr Pro Met Glu Glu Gln Thr
            100                 105                 110

Cys Pro Leu Lys Met Lys His Pro Pro Thr Gly Asp Glu Phe Ala Met
```

```
        115                 120                 125

Gly Cys Gly Ile Cys Arg Asn Ile Ser Thr Phe
    130                 135


<210> SEQ ID NO 15
<211> LENGTH: 138
<212> TYPE: PRT
<213> ORGANISM: Homo sapiens

<400> SEQUENCE: 15

Arg Tyr Ala Tyr Tyr Val Cys Tyr Lys Cys Arg Lys Ala Tyr Phe Gly
1               5                   10                  15

Gly Glu Ala Arg Cys Asp Ala Glu Ala Gly Arg Gly Asp Asp Tyr Asp
            20                  25                  30

Pro Arg Glu Leu Ile Cys Gly Ala Cys Ser Asp Val Ser Arg Ala Gln
        35                  40                  45

Met Cys Pro Lys His Gly Thr Asp Phe Leu Glu Tyr Lys Cys Arg Tyr
    50                  55                  60

Cys Cys Ser Val Ala Val Phe Phe Cys Phe Gly Thr Thr His Phe Cys
65                  70                  75                  80

Asn Ala Cys His Asp Asp Phe Gln Arg Met Thr Ser Ile Pro Lys Glu
                85                  90                  95

Glu Leu Pro His Cys Pro Ala Gly Pro Lys Gly Lys Gln Leu Glu Gly
            100                 105                 110

Thr Glu Cys Pro Leu His Val Val His Pro Pro Thr Gly Glu Glu Phe
        115                 120                 125

Ala Leu Gly Cys Gly Val Cys Arg Asn Ala
    130                 135


<210> SEQ ID NO 16
<211> LENGTH: 138
<212> TYPE: PRT
<213> ORGANISM: Ciona intestinalis

<400> SEQUENCE: 16

Lys Tyr Ala Tyr Tyr Met Cys Tyr Lys Cys Asn Lys Ala Tyr Tyr Gly
1               5                   10                  15

Gly Glu Val Arg Cys Asp Ala Glu Ala Gly Val Glu Asp Leu Phe Asp
            20                  25                  30

Pro Lys Glu Leu Ile Cys Gly Ala Cys Ser Asp Val Ala Cys Ala Gln
        35                  40                  45

Ile Cys Pro Lys His Gly Thr Asp Phe Leu Glu Tyr Lys Cys Arg Tyr
    50                  55                  60

Cys Cys Ser Val Ala Val Tyr Phe Cys Phe Gly Thr Thr His Phe Cys
65                  70                  75                  80

Gln Pro Cys His Asp Asp Phe Gln Arg Ile Thr Ala Leu Gln Lys Ser
                85                  90                  95

Ala Leu Pro His Cys Pro Ala Gly Gln Lys Ala Gln Gln Leu Glu Gly
            100                 105                 110

Lys Glu Cys Pro Leu His Val Glu His Pro Pro Thr Gly Glu Glu Phe
        115                 120                 125

Ala Leu Gly Cys Gly Val Cys Arg Asn Ala
    130                 135


<210> SEQ ID NO 17
<211> LENGTH: 142
<212> TYPE: PRT
```

-continued

```
<213> ORGANISM: Helobdella robusta

<400> SEQUENCE: 17

Arg Tyr Ala Tyr Tyr Val Cys Ser Lys Cys Asp Lys Ala Tyr Tyr Gly
1               5                   10                  15

Gly Glu Ala Arg Cys Glu Glu Gln Val Val Gly Gly Ala Asn Gly Phe
            20                  25                  30

Glu Asp Tyr Asp Ala Ser Glu Leu Val Cys Gly Ala Cys Ser Asp Val
        35                  40                  45

Ser Arg Ala Gln Ile Cys Pro Lys His Gly Ala Asp Phe Leu Glu Tyr
    50                  55                  60

Lys Cys Arg Tyr Cys Cys Ser Val Ala Val Phe Phe Cys Phe Gly Thr
65                  70                  75                  80

Thr His Phe Cys Asn Val Cys His Asp Asp Phe Gln Arg Ile Thr Ser
                85                  90                  95

Ile Ser Val Asn Glu Leu Pro His Cys Pro Ala Gly Ser Lys Ala Arg
            100                 105                 110

Gln Leu Glu Gly Asn Gln Cys Pro Leu Asn Ile Ile His Pro Ala Thr
        115                 120                 125

Gly Thr Glu Phe Ala Leu Gly Cys Gly Ile Cys Arg Asn Ala
    130                 135                 140


<210> SEQ ID NO 18
<211> LENGTH: 138
<212> TYPE: PRT
<213> ORGANISM: Scylla olivacea

<400> SEQUENCE: 18

Arg Tyr Ala Tyr Tyr Val Cys Phe Lys Cys Asn Lys Ala Tyr Tyr Gly
1               5                   10                  15

Gly Glu Ala Arg Cys Asp Ala Glu Ala Gly Leu Gly Asp Glu Tyr Asp
            20                  25                  30

Pro Arg Glu Leu Val Cys Gly Ala Cys Ser Asp Val Ser Arg Ala Gln
        35                  40                  45

Met Cys Pro Lys His Gly Thr Asp Phe Leu Glu Tyr Lys Cys Arg Tyr
    50                  55                  60

Cys Cys Ser Val Ala Val Phe Phe Cys Phe Gly Thr Thr His Phe Cys
65                  70                  75                  80

Asn Ala Cys His Asp Asp Phe Gln Arg Val Thr Asn Ile Pro Lys Ala
                85                  90                  95

Glu Leu Pro Arg Cys Pro Ala Gly Pro Arg Ala Gln Gln Leu Glu Gly
            100                 105                 110

Glu Glu Cys Pro Leu His Val Gln His Pro Pro Thr Gly Glu Glu Phe
        115                 120                 125

Ala Leu Gly Cys Gly Val Cys Arg Asn Ala
    130                 135


<210> SEQ ID NO 19
<211> LENGTH: 138
<212> TYPE: PRT
<213> ORGANISM: Octopus bimaculoides

<400> SEQUENCE: 19

Arg Tyr Ala Tyr Tyr Val Cys Tyr Lys Cys Gly Lys Ala Tyr Tyr Gly
1               5                   10                  15

Gly Glu Ala Arg Cys Asp Glu Gln Ala Gly Ala Val Asp Asp Tyr Asp
            20                  25                  30
```

-continued

Pro Thr Glu Leu Val Cys Gly Ala Cys Ser Asp Val Ser Arg Ala Gln
35 40 45

Leu Cys Pro Lys His Gly Thr Asp Phe Leu Glu Tyr Lys Cys Arg Tyr
50 55 60

Cys Cys Ser Val Ala Val Phe Phe Cys Phe Gly Thr Thr His Phe Cys
65 70 75 80

Asn Thr Cys His Asp Asp Phe Gln Arg Val Thr Asn Ile Pro Lys Ala
85 90 95

Asp Leu Pro Arg Cys Pro Ala Gly Pro Lys Ala Gln Ala Met Glu Ala
100 105 110

Asp Glu Cys Pro Leu Asn Val Gln His Pro Pro Thr Gly Glu Glu Phe
115 120 125

Ala Leu Gly Cys Gly Val Cys Arg Asn Ala
130 135

<210> SEQ ID NO 20
<211> LENGTH: 138
<212> TYPE: PRT
<213> ORGANISM: Ixodes ricinus

<400> SEQUENCE: 20

Arg Tyr Ala Tyr Tyr Val Cys Phe Lys Cys Lys Lys Ala Tyr Tyr Gly
1 5 10 15

Gly Glu Val Arg Cys Asp Val Glu Ala Gly Pro Val Asp Asp Tyr Asp
20 25 30

Pro Ala Glu Leu Val Cys Gly Ala Cys Ser Asp Ile Ser Arg Ala Gln
35 40 45

Met Cys Pro Lys His Gly Thr Asp Phe Leu Glu Tyr Lys Cys Arg Tyr
50 55 60

Cys Cys Ser Val Ala Val Phe Phe Cys Phe Gly Thr Thr His Phe Cys
65 70 75 80

Asn Ala Cys His Asp Asp Phe Gln Arg Val Ala Asn Leu Pro Lys Gln
85 90 95

Gln Leu Pro Arg Cys Pro Ala Gly Pro Lys Ala Lys Gln Leu Glu Gly
100 105 110

Glu Glu Cys Pro Leu His Ile Lys His Pro Pro Thr Gly Glu Glu Phe
115 120 125

Ala Leu Gly Cys Gly Val Cys Arg Asn Ala
130 135

<210> SEQ ID NO 21
<211> LENGTH: 138
<212> TYPE: PRT
<213> ORGANISM: Capitella teleta

<400> SEQUENCE: 21

Arg Tyr Ala Tyr Tyr Val Cys Tyr Lys Cys Lys Lys Ala Tyr Phe Gly
1 5 10 15

Gly Glu Val Arg Cys Glu Glu Gln Ala Gly Met Ala Asp Glu Tyr Asp
20 25 30

Ser Thr Glu Leu Val Cys Gly Ala Cys Ser Asp Val Ser Arg Ala Gln
35 40 45

Met Cys Pro Lys His Gly Thr Asp Phe Leu Glu Tyr Lys Cys Arg Tyr
50 55 60

Cys Cys Ser Val Ala Val Phe Phe Cys Phe Gly Thr Thr His Phe Cys
65 70 75 80

```
Asn Ala Cys His Asp Asp Phe Gln Arg Val Ala Asn Met Pro Lys Gly
                85                  90                  95

Asp Leu Pro His Cys Pro Ala Gly Pro Lys Ala Lys Gln Leu Glu Gly
            100                 105                 110

Asp Glu Cys Pro Leu His Val Lys His Pro Pro Thr Gly Glu Glu Phe
        115                 120                 125

Ala Leu Gly Cys Gly Val Cys Arg Asn Ala
    130                 135


<210> SEQ ID NO 22
<211> LENGTH: 138
<212> TYPE: PRT
<213> ORGANISM: Lottia gigantea

<400> SEQUENCE: 22

Arg Tyr Ala Tyr Tyr Val Cys Tyr Lys Cys Asn Lys Ala Tyr Tyr Gly
1               5                   10                  15

Gly Glu Ala Arg Cys Asp Glu Gln Ala Gly Gly Gly Glu Asp Tyr Asp
            20                  25                  30

Pro Lys Glu Leu Val Cys Gly Gly Cys Ser Asp Val Ser Ser Ala Gln
        35                  40                  45

Met Cys Pro Lys His Gly Thr Asp Phe Leu Glu Tyr Lys Cys Arg Tyr
    50                  55                  60

Cys Cys Ser Val Ala Val Phe Phe Cys Phe Gly Thr Thr His Phe Cys
65                  70                  75                  80

Asn Ala Cys His Asp Asp Phe Gln Arg Val Thr Asn Val Pro Lys Ser
                85                  90                  95

Glu Leu Pro His Cys Pro Ala Gly Pro Arg Cys Lys Gln Leu Asp Gly
            100                 105                 110

Asp Glu Cys Pro Leu His Val Gln His Pro Val Thr Gly Glu Glu Phe
        115                 120                 125

Ala Leu Gly Cys Gly Val Cys Arg Asn Ala
    130                 135


<210> SEQ ID NO 23
<211> LENGTH: 138
<212> TYPE: PRT
<213> ORGANISM: Lingula unguis

<400> SEQUENCE: 23

Arg Tyr Ala Tyr Tyr Val Cys Tyr Lys Cys Lys Lys Ala Tyr Tyr Gly
1               5                   10                  15

Gly Glu Ala Arg Cys Asp Glu Gln Leu Glu Gly Gly Asp Asp Tyr Asp
            20                  25                  30

Pro Thr Glu Leu Val Cys Gly Ala Cys Ser Asp Val Ser Arg Ala Gln
        35                  40                  45

Met Cys Pro Lys His Gly Thr Asp Phe Leu Glu Tyr Lys Cys Arg Tyr
    50                  55                  60

Cys Cys Ser Thr Ala Val Phe Phe Cys Phe Gly Thr Thr His Phe Cys
65                  70                  75                  80

Asn Ala Cys His Asp Asp Phe Gln Arg Val Thr Asn Ile Pro Arg Ser
                85                  90                  95

Asp Leu Pro Thr Cys Pro Ala Gly Pro Arg Gly Lys Gln Leu Gln Gly
            100                 105                 110

Asp Glu Cys Pro Leu His Val Lys His Pro Pro Thr Gly Glu Glu Phe
        115                 120                 125
```

```
Ala Leu Gly Cys Gly Val Cys Arg Asn Ala
    130                 135


<210> SEQ ID NO 24
<211> LENGTH: 138
<212> TYPE: PRT
<213> ORGANISM: Arion vulgaris

<400> SEQUENCE: 24

Arg Tyr Ala Tyr Tyr Val Cys Phe Lys Cys Lys Lys Ala Tyr Tyr Gly
1               5                   10                  15

Gly Glu Ala Arg Cys Asp Glu Ala Val Gly Gly Asn Asp Asp Phe Asp
            20                  25                  30

Pro Ser Glu Leu Val Cys Gly Ala Cys Ser Asp Val Ser Arg Ala Gln
        35                  40                  45

Met Cys Ala Lys His Gly Ala Asp Phe Leu Glu Tyr Lys Cys Arg Tyr
    50                  55                  60

Cys Cys Ser Val Ala Val Phe Phe Cys Phe Gly Thr Thr His Phe Cys
65                  70                  75                  80

Asn Pro Cys His Glu Glu Phe Gln Arg Val Thr Ala Ile Pro Lys Lys
                85                  90                  95

Asp Leu Pro His Cys Pro Ala Gly Ala Lys Gly Val Gln Leu Glu Gly
            100                 105                 110

Glu Glu Cys Pro Leu His Val Leu His Pro Pro Thr Gly Glu Glu Phe
        115                 120                 125

Ala Leu Gly Cys Gly Val Cys Arg Asn Ala
    130                 135


<210> SEQ ID NO 25
<211> LENGTH: 137
<212> TYPE: PRT
<213> ORGANISM: Lepeophtheirus salmonis

<400> SEQUENCE: 25

Arg Tyr Ala Tyr Tyr Val Cys Phe Lys Cys Ser Lys Ala Tyr Tyr Gly
1               5                   10                  15

Gly Glu Ala Gln Cys Asp Gly Ala Val Gly Asp Asp Lys Phe Asn Pro
            20                  25                  30

Glu Glu Leu Val Cys Gly Gly Cys Ser Asp Val Ser Arg Ala Gln Met
        35                  40                  45

Cys Leu Lys His Gly Met Asp Tyr Leu Glu Tyr Lys Cys Arg Tyr Cys
    50                  55                  60

Cys Ser Val Ala Val Phe Phe Cys Phe Gly Thr Thr His Phe Cys Asn
65                  70                  75                  80

Ala Cys His Glu Asp Phe Gln Arg Leu Ile Ser Val Pro Gln Lys Asp
                85                  90                  95

Leu Pro Gln Cys Pro Val Gly Pro Lys Ala Leu Lys Leu Glu Gly Glu
            100                 105                 110

Glu Cys Pro Leu His Ile Lys His Pro Ser Thr Gly Glu Glu Phe Ala
        115                 120                 125

Leu Gly Cys Gly Ile Cys Arg Asn Pro
    130                 135


<210> SEQ ID NO 26
<211> LENGTH: 144
<212> TYPE: PRT
<213> ORGANISM: Daphnia magna
```

-continued

<400> SEQUENCE: 26

```
Arg Tyr Ala Tyr Tyr Val Cys Phe Arg Cys Asn Lys Ala Tyr Tyr Gly
1               5                   10                  15

Gly Glu Ala Arg Cys Glu Glu Gly Leu Ala Val Glu Gly Gly Ala Ile
            20                  25                  30

Gly Gly Glu Ser Phe Asn Pro Ser Glu Leu Val Cys Gly Gly Cys Ser
        35                  40                  45

Asp Val Ser Arg Ala Gln Met Cys Pro Arg His Gly Ala Asp Tyr Leu
    50                  55                  60

Glu Tyr Lys Cys Arg Tyr Cys Cys Ser Val Ala Val Phe Phe Cys Phe
65                  70                  75                  80

Gly Thr Thr His Phe Cys Asn Ala Cys His Glu Asp Phe Arg His Val
                85                  90                  95

Thr Glu Met Pro Lys His Ala Leu Pro Lys Cys Pro Ala Gly Pro Arg
            100                 105                 110

Gly Arg Gln Leu Asp Gly Glu Glu Cys Pro Leu His Leu Val His Pro
        115                 120                 125

Pro Thr Gly Glu Glu Phe Ala Leu Gly Cys Gly Met Cys Arg Asn Ala
    130                 135                 140
```

<210> SEQ ID NO 27
<211> LENGTH: 137
<212> TYPE: PRT
<213> ORGANISM: Triatoma infestans

<400> SEQUENCE: 27

```
Arg Tyr Ala Tyr Tyr Val Cys Phe Lys Cys Lys Lys Ala Tyr Tyr Gly
1               5                   10                  15

Gly Glu Ala Arg Cys Asp Leu Glu Leu Gly Ser Gly Glu Phe Asp Pro
            20                  25                  30

Ser Glu Leu Val Cys Gly Ala Cys Ser Asp Val Ser Arg Ala Gln Met
        35                  40                  45

Cys Pro Lys His Gly Thr Asp Phe Leu Glu Tyr Lys Cys Arg Tyr Cys
    50                  55                  60

Cys Ser Val Ala Val Phe Phe Cys Phe Gly Thr Thr His Phe Cys Asn
65                  70                  75                  80

Ala Cys His Asp Asp Phe Gln Arg Val Thr Asn Ile Pro Lys Asn Glu
                85                  90                  95

Leu Pro Gly Cys Pro Ala Gly Pro Lys Ala Lys Gln Leu Glu Gly Glu
            100                 105                 110

Glu Cys Pro Leu His Val Lys His Pro Pro Thr Gly Glu Glu Phe Ala
        115                 120                 125

Leu Gly Cys Gly Val Cys Arg Asn Ala
    130                 135
```

<210> SEQ ID NO 28
<211> LENGTH: 136
<212> TYPE: PRT
<213> ORGANISM: Pediculus humanus

<400> SEQUENCE: 28

```
Arg Tyr Ala Tyr Tyr Val Cys Phe Lys Cys Asn Lys Ala Tyr Tyr Gly
1               5                   10                  15

Gly Glu Ala Arg Cys Asp Val Asp Met Asn Gly Asp Phe Asp Pro Ser
            20                  25                  30
```

```
Glu Leu Val Cys Gly Gly Cys Ser Asp Val Ala Arg Ala Gln Met Cys
        35                  40                  45

Pro Lys His Gly Thr Asp Phe Leu Glu Tyr Lys Cys Arg Tyr Cys Cys
    50                  55                  60

Ser Val Ala Val Phe Phe Cys Phe Gly Thr Thr His Phe Cys Asn Ser
65                  70                  75                  80

Cys His Asp Asp Phe Gln Arg Val Thr Asn Ile Pro Lys Ser Asp Leu
                85                  90                  95

Pro Ala Cys Pro Ala Gly Pro Lys Ala Lys Gln Leu Asp Gly Glu Glu
            100                 105                 110

Cys Pro Leu His Val Ser His Pro Pro Thr Gly Glu Glu Phe Ala Leu
        115                 120                 125

Gly Cys Gly Val Cys Arg Asn Ala
    130                 135


<210> SEQ ID NO 29
<211> LENGTH: 136
<212> TYPE: PRT
<213> ORGANISM: Oryctes borbonicus

<400> SEQUENCE: 29

Arg Tyr Ala Tyr Tyr Val Cys Tyr Lys Cys Asn Lys Ala Tyr Tyr Gly
1               5                   10                  15

Gly Glu Ala Arg Cys Asp Ala Glu Val Ser Glu Asn Tyr Asp Pro Thr
            20                  25                  30

Glu Leu Val Cys Gly Gly Cys Ser Asp Val Ala Arg Ala Gln Met Cys
        35                  40                  45

Pro Lys His Gly Thr Asp Phe Leu Glu Tyr Lys Cys Arg Tyr Cys Cys
    50                  55                  60

Ser Val Ala Val Phe Phe Cys Phe Gly Thr Thr His Phe Cys Asn Pro
65                  70                  75                  80

Cys His Asp Asp Phe Gln Arg Val Thr Asn Leu Pro Lys Asn Glu Leu
                85                  90                  95

Pro Gln Cys Pro Ala Gly Pro Lys Ala Lys Gln Leu Asp Gly Glu Glu
            100                 105                 110

Cys Pro Leu His Val Lys His Pro Pro Thr Gly Glu Glu Phe Ala Leu
        115                 120                 125

Gly Cys Gly Val Cys Arg Asn Ala
    130                 135


<210> SEQ ID NO 30
<211> LENGTH: 137
<212> TYPE: PRT
<213> ORGANISM: Ooceraea biroi

<400> SEQUENCE: 30

Arg Tyr Ala Tyr Tyr Val Cys Tyr Lys Cys Gln Lys Ala Tyr Tyr Gly
1               5                   10                  15

Gly Glu Ala Arg Cys Asp Ala Gln Leu Gly Gly Glu Ser Phe Asp Pro
            20                  25                  30

Ala Glu Leu Val Cys Gly Gly Cys Ser Asp Val Ala Arg Ala Gln Met
        35                  40                  45

Cys Pro Lys His Gly Ala Asp Phe Leu Glu Tyr Lys Cys Arg Tyr Cys
    50                  55                  60

Cys Ser Val Ala Val Phe Phe Cys Phe Gly Thr Thr His Phe Cys Lys
65                  70                  75                  80
```

-continued

```
Pro Cys His Asp Asp Phe Gln Arg Val Thr Thr Ile Pro Lys Ser Glu
                85                  90                  95

Leu Pro Met Cys Pro Ala Gly Pro Lys Ala Lys Gln Leu Glu Gly Asp
            100                 105                 110

Glu Cys Pro Leu His Val Lys His Pro Pro Thr Gly Glu Glu Phe Ala
        115                 120                 125

Leu Gly Cys Gly Ile Cys Arg Asn Ala
    130                 135


<210> SEQ ID NO 31
<211> LENGTH: 136
<212> TYPE: PRT
<213> ORGANISM: Lutzomyia longipalpis

<400> SEQUENCE: 31

Arg Tyr Ala Tyr Tyr Val Cys Tyr Lys Cys Gln Lys Ala Tyr Tyr Gly
1               5                   10                  15

Gly Glu Ala Arg Cys Asp Ala Glu Ile Gly Asp Asn Phe Asp Pro Gln
            20                  25                  30

Glu Leu Val Cys Gly Gly Cys Ser Asp Val Ala Arg Ala Gln Met Cys
        35                  40                  45

Pro Lys His Gly Thr Asp Phe Leu Glu Tyr Lys Cys Arg Tyr Cys Cys
    50                  55                  60

Ser Val Ala Val Phe Phe Cys Phe Gly Thr Thr His Phe Cys Asp Thr
65                  70                  75                  80

Cys His Asp Asp Phe Gln Arg Leu Thr Asn Ile Pro Lys Asn Lys Leu
                85                  90                  95

Pro Arg Cys Pro Ala Gly Pro Lys Ala Lys Gln Leu Leu Gly Glu Asp
            100                 105                 110

Cys Pro Leu His Ile Ala His Pro Ala Thr Gly Glu Glu Phe Ala Leu
        115                 120                 125

Gly Cys Gly Ile Cys Arg Asn Ala
    130                 135


<210> SEQ ID NO 32
<211> LENGTH: 136
<212> TYPE: PRT
<213> ORGANISM: Drosophila melanogaster

<400> SEQUENCE: 32

Arg Tyr Ala Tyr Tyr Val Cys Phe Lys Cys Gln Lys Ala Tyr Tyr Gly
1               5                   10                  15

Gly Glu Ala Arg Cys Asp Ala Glu Ile Gly Glu Lys Phe Asp Pro Glu
            20                  25                  30

Glu Leu Val Cys Gly Gly Cys Ser Asp Val Ala Arg Ala Gln Met Cys
        35                  40                  45

Pro Lys His Gly Thr Asp Phe Leu Glu Tyr Lys Cys Arg Tyr Cys Cys
    50                  55                  60

Ser Val Ala Val Phe Phe Cys Phe Gly Thr Thr His Phe Cys Asp Thr
65                  70                  75                  80

Cys His Asp Asp Phe Gln Arg Leu Thr Asn Ile Pro Lys Val Lys Leu
                85                  90                  95

Pro Gln Cys Pro Ala Gly Pro Lys Ala Lys Gln Leu Leu Gly Asp Glu
            100                 105                 110

Cys Pro Leu His Val Met His Pro Pro Thr Gly Glu Glu Phe Ala Leu
        115                 120                 125
```

```
Gly Cys Gly Val Cys Arg Asn Ala
    130                 135


<210> SEQ ID NO 33
<211> LENGTH: 136
<212> TYPE: PRT
<213> ORGANISM: Aedes albopictus

<400> SEQUENCE: 33

Arg Tyr Ala Tyr Tyr Val Cys Ser Gln Cys Glu Lys Ala Tyr Tyr Gly
1               5                   10                  15

Gly Glu Ala Arg Cys Asp Ala Glu Leu Gly Glu Asn Tyr Asn Pro Gln
            20                  25                  30

Glu Leu Val Cys Gly Gly Cys Ser Asp Val Val Lys Ala Lys Met Cys
        35                  40                  45

Pro Lys His Gly Thr Asp Phe Leu Glu Tyr Lys Cys Arg Tyr Cys Cys
    50                  55                  60

Ser Val Ala Val Phe Phe Cys Phe Gly Thr Thr His Phe Cys Asp Thr
65                  70                  75                  80

Cys His Asp Asp Phe Gln Arg Leu Thr Asn Ile Pro Lys Asn Lys Leu
                85                  90                  95

Pro Lys Cys Pro Ala Gly Pro Lys Ala Lys Gln Leu Ile Gly Glu Glu
            100                 105                 110

Cys Pro Leu His Val Ile His Pro Pro Thr Gly Glu Glu Phe Ala Leu
        115                 120                 125

Gly Cys Gly Ile Cys Arg Asn Ala
    130                 135


<210> SEQ ID NO 34
<211> LENGTH: 136
<212> TYPE: PRT
<213> ORGANISM: Anopheles albimanus

<400> SEQUENCE: 34

Arg Tyr Ala Tyr Tyr Val Cys Ser Gln Cys Gly Lys Ala Tyr Tyr Gly
1               5                   10                  15

Gly Glu Ala Arg Cys Asp Ala Glu Leu Gly Glu Asn Phe Asn Pro Gln
            20                  25                  30

Glu Leu Val Cys Gly Gly Cys Ser Asp Val Ser Lys Ala Lys Met Cys
        35                  40                  45

Pro Lys His Gly Met Asp Phe Leu Glu Tyr Lys Cys Arg Tyr Cys Cys
    50                  55                  60

Ser Val Ala Val Phe Phe Cys Phe Gly Thr Thr His Phe Cys Asp Thr
65                  70                  75                  80

Cys His Asp Asp Phe Gln Arg Leu Thr Asn Leu Pro Lys Gly Lys Leu
                85                  90                  95

Pro Arg Cys Pro Ala Gly Pro Lys Ala Thr Gln Leu Thr Gly Glu Glu
            100                 105                 110

Cys Pro Leu His Val Val His Pro Pro Thr Gly Glu Glu Phe Ala Leu
        115                 120                 125

Gly Cys Gly Ile Cys Arg Asn Ala
    130                 135


<210> SEQ ID NO 35
<211> LENGTH: 136
<212> TYPE: PRT
<213> ORGANISM: Clunio marinus
```

<400> SEQUENCE: 35

```
Arg Tyr Ala Tyr Tyr Val Cys Cys Lys Cys Gln Lys Ala Tyr Tyr Gly
1               5                   10                  15

Gly Glu Ala Arg Cys Asp Val Glu Met Ala Glu Asn Phe Asn Pro Glu
            20                  25                  30

Glu Leu Val Cys Gly Gly Cys Ser Asp Ile Ala Lys Ala Gln Met Cys
        35                  40                  45

Pro Lys His Gly Met Asp Phe Leu Glu Tyr Lys Cys Arg Tyr Cys Cys
    50                  55                  60

Ser Val Ala Val Phe Phe Cys Phe Gly Thr Thr His Phe Cys Asp Thr
65                  70                  75                  80

Cys His Asp Asp Phe Gln Arg Leu Thr Asn Ile Pro Lys Ile Lys Leu
                85                  90                  95

Pro Lys Cys Pro Ala Gly Pro Lys Ala Met Gln Leu Met Thr Asp Glu
            100                 105                 110

Cys Pro Leu His Ile Val His Pro Pro Thr Gly Glu Glu Phe Ala Leu
        115                 120                 125

Gly Cys Gly Ile Cys Arg Asn Phe
    130                 135
```

<210> SEQ ID NO 36
<211> LENGTH: 136
<212> TYPE: PRT
<213> ORGANISM: Dendroctonus ponderosae

<400> SEQUENCE: 36

```
Arg Tyr Ala Tyr Tyr Val Cys Phe Lys Cys Asn Lys Ala Tyr Tyr Gly
1               5                   10                  15

Gly Glu Ala Arg Cys Asp Ala Asp Ala Gly Asp Ser Tyr Asp Pro Ala
            20                  25                  30

Glu Leu Val Cys Gly Ala Cys Ser Asp Val Ala Arg Ala Gln Met Cys
        35                  40                  45

Pro Lys His Gly Ala Asp Phe Leu Glu Tyr Lys Cys Arg Tyr Cys Cys
    50                  55                  60

Ser Val Ala Val Phe Phe Cys Phe Gly Thr Thr His Phe Cys Asn Pro
65                  70                  75                  80

Cys His Asp Asp Phe Gln Arg Val Thr Ile Leu Ser Lys Gly Glu Leu
                85                  90                  95

Pro Val Cys Pro Ala Gly Pro Arg Ala Thr Gln Leu Glu Gly Asp Glu
            100                 105                 110

Cys Pro Leu His Val Lys His Pro Ala Thr Gly Glu Glu Phe Ala Leu
        115                 120                 125

Gly Cys Gly Val Cys Arg Asn Ala
    130                 135
```

<210> SEQ ID NO 37
<211> LENGTH: 137
<212> TYPE: PRT
<213> ORGANISM: Diaphorina citri

<400> SEQUENCE: 37

```
Lys Tyr Ala Tyr Tyr Val Cys Phe Arg Cys Asn Lys Ala Tyr Tyr Gly
1               5                   10                  15

Gly Glu Ala Arg Cys Asp Ala Glu Leu Gly Ala Ser Asp Tyr Asn Pro
            20                  25                  30

Ala Glu Leu Val Cys Gly Ala Cys Ser Asp Val Ser Arg Ala Gln Met
```

```
        35                  40                  45

Cys Pro Lys His Gly Gln Asp Phe Leu Glu Tyr Lys Cys Arg Tyr Cys
    50                  55                  60

Cys Ser Val Ala Val Phe Phe Cys Phe Gly Thr Thr His Phe Cys Asn
65                  70                  75                  80

Ala Cys His Glu Asp Phe Gln Arg Val Thr Asn Ile Val Thr Thr Gln
                85                  90                  95

Leu Pro Tyr Cys Pro Ala Gly Pro Lys Ala Val Gln Leu Glu Gly Asp
            100                 105                 110

Glu Cys Pro Leu His Val Glu His Pro Ala Thr Gly Glu Glu Phe Ala
        115                 120                 125

Leu Gly Cys Gly Ile Cys Arg Asn Ala
    130                 135


<210> SEQ ID NO 38
<211> LENGTH: 137
<212> TYPE: PRT
<213> ORGANISM: Acyrthosiphon pisum

<400> SEQUENCE: 38

Lys Tyr Ala Tyr Tyr Val Cys Phe Lys Cys Thr Lys Ala Tyr Tyr Gly
1               5                   10                  15

Gly Glu Ala Arg Cys Glu Leu Asp Val Gly Gly Thr Asp Tyr Asp Pro
            20                  25                  30

Ala Glu Leu Val Cys Gly Gly Cys Ser Asp Val Ala Arg Ala Gln Met
        35                  40                  45

Cys Pro Lys His Gly Thr Asp Leu Leu Glu Tyr Lys Cys Arg Tyr Cys
    50                  55                  60

Cys Ser Val Ala Val Phe Phe Cys Phe Gly Thr Thr His Phe Cys Asn
65                  70                  75                  80

Ala Cys His Asp Asp Phe Gln Arg Val Thr Asn Leu Leu Pro Gln Glu
                85                  90                  95

Leu Pro Pro Cys Pro Ala Gly Pro Arg Ala Thr Ala Leu Asn Val Asp
            100                 105                 110

Glu Cys Pro Leu His Val Lys His Pro Pro Thr Gly Glu Glu Phe Ala
        115                 120                 125

Leu Gly Cys Gly Val Cys Arg Asn Ala
    130                 135


<210> SEQ ID NO 39
<211> LENGTH: 138
<212> TYPE: PRT
<213> ORGANISM: Monosiga brevicollis

<400> SEQUENCE: 39

Lys Tyr Ala Tyr Phe Pro Cys Tyr Lys Cys Lys Gln Pro Tyr Phe Gly
1               5                   10                  15

Gly Asp Ala Ala Cys Glu Ala Gly Arg Gly Ala Ala Glu Tyr Asp Pro
            20                  25                  30

Ser Glu Leu Ile Cys Pro Leu Cys Val Gly Gly Gly Ala Ala Gln Gln
        35                  40                  45

Ile Cys Ala Lys His Gly Glu Asp Phe Leu Glu Tyr Lys Cys Arg Tyr
    50                  55                  60

Cys Cys Ser Val Ala Val Phe Phe Cys Phe Gly Thr Thr His Phe Cys
65                  70                  75                  80

Asn Thr Cys His Asp Asp Tyr Arg Arg Cys Thr Glu Cys Pro Lys Glu
```

```
                85                  90                  95

Asp Leu Pro His Cys Pro Cys Gly Pro Val Leu Thr Gln Leu Glu Gly
            100                 105                 110

Asp Glu Cys Pro Leu His Val Lys His Pro Pro Thr Gly Glu Glu Phe
        115                 120                 125

Ala Leu Gly Cys Gly Val Cys Arg Asn Ala
    130                 135


<210> SEQ ID NO 40
<211> LENGTH: 137
<212> TYPE: PRT
<213> ORGANISM: Salpingoeca rosetta

<400> SEQUENCE: 40

Lys Tyr Ala Tyr Phe Pro Cys His Lys Cys Gly Lys Ala Tyr Phe Gly
1               5                   10                  15

Gly Ala Ala Ala Cys Glu Ala Gly Arg Gly Ser Ala Asp Phe Asp Pro
            20                  25                  30

Thr Glu Leu Val Cys Pro Leu Cys Val Gly Gly Ala Ala Thr Gln Ile
        35                  40                  45

Cys Arg Lys His Gly Thr Glu Phe Leu Glu Tyr Lys Cys Arg Tyr Cys
    50                  55                  60

Cys Ser Val Ala Val Phe Phe Cys Phe Gly Thr Thr His Phe Cys Asn
65                  70                  75                  80

Ala Cys His Asp Gln Tyr Gln Arg Cys Gln Ser Thr Pro Lys Glu Leu
                85                  90                  95

Leu Pro Gln Cys Pro Ala Gly Pro Cys Leu Thr Gln Leu Glu Gly Asp
            100                 105                 110

Glu Cys Pro Leu His Val Lys His Pro Pro Thr Gly Glu Glu Phe Ala
        115                 120                 125

Leu Gly Cys Gly Leu Cys Arg Asn Ala
    130                 135


<210> SEQ ID NO 41
<211> LENGTH: 135
<212> TYPE: PRT
<213> ORGANISM: Salpingoeca rosetta

<400> SEQUENCE: 41

Lys Tyr Thr Tyr Tyr Lys Cys Phe Lys Cys Ser Lys Ala Tyr Phe Gly
1               5                   10                  15

Gly Glu Glu Ala Cys Ala Val Gly Ser Asn Asp Phe Asp Glu Glu Glu
            20                  25                  30

Leu Val Cys Pro Ala Cys Ser Gly Gly Glu Ala Gln Gln Val Cys Pro
        35                  40                  45

Lys His Gly Thr Asp Phe Leu Glu Tyr Lys Cys Arg Tyr Cys Cys Ser
    50                  55                  60

Val Ala Val Phe Phe Cys Phe Gly Thr Thr His Phe Cys Gln Pro Cys
65                  70                  75                  80

His Asp Asp Tyr Gln Arg Cys Leu Asp Cys Pro Lys Ala Asn Leu Pro
                85                  90                  95

Lys Cys Pro Ala Gly Pro Lys Leu Thr Gln Leu Glu Gly Glu Glu Cys
            100                 105                 110

Pro Leu His Val Lys His Pro Pro Thr Gly Glu Glu Phe Ala Leu Gly
        115                 120                 125

Cys Gly Ile Cys Arg Asn Ala
```

```
    130                 135


<210> SEQ ID NO 42
<211> LENGTH: 136
<212> TYPE: PRT
<213> ORGANISM: Polysphondylium album

<400> SEQUENCE: 42

Gln Phe Ala Tyr Tyr Leu Cys Phe Lys Cys Lys Gln Pro Tyr Phe Gly
1               5                   10                  15

Gly Ser Asn Gln Cys Ala Ala Ala Met Ala Ala Pro Glu Lys Phe Asn
            20                  25                  30

Pro Glu Glu Leu Ile Cys Gly Gly Cys Ser Ser Asp Asp Val Leu Pro
        35                  40                  45

Ile Cys Pro Lys His Gly Lys Asp Tyr Leu Glu Phe Lys Cys Arg Tyr
    50                  55                  60

Cys Cys Ser Val Ala Ile Trp Phe Cys Phe Gly Thr His His Phe Cys
65                  70                  75                  80

Glu Thr Cys His Asn His His Thr Glu Leu Thr Ser Arg Asn Thr His
                85                  90                  95

Pro Gln Cys Pro Val Gly Pro Gly Gly Ile Glu Leu Pro Gly Asp Asp
            100                 105                 110

Cys Pro Leu His Val Asp His Pro Lys Thr Gly Thr Glu Phe Ala Leu
        115                 120                 125

Gly Cys Gly Ile Cys Arg Asn Val
    130                 135


<210> SEQ ID NO 43
<211> LENGTH: 136
<212> TYPE: PRT
<213> ORGANISM: Dictyostelium purpureum

<400> SEQUENCE: 43

His Phe Ser Tyr Tyr Leu Cys Phe Lys Cys Lys Gln Pro Tyr Phe Gly
1               5                   10                  15

Gly Thr Asn Gln Cys Val Ala Gly Ala Ala Ala Gln Asn Phe Asn Pro
            20                  25                  30

Glu Glu Leu Ile Cys Gly Gly Cys Ser Ser Gly Asp Asn Pro Ser Ser
        35                  40                  45

Ile Cys Pro Lys His Gly Lys Asp Tyr Leu Glu Phe Lys Cys Arg Tyr
    50                  55                  60

Cys Cys Ser Val Ala Ile Trp Phe Cys Phe Gly Thr Thr His Phe Cys
65                  70                  75                  80

Glu Ser Cys His Asn Asn His Thr Thr Leu Ser Asp Lys Lys Lys His
                85                  90                  95

Pro Gln Cys Pro Val Gly Pro Gly Gly Ile Glu Leu Ser Gly Asp Val
            100                 105                 110

Cys Pro Leu Lys Val Asp His Pro Pro Thr Gly Lys Glu Phe Ala Leu
        115                 120                 125

Gly Cys Gly Ile Cys Arg Glu Ser
    130                 135


<210> SEQ ID NO 44
<211> LENGTH: 137
<212> TYPE: PRT
<213> ORGANISM: Dictyostelium discoideum

<400> SEQUENCE: 44
```

```
Gln Phe Ser Tyr Tyr Leu Cys Phe Lys Cys Lys Gln Pro Tyr Phe Gly
1               5                   10                  15

Gly Leu Asn Gln Cys Ala Ala Ala Ala Ala Leu Pro Ser Asn Phe Asn
            20                  25                  30

Pro Glu Glu Leu Ile Cys Gly Gly Cys Ser Ser Gly Asp Asp Pro Gln
        35                  40                  45

Ser Ile Cys Pro Lys His Gly Lys Asp Tyr Leu Glu Phe Lys Cys Arg
    50                  55                  60

Tyr Cys Cys Ser Val Ala Val Trp Phe Cys Phe Gly Thr Thr His Phe
65                  70                  75                  80

Cys Asp Thr Cys His Asp Asn Asn Gly Arg Leu Thr Ala Gln Thr Lys
                85                  90                  95

Phe Gly Gln Cys Pro Leu Gly Pro Gly Ser Val Glu Leu Pro Lys Gly
            100                 105                 110

Pro Cys Pro Leu Gly Leu Lys His Tyr Glu Ala Gly Lys Glu Gln Ala
        115                 120                 125

Leu Gly Cys Gly Val Cys Arg Asn Val
    130                 135
```

<210> SEQ ID NO 45
<211> LENGTH: 137
<212> TYPE: PRT
<213> ORGANISM: Tieghemostelium lacteum

<400> SEQUENCE: 45

```
Gln Phe Ala Phe Tyr Leu Cys Phe Lys Cys Lys Lys Pro Tyr Tyr Gly
1               5                   10                  15

Gly Ala Asn Val Cys Ala Asn Asn Val Ala Gln Pro Met Asn Phe Asn
            20                  25                  30

Pro Glu Glu Leu Ile Cys Ser Asn Cys Thr Thr Glu Asp Gly Asn Thr
        35                  40                  45

Ser Ile Cys Pro Lys His Gly Lys Glu Phe Leu Glu Tyr Lys Cys Arg
    50                  55                  60

Tyr Cys Cys Ser Val Ser Ile Trp Arg Cys Phe Gly Thr Thr Ser Phe
65                  70                  75                  80

Cys Glu Thr Cys His Asn Arg Asn His Glu Leu Thr Ser Arg Lys Lys
                85                  90                  95

His Pro Lys Cys Pro Val Gly Pro Gly Gly Val Glu Leu Pro Gly Glu
            100                 105                 110

Val Cys Pro Leu Gly Leu Glu His Pro Pro Thr Gly Gln Glu Phe Ala
        115                 120                 125

Ile Gly Cys Gly Leu Cys Arg Asn Thr
    130                 135
```

<210> SEQ ID NO 46
<211> LENGTH: 136
<212> TYPE: PRT
<213> ORGANISM: Cavenderia fasciculata

<400> SEQUENCE: 46

```
Gln Phe Ser Tyr Tyr Leu Cys Phe Lys Cys Lys Lys Pro Tyr Phe Gly
1               5                   10                  15

Gly Met Asn Gln Cys Ala Ala Gly Leu Val Val Pro Asp Lys Ile Asn
            20                  25                  30

Glu Gln Asp Leu Ile Cys Gly Ser Cys Ser Ser Asn Asp Ser Val Thr
        35                  40                  45
```

Ile Cys Pro Lys His Gly Lys Asp Tyr Leu Glu Tyr Lys Cys Arg Tyr
    50                  55                  60

Cys Cys Ser Pro Ser Val Trp Phe Cys Phe Gly Thr Thr Arg Phe Cys
65                  70                  75                  80

Ser Leu Cys His Asp Lys His Ala Glu Leu Thr Ser Arg Ser Lys His
                85                  90                  95

Pro Lys Cys Pro Val Ala Pro Gly Gly Ile Glu Met Pro Gly Asp Ile
            100                 105                 110

Cys Pro Leu Gly Ile Asp His Pro Pro Thr Gly Glu Glu Phe Ser Leu
        115                 120                 125

Gly Cys Gly Leu Cys Lys Tyr Asn
    130                 135

<210> SEQ ID NO 47
<211> LENGTH: 139
<212> TYPE: PRT
<213> ORGANISM: Thecamonas trahens

<400> SEQUENCE: 47

Arg Phe Ala Tyr Tyr Gln Cys Tyr Glu Cys Lys Glu Pro Tyr Tyr Gly
1               5                   10                  15

Gly Ala Val Ala Cys Glu Ala Ala Gly Arg Gly Gly Asp Phe Asp Glu
            20                  25                  30

Thr Glu Leu Val Cys Gly Gly Cys Val Gly Arg Arg Ile Gly Ala Thr
        35                  40                  45

Ala Cys Ser Lys His Gly Met Asp Asn Met Val Phe Ala Cys Arg Tyr
    50                  55                  60

Cys Cys Ser Val Ala Val Trp Phe Cys Phe Gly Thr Thr His Phe Cys
65                  70                  75                  80

Asp Thr Cys His Ser Asn Val Gly Gly Val Gln Ala Ala Ala Ala Ser
                85                  90                  95

Glu Asp Arg Pro Val Cys Pro Val Gly Pro Gly Cys Lys Gln Leu Pro
            100                 105                 110

Pro Gly Pro Cys Pro Leu Gly Leu Lys Glu Pro Pro Val Gly Glu Glu
        115                 120                 125

Leu Cys Leu Gly Cys Gly Leu Cys Ala Glu Ala
    130                 135

<210> SEQ ID NO 48
<211> LENGTH: 143
<212> TYPE: PRT
<213> ORGANISM: Schmidtea mediterranea

<400> SEQUENCE: 48

Lys Tyr Cys Tyr Tyr Leu Cys Tyr Lys Cys Lys Asn Ser Tyr Tyr Gly
1               5                   10                  15

Gly Glu Ala Arg Cys Glu Pro Asp Met Leu Leu Asn Thr Gln Val Asn
            20                  25                  30

Asn Ser Pro Val Met Asp Pro Ala Thr Glu Leu Cys Cys Ala Ala Cys
        35                  40                  45

Ser Asp Val Ala Gln Ala Lys Ile Cys Pro Lys His Ser Thr Asp Phe
    50                  55                  60

Leu Glu Tyr Lys Cys Arg Tyr Cys Cys Ser Ile Ala Val Phe Phe Cys
65                  70                  75                  80

Phe Gly Thr Thr His Phe Cys Gln Arg Cys His Asp Asn Leu Asp Thr
                85                  90                  95

```
Val Leu Lys Ala Pro Trp Leu Pro Gln Cys Pro Ala Gly Pro Ala Leu
            100                 105                 110

Gln His Leu Ser Thr Pro Glu Cys Pro Leu His Val Ile His Pro Pro
        115                 120                 125

Thr Gly Glu Glu Phe Ala Leu Gly Cys Ala Leu Cys Arg Lys Leu
    130                 135                 140


<210> SEQ ID NO 49
<211> LENGTH: 137
<212> TYPE: PRT
<213> ORGANISM: Brugia malayi

<400> SEQUENCE: 49

Arg Tyr Met Tyr Val Leu Cys Phe Lys Cys Gly Lys Ala Tyr Phe Gly
1               5                   10                  15

Gly Glu Ser Arg Cys Gln Gln Glu Leu Asp Asn Ser Gln Tyr Asn Pro
            20                  25                  30

Glu Glu Leu Ile Cys Gly Gly Cys Ser Asp Val Val Gly Ala Gln Val
        35                  40                  45

Cys Gly Arg His Gly Ile Asp Phe Leu Glu Phe Lys Cys Arg Phe Cys
    50                  55                  60

Cys Ser Val Ala Val Tyr Phe Cys Phe Gly Thr Thr His Phe Cys Thr
65                  70                  75                  80

Ala Cys His Asp Asp Phe Gln Arg Leu Val Cys Leu Pro Lys Lys Leu
                85                  90                  95

Leu Pro Lys Cys Pro Val Gly Pro Lys Cys Val Gln Leu Asp Gly Ser
            100                 105                 110

Glu Cys Pro Leu Arg Val Lys His Pro Pro Thr Gly Glu Glu Phe Pro
        115                 120                 125

Leu Gly Cys Gly Ile Cys Arg Asn Ile
    130                 135


<210> SEQ ID NO 50
<211> LENGTH: 137
<212> TYPE: PRT
<213> ORGANISM: Thelazia callipaeda

<400> SEQUENCE: 50

Arg Tyr Met Tyr Val Leu Cys Phe Lys Cys Gly Lys Ala Tyr Phe Gly
1               5                   10                  15

Gly Glu Ser Arg Cys Gln Gln Glu Val Asp Asn Ser Gln Tyr Asn Ala
            20                  25                  30

Glu Glu Leu Ile Cys Gly Gly Cys Ser Asp Val Val Gly Ala Gln Ile
        35                  40                  45

Cys Gly Arg His Gly Val Asp Phe Leu Glu Tyr Lys Cys Arg Phe Cys
    50                  55                  60

Cys Ser Val Ala Val Tyr Phe Cys Phe Gly Thr Thr His Phe Cys Thr
65                  70                  75                  80

Ser Cys His Asp Asp Phe Gln Arg Leu Ile Arg Leu Pro Met Lys Leu
                85                  90                  95

Leu Pro Lys Cys Pro Val Gly Pro Arg Ala Ile Gln Leu Asp Gly Asn
            100                 105                 110

Glu Cys Pro Leu Lys Ile Lys His Pro Pro Thr Gly Glu Glu Phe Ala
        115                 120                 125

Leu Gly Cys Gly Val Cys Arg Asn Ile
    130                 135
```

<210> SEQ ID NO 51
<211> LENGTH: 137
<212> TYPE: PRT
<213> ORGANISM: Toxocara canis

<400> SEQUENCE: 51

Arg Tyr Met Tyr Val Leu Cys Phe Lys Cys Gly Lys Ala Tyr Phe Gly
1 5 10 15

Gly Glu Ser Arg Cys Gln Gln Ala Leu Asp Asn Ser Gln Tyr Asn Pro
20 25 30

Glu Glu Leu Leu Cys Gly Gly Cys Ser Asp Val Val Gly Ala Gln Val
35 40 45

Cys Gly Arg His Gly Val Asp Tyr Leu Glu Tyr Lys Cys Arg Phe Cys
50 55 60

Cys Ser Val Ala Val Tyr Phe Cys Phe Gly Thr Thr His Phe Cys Ala
65 70 75 80

Ala Cys His Asp Asp Phe Gln Arg Leu Met Cys Leu Pro Lys Gln Leu
85 90 95

Leu Pro Lys Cys Pro Ala Gly Pro Lys Ala Val Gln Met Glu Gly Glu
100 105 110

Gly Cys Pro Leu Arg Leu Gln His Pro Pro Thr Gly Glu Glu Phe Ala
115 120 125

Met Gly Cys Gly Ile Cys Arg Asn Leu
130 135

<210> SEQ ID NO 52
<211> LENGTH: 137
<212> TYPE: PRT
<213> ORGANISM: Dracunculus medinensis

<400> SEQUENCE: 52

Arg Tyr Met Tyr Val Gln Cys Phe Lys Cys Asn Lys Ala Tyr Phe Gly
1 5 10 15

Gly Glu Ser Arg Cys Gln Gln Ala Leu Asp Asp Ser His Tyr Asn Pro
20 25 30

Glu Glu Leu Val Cys Gly Gly Cys Ser Asp Val Val Gly Ala Gln Val
35 40 45

Cys Gly Arg His Gly Met Asp Tyr Leu Glu Tyr Lys Cys Arg Phe Cys
50 55 60

Cys Ser Val Ala Val Tyr Phe Cys Phe Gly Thr Thr His Phe Cys Ala
65 70 75 80

Ala Cys His Asp Glu Phe Gln Arg Leu Met Cys Leu Pro Lys Gln Leu
85 90 95

Leu Pro Lys Cys Pro Val Gly Pro Lys Gly Met Gln Leu Glu Gly Gly
100 105 110

Ala Cys Pro Leu Lys Ile Gln His Pro Pro Thr Gly Glu Glu Phe Ala
115 120 125

Leu Gly Cys Gly Ile Cys Arg Asn Leu
130 135

<210> SEQ ID NO 53
<211> LENGTH: 137
<212> TYPE: PRT
<213> ORGANISM: Steinernema glaseri

<400> SEQUENCE: 53

-continued

```
Arg Tyr Met Tyr Val Leu Cys Phe Lys Cys Asn Lys Ala Tyr Phe Gly
1               5                   10                  15

Gly Glu Ser Arg Cys Gln Glu Ala Leu Glu Ser Ser Gln Tyr Asn Pro
            20                  25                  30

Glu Glu Leu Ile Cys Gly Gly Cys Ser Asp Thr Thr Gly Ala Gln Val
        35                  40                  45

Cys Ala Arg His Gly Val Asp Tyr Leu Glu Phe Lys Cys Arg Phe Cys
    50                  55                  60

Cys Ser Val Ala Val Tyr Phe Cys Phe Gly Thr Thr His Phe Cys Ala
65                  70                  75                  80

Ser Cys His Asp Asp Phe Gln Arg Leu Met Cys Leu Pro Lys His Leu
                85                  90                  95

Leu Pro Ala Cys Pro Ala Gly Pro Lys Ala Thr Lys Leu Glu Thr Asp
            100                 105                 110

Gly Cys Pro Leu Lys Ile Ala His Pro Pro Ser Gly Glu Glu Phe Ala
        115                 120                 125

Leu Gly Cys Gly Val Cys Arg Asn Leu
    130                 135


<210> SEQ ID NO 54
<211> LENGTH: 137
<212> TYPE: PRT
<213> ORGANISM: Caenorhabditis elegans

<400> SEQUENCE: 54

Arg Tyr Met Tyr Val Leu Cys His Lys Cys Lys Lys Ala Tyr Phe Gly
1               5                   10                  15

Gly Glu Ser Arg Cys Gln Ala Ala Leu Asp Ser Ser Gln Phe Asn Pro
            20                  25                  30

Glu Glu Leu Leu Cys Gly Gly Cys Ser Asp Thr Ser Gly Val Gln Val
        35                  40                  45

Cys Pro Arg His Gly Val Glu Tyr Leu Glu Tyr Lys Cys Arg Phe Cys
    50                  55                  60

Cys Ser Ile Ala Val Tyr Phe Cys Phe Gly Thr Thr His Phe Cys Ala
65                  70                  75                  80

Pro Cys His Asp Asp Phe Gln Arg Leu Met Ser Leu Pro Lys His Leu
                85                  90                  95

Leu Pro Thr Cys Pro Val Gly Pro Arg Ser Thr Pro Met Glu Glu Gln
            100                 105                 110

Thr Cys Pro Leu Lys Met Lys His Pro Pro Thr Gly Asp Glu Phe Ala
        115                 120                 125

Met Gly Cys Gly Ile Cys Arg Asn Ile
    130                 135


<210> SEQ ID NO 55
<211> LENGTH: 136
<212> TYPE: PRT
<213> ORGANISM: Ancylostoma ceylanicum

<400> SEQUENCE: 55

Arg Tyr Met Tyr Val Leu Cys Asn Val Cys Asn Lys Ala Tyr Phe Gly
1               5                   10                  15

Gly Glu Ser Arg Cys Gln Met Ala Leu Gln Ser Phe Gln Tyr Asn Ala
            20                  25                  30

Ala Glu Leu Val Cys Gly Gly Cys Ser Ala Pro Ala Gly Thr Glu Val
        35                  40                  45
```

-continued

```
Cys Gly Arg His Gly Ala Glu Tyr Leu Glu Tyr Lys Cys Arg Tyr Cys
    50                  55                  60

Cys Ser Ile Ala Val Tyr Phe Cys Phe Gly Thr Thr His Phe Cys Ala
65                  70                  75                  80

Ala Cys His Asp Asp Phe Gln Arg Leu Val Cys Leu Pro Arg Asn Gln
                85                  90                  95

Phe Pro Pro Cys Pro Thr Gly Pro Arg Ala Thr Pro Gly Glu Gly Pro
            100                 105                 110

Cys Pro Leu Arg Arg Pro His Pro Pro Ala Gly Glu Glu Phe Ala Leu
        115                 120                 125

Gly Cys Gly Ile Cys Arg Asn Ile
    130                 135


<210> SEQ ID NO 56
<211> LENGTH: 136
<212> TYPE: PRT
<213> ORGANISM: Enterobius vermicularis

<400> SEQUENCE: 56

Arg Tyr Val Tyr Val Leu Cys Phe Lys Cys Gly Lys Ala Tyr Phe Gly
1               5                   10                  15

Gly Glu Ser Arg Cys Gln Gln Ala Phe Asp Tyr Ser Gln Phe Asn Glu
            20                  25                  30

Thr Glu Leu Leu Cys Gly Ala Cys Ser Asp Val Asn Arg Ala Gln Val
        35                  40                  45

Cys Gly Arg His Gly Val Glu Tyr Leu Glu Tyr Lys Cys Arg Phe Cys
    50                  55                  60

Cys Ser Val Ala Val Tyr Phe Cys Phe Gly Thr Thr His Phe Cys Ala
65                  70                  75                  80

Val Cys His Asp Asp Phe Gln Arg Leu Met Arg Leu Pro Lys Asn Leu
                85                  90                  95

Leu Pro Lys Cys Pro Ala Gly Pro Lys Gly Leu Gln Leu Glu Gly Ser
            100                 105                 110

Cys Pro Leu Arg Ile Ser His Pro Pro Thr Gly Glu Glu Phe Ala Leu
        115                 120                 125

Gly Cys Gly Ile Cys Arg Asn Leu
    130                 135


<210> SEQ ID NO 57
<211> LENGTH: 137
<212> TYPE: PRT
<213> ORGANISM: Bursaphelenchus xylophilus

<400> SEQUENCE: 57

Arg Tyr Val Tyr Val Leu Cys Ser Lys Cys Asn Lys Ala Tyr Phe Gly
1               5                   10                  15

Gly Glu Ser Arg Cys Gln Gln Ala Leu Asp Ser Ser Ser Tyr Lys Pro
            20                  25                  30

Glu Glu Leu Val Cys Gly Gly Cys Ser Asp Ile Ser Gly Ala Pro Val
        35                  40                  45

Cys Gly Arg His Gly Thr Glu Phe Leu Glu Tyr Lys Cys Arg Phe Cys
    50                  55                  60

Cys Ser Val Ala Val Tyr Phe Cys Phe Gly Asn Ser His Phe Cys Ser
65                  70                  75                  80

Ile Cys His Ser Asp Phe Gln Arg Leu Ile Ala Thr Pro Thr Asn Leu
                85                  90                  95
```

-continued

```
Leu Pro Gln Cys Pro Val Gly Pro Arg Ala Thr Gln Leu Glu Asn Gln
            100                 105                 110

Asp Cys Pro Leu Arg Val Lys His Pro Pro Thr Gly Glu Glu Phe Ser
        115                 120                 125

Leu Gly Cys Gly Ile Cys Arg Asn Leu
    130                 135
```

<210> SEQ ID NO 58
<211> LENGTH: 144
<212> TYPE: PRT
<213> ORGANISM: Globodera pallida

<400> SEQUENCE: 58

```
Lys Tyr Met Tyr Val Gln Cys Ser Arg Cys Leu Lys Ala Tyr Phe Gly
1               5                   10                  15

Gly Glu Ser Gln Cys Gln Leu Gly Leu Glu Glu Val Gly Phe Gly Thr
            20                  25                  30

Glu Phe Asp Pro Ala Glu Leu Val Cys Gly Gly Cys Ala Ala Glu Met
        35                  40                  45

Gly His Asp Gly Ala Val Val Cys Glu Arg His Gly Thr Asp Phe Leu
    50                  55                  60

Glu Phe Lys Cys Arg Phe Cys Cys Ser Val Ala Val Tyr Phe Cys Phe
65                  70                  75                  80

Gly Thr Thr His Phe Cys Ala Ala Cys His Ser Asp Phe Gln Arg Leu
                85                  90                  95

Val Gln Leu Pro Arg His Ala Leu Pro Lys Cys Pro Val Ala Pro Arg
            100                 105                 110

Ala Val Gln Met Pro Asp Glu Pro Cys Pro Leu Arg Ile Ser His Pro
        115                 120                 125

Pro Thr Gly Glu Glu Phe Ala Leu Gly Cys Gly Ile Cys Arg Asn Leu
    130                 135                 140
```

<210> SEQ ID NO 59
<211> LENGTH: 142
<212> TYPE: PRT
<213> ORGANISM: Rhabditophanes sp. KR3021

<400> SEQUENCE: 59

```
Lys Tyr Met Tyr Val Leu Cys Phe Lys Cys Lys Arg Ala Tyr Phe Gly
1               5                   10                  15

Gly Asp Gly Ala Cys His Ala Ala Val Tyr Gly Glu Gly Asn Ser Gln
            20                  25                  30

Ile Pro Phe Asn Pro Glu Glu Leu Val Cys Gly Gly Cys Ser Asp Val
        35                  40                  45

Leu Gly Gly Ala Val Cys Thr Val His Gly Ser Asp Phe Met Glu Phe
    50                  55                  60

Lys Cys Arg Tyr Cys Cys Ser Val Ala Leu Phe Phe Cys Phe Gly Thr
65                  70                  75                  80

Thr His Phe Cys Val Ser Cys His Thr Asp Phe Gln Arg Leu Val Gly
                85                  90                  95

Val Pro Leu Ser Gln Leu Pro Gln Cys Pro Val Gly Pro Arg Ser Val
            100                 105                 110

Ala Ile Glu Gly Glu Lys Cys Pro Leu Asp Val Glu His Pro Pro Thr
        115                 120                 125

Gly Thr Glu Phe Ser Leu Gly Cys Gly Val Cys Lys Asn Leu
    130                 135                 140
```

<210> SEQ ID NO 60
<211> LENGTH: 145
<212> TYPE: PRT
<213> ORGANISM: Parastrongyloides trichosuri

<400> SEQUENCE: 60

```
Lys Phe Met Tyr Cys Leu Cys Phe Lys Cys Lys Lys Ala Tyr Tyr Gly
1               5                   10                  15

Gly Asp Ile Asn Cys His Gln Gln Leu Leu Gln Glu Asp Asn Glu Asn
            20                  25                  30

Arg Ile Asn Ile Val Phe Lys Pro Glu Glu Leu Val Cys Gly Gly Cys
        35                  40                  45

Ser Asn Val Ala Gly Gly Gly Ser Cys Lys Lys His Gly Thr Glu Tyr
    50                  55                  60

Ile Glu Tyr Lys Cys Arg Phe Cys Cys Ser Val Ala Val Tyr Phe Cys
65                  70                  75                  80

Phe Gly Thr Thr His Phe Cys Gln Val Cys His Ser Asp Phe Gln Arg
                85                  90                  95

Leu Met Val Leu Lys Pro Glu Glu Leu Pro Lys Cys Pro Val Gly Pro
            100                 105                 110

Lys Ala Thr Ser Leu Pro Val Asp Asp Cys Pro Leu Arg Ile Cys His
        115                 120                 125

Pro Asp Thr Gly Ile Glu Phe Ser Leu Gly Cys Gly Ala Cys Arg Asn
    130                 135                 140

Ile
145
```

<210> SEQ ID NO 61
<211> LENGTH: 145
<212> TYPE: PRT
<213> ORGANISM: Strongyloides ratti

<400> SEQUENCE: 61

```
Lys Phe Met Tyr Cys Leu Cys Tyr Lys Cys Gly Lys Ala Tyr Tyr Gly
1               5                   10                  15

Gly Asp Val Asn Cys His Gln Val Leu Leu Gln Glu Asp Asp Gly Asn
            20                  25                  30

Gln His Lys Ile Ile Phe Lys Pro Glu Glu Leu Ile Cys Gly Gly Cys
        35                  40                  45

Ser Asn Val Ala Gly Gly Gly Ser Cys Thr Lys His Gly Thr Glu Tyr
    50                  55                  60

Ile Glu Tyr Lys Cys Arg Phe Cys Cys Ser Val Ala Val Tyr Phe Cys
65                  70                  75                  80

Phe Gly Thr Thr His Phe Cys Gln Ile Cys His Ser Asp Phe Gln Arg
                85                  90                  95

Leu Met Ile Leu Lys Gly Asp Glu Leu Pro Asn Cys Pro Val Gly Pro
            100                 105                 110

Lys Ala Thr Pro Ile Lys Lys Asp Val Cys Pro Leu Lys Ile Asn His
        115                 120                 125

Pro Asp Thr Gly Ile Glu Phe Ser Leu Gly Cys Gly Ala Cys Arg Asn
    130                 135                 140

Ile
145
```

<210> SEQ ID NO 62
<211> LENGTH: 138

<212> TYPE: PRT
<213> ORGANISM: Trichinella nelsoni

<400> SEQUENCE: 62

Arg Tyr Ala Tyr Tyr Leu Cys Tyr Lys Cys Arg Arg Pro Tyr Phe Gly
1 5 10 15

Gly Leu Ala Gln Cys Gln Asp Asp Tyr Gly Gln Leu Ser Gly Tyr Asp
20 25 30

Glu Arg Glu Leu Leu Cys Gly Ala Cys Ser Asp Val Gln Gln Ala Lys
35 40 45

Val Cys Pro Arg His Gly Thr Asp Phe Leu Glu Tyr Lys Cys Arg Tyr
50 55 60

Cys Cys Ser Leu Ala Val Phe Phe Cys Phe Gly Thr Thr His Phe Cys
65 70 75 80

Thr Ser Cys His Asp Asp Phe Gln Arg Leu Leu His Ile Pro Lys Asp
85 90 95

Gln Leu Pro His Cys Pro Ala Gly Pro Gln Ala Arg Gln Leu Ser Gly
100 105 110

Asp Gln Cys Pro Leu Asn Val Asp His Pro Pro Thr Gly Glu Glu Tyr
115 120 125

Ala Leu Gly Cys Gly Ile Cys Arg Asn Ile
130 135

<210> SEQ ID NO 63
<211> LENGTH: 136
<212> TYPE: PRT
<213> ORGANISM: Danaus plexippus

<400> SEQUENCE: 63

Arg Tyr Ala Tyr Tyr Val Cys His Lys Cys Gly Lys Ala Tyr Phe Gly
1 5 10 15

Gly Leu Ala Arg Cys Glu Ala Glu Ser Asn Gly Trp Trp Glu Pro Ala
20 25 30

Glu Leu Val Cys Gly Ala Cys Ser Asp Val Ala Gly Ala Arg Thr Cys
35 40 45

Pro Lys His Gly Ala Asp Phe Leu Glu Tyr Lys Cys Arg Tyr Cys Cys
50 55 60

Ser Val Ala Val Phe Phe Cys Phe Gly Thr Ser His Phe Cys Asn Ala
65 70 75 80

Cys His Asp Asp Phe Gln Arg Val Thr Asn Ile Pro Arg His Leu Leu
85 90 95

Pro Gln Cys Pro Ala Gly Pro Lys Gly Glu Gln Leu Pro Gly Glu Glu
100 105 110

Cys Pro Leu His Val Gln His Pro Pro Thr Gly Glu Glu Phe Ala Leu
115 120 125

Gly Cys Gly Val Cys Arg His Ala
130 135

<210> SEQ ID NO 64
<211> LENGTH: 136
<212> TYPE: PRT
<213> ORGANISM: Papilio xuthus

<400> SEQUENCE: 64

Arg Tyr Ala Tyr Tyr Val Cys His Lys Cys Gly Lys Ala Tyr Phe Gly
1 5 10 15

Gly Leu Ala Arg Cys Glu Ala Glu Ser Asn Gly Arg Trp Glu Pro Ala

```
            20                  25                  30

Glu Leu Met Cys Gly Ala Cys Ser Asp Thr Thr Gly Ala Arg Ile Cys
        35                  40                  45

Pro Lys His Gly Ser Asp Phe Leu Glu Tyr Lys Cys Arg Tyr Cys Cys
    50                  55                  60

Ser Val Ala Val Phe Phe Cys Phe Gly Thr Ser His Phe Cys Asn Ala
65                  70                  75                  80

Cys His Asp Asp Phe Gln Arg Val Thr Asn Ile Pro Arg His Leu Leu
                85                  90                  95

Pro Gln Cys Pro Ala Gly Pro Arg Gly Glu Gln Met Pro Gly Asp Glu
            100                 105                 110

Cys Pro Leu His Val Gln His Pro Pro Thr Gly Glu Glu Phe Ala Leu
        115                 120                 125

Gly Cys Gly Ile Cys Arg His Ser
    130                 135


<210> SEQ ID NO 65
<211> LENGTH: 126
<212> TYPE: PRT
<213> ORGANISM: Oxytricha trifallax

<400> SEQUENCE: 65

Lys Leu Ala Ile Tyr Glu Cys Tyr Lys Cys Gln Arg Ile Tyr Cys Gly
1               5                   10                  15

Gly Arg Arg Asn Cys Glu Ala Glu Met Asn Glu Ala Asn Gln Pro Lys
            20                  25                  30

Lys Glu Asp Ile Leu Cys Val Tyr Cys Thr Ala Val Lys Ser Gly Asn
        35                  40                  45

Lys Phe Ala Pro Cys Lys Thr His Gly Glu Asp Tyr Met Gly His Lys
    50                  55                  60

Cys Gln Phe Cys Cys Glu Thr Ala Ser Trp Phe Cys Trp Gly Ala Thr
65                  70                  75                  80

Arg Phe Cys Asp Pro Cys His Asn Val Ala Ala Gln Asn Leu Pro Lys
                85                  90                  95

Ile Cys Asn Pro Glu Thr Cys Gln Leu Lys Gly Asn His Pro Pro Asn
            100                 105                 110

Gly Thr Pro Phe Ser Phe Gly Cys Lys Leu Cys Lys Ile Phe
        115                 120                 125


<210> SEQ ID NO 66
<211> LENGTH: 126
<212> TYPE: PRT
<213> ORGANISM: Oxytricha trifallax

<400> SEQUENCE: 66

Lys Leu Ala Phe Tyr Glu Cys Tyr Lys Cys Gln Lys Ile Tyr Cys Gly
1               5                   10                  15

Gly Arg Arg Asp Cys Glu Ala Glu Leu Asn Glu Ala Asn Gln Thr Lys
            20                  25                  30

Arg Glu Asp Leu Leu Cys Val Tyr Cys Thr Ala Leu Lys Leu Gly Asn
        35                  40                  45

Gln Phe Gln Pro Cys Asn Asn His Gly Glu Glu Phe Ile Glu Tyr Lys
    50                  55                  60

Cys Gln Phe Cys Cys Asp Ile Ala Ser Trp Phe Cys Trp Gly Ala Thr
65                  70                  75                  80

Arg Phe Cys Asp Pro Cys His Asn Ile Ala Thr Phe Asn Ile Pro Lys
```

```
                85                  90                  95

Ile Cys Asn Pro Asn Ser Cys Lys Phe Asn Gly Asn His Pro Pro Asn
            100                 105                 110

Gly Gln Pro His Ser Phe Gly Cys Lys Leu Cys Lys Ile Ser
        115                 120                 125


<210> SEQ ID NO 67
<211> LENGTH: 126
<212> TYPE: PRT
<213> ORGANISM: Oxytricha trifallax

<400> SEQUENCE: 67

Lys Leu Ala Ile Tyr Glu Cys Tyr Gln Cys Gln Thr Ile Tyr Cys Gly
1               5                   10                  15

Gly Arg Arg Asp Cys Glu Ala Glu Met Asn Glu Gly Asn Leu Pro Lys
            20                  25                  30

Lys Glu Asp Ile Leu Cys Val Tyr Cys Lys Ala Thr Lys Phe Gly Asn
        35                  40                  45

Gln Phe Ala Pro Cys Glu Thr His Gly Glu Asp Tyr Met Gly His Lys
    50                  55                  60

Cys Gln Phe Cys Cys Glu Thr Ala Arg Trp Phe Cys Trp Gly Ala Thr
65                  70                  75                  80

Arg Phe Cys Asp Pro Cys His Asn Ile Ala Thr Gln Asn Ile Pro Lys
                85                  90                  95

Ile Cys Asn Pro Glu Thr Cys Gln Met Lys Gly Asp His Pro Pro Asn
            100                 105                 110

Gly Thr Pro His Ser Phe Gly Cys Lys Leu Cys Lys Ile Leu
        115                 120                 125


<210> SEQ ID NO 68
<211> LENGTH: 126
<212> TYPE: PRT
<213> ORGANISM: Oxytricha trifallax

<400> SEQUENCE: 68

Lys Leu Ala Ile Tyr Glu Cys Tyr Asp Cys Gln Thr Ile Tyr Cys Gly
1               5                   10                  15

Gly Arg Arg Asp Cys Glu Ala Glu Met Asn Glu Ala Asn Leu Pro Lys
            20                  25                  30

Lys Glu Asp Ile Leu Cys Val Tyr Cys Lys Ala Lys Lys His Gly Asn
        35                  40                  45

Gln Phe Ala Pro Cys Glu Thr His Gly Glu Asp Tyr Met Gly His Lys
    50                  55                  60

Cys Gln Phe Cys Cys Glu Thr Ala Ile Phe Phe Cys Trp Gly Thr Val
65                  70                  75                  80

Arg Phe Cys Asp Pro Cys His Ser Ile Ala Thr Gln Asn Val Pro Lys
                85                  90                  95

Ile Cys Asn Pro Gln Thr Cys Gln Met Lys Gly Asn His Pro Pro Asn
            100                 105                 110

Gly Thr Pro His Ser Phe Gly Cys Lys Leu Cys Ile Ile Leu
        115                 120                 125


<210> SEQ ID NO 69
<211> LENGTH: 126
<212> TYPE: PRT
<213> ORGANISM: Oxytricha trifallax

<400> SEQUENCE: 69
```

-continued

```
Lys Leu Ala Met Tyr Asp Cys Phe Lys Cys Phe Lys Ile Phe Cys Gly
1               5                   10                  15

Gly Arg Arg Asp Cys Glu Ala Glu Leu Asn Val Glu Asn Gln Pro Lys
            20                  25                  30

Lys Glu Asp Ile Leu Cys Val Tyr Cys Gln Ser Gln Lys Gln Gly Val
        35                  40                  45

Arg Leu Ile Pro Cys Lys Asp His Gly Glu Leu Tyr Ile Glu His Lys
    50                  55                  60

Cys Gln Phe Cys Cys Asp Thr Ala Thr Phe Phe Cys Trp Gly Ala Thr
65                  70                  75                  80

Arg Phe Cys Asp Pro Cys His Gln Ile Gly Thr Asn Cys Ile Pro Lys
                85                  90                  95

Ile Cys Asn Pro Glu Thr Cys Gln Phe Lys Gly Lys His Pro Pro Asn
            100                 105                 110

Gly Lys Pro Tyr Ser Phe Gly Cys Lys Met Cys Arg Ile Asn
        115                 120                 125
```

<210> SEQ ID NO 70
<211> LENGTH: 126
<212> TYPE: PRT
<213> ORGANISM: Oxytricha trifallax

<400> SEQUENCE: 70

```
Lys Leu Ala Met Tyr Lys Cys Phe Gln Cys Glu Arg Leu Tyr Cys Gly
1               5                   10                  15

Gly Arg Arg Asp Cys Glu Ala Glu Leu Asn Glu Ala Asn Gln Pro Lys
            20                  25                  30

Lys Glu Asp Leu Leu Cys Val Tyr Cys Tyr Asn Ala Lys Tyr Gly Asn
        35                  40                  45

Asn Phe Ile Lys Cys Asp Lys His Asp Ile Glu Tyr Leu Glu His Lys
    50                  55                  60

Cys Gln Tyr Cys Cys Ser Leu Ala Ile Trp Phe Cys Phe Gly Thr Thr
65                  70                  75                  80

Arg Phe Cys Asn Pro Cys His Asp Ile Ala Ser Leu Asn Ile Pro Lys
                85                  90                  95

Ile Cys Asn Pro Glu Ile Cys Gln Trp Lys Gly Asp His Pro Pro Asn
            100                 105                 110

Gly Gln Pro His Cys Phe Gly Cys Lys Leu Cys Gln Asn Asp
        115                 120                 125
```

<210> SEQ ID NO 71
<211> LENGTH: 126
<212> TYPE: PRT
<213> ORGANISM: Oxytricha trifallax

<400> SEQUENCE: 71

```
Lys Leu Ala Met Tyr Lys Cys Phe Gln Cys Lys Thr Val Tyr Cys Gly
1               5                   10                  15

Gly Arg Arg Asp Cys Glu Ala Glu Leu Asn Glu Ala Asn Gln Pro Lys
            20                  25                  30

Asn Glu Asp Ile Leu Cys Val Tyr Cys Tyr Ser Gln Lys Tyr Gly Asn
        35                  40                  45

Arg Phe Ala Lys Cys Asp Thr His Asp Glu Glu Tyr Leu Glu His Lys
    50                  55                  60

Cys Gln Tyr Cys Cys Ser Val Ala Val Trp Phe Cys Phe Gly Ala Thr
65                  70                  75                  80
```

Arg Phe Cys Asn Asp Cys His Asn Ile Ala Thr Leu Asn Val Pro Lys
85 90 95

Ile Cys Asn Pro Glu Thr Cys Gln Trp Lys Gly Asp His Pro Pro Asn
100 105 110

Gly Gln Pro His Cys Phe Gly Cys Lys Leu Cys Gln Val Glu
115 120 125

<210> SEQ ID NO 72
<211> LENGTH: 123
<212> TYPE: PRT
<213> ORGANISM: Oxytricha trifallax

<400> SEQUENCE: 72

Lys Leu Ala Met Tyr Lys Cys Phe Gln Cys Thr Ser Leu Tyr Cys Gly
1 5 10 15

Gly Arg Arg Asp Cys Glu Ala Glu Leu Asn Glu Ala Asn Gln Pro Lys
20 25 30

Lys Glu Asp Leu Leu Cys Phe Tyr Cys Tyr Gly Ala Lys Tyr Gly Asn
35 40 45

Asn Ile Lys Lys Cys Lys Thr His Asp Pro Glu Tyr Leu Glu His Lys
50 55 60

Cys Gln Tyr Cys Cys Ser Val Ala Ser Trp Phe Cys Phe Gly Thr Thr
65 70 75 80

Arg Phe Cys Asp Pro Cys His Asp Ile Ala Thr Leu Asn Val Pro Lys
85 90 95

Ile Cys Asn Pro Glu Thr Cys Gln Trp Lys Gly Asp His Pro Pro Asn
100 105 110

Gly Gln Pro His Ala Phe Gly Cys Lys Leu Cys
115 120

<210> SEQ ID NO 73
<211> LENGTH: 128
<212> TYPE: PRT
<213> ORGANISM: Oxytricha trifallax

<400> SEQUENCE: 73

Lys Leu Ala Met Tyr Arg Cys Phe Asn Cys Ser Thr Ile Tyr Cys Gly
1 5 10 15

Gly Arg Arg Asp Cys Glu Ala Glu Met Asp Glu Ala Asn Arg Pro Pro
20 25 30

Pro Glu Asn Ile Leu Cys Ile Tyr Cys Asn Ala Val Lys His Gly Asp
35 40 45

Thr Leu Lys Pro Cys Glu Thr His Gly Thr Glu Tyr Ile Asp Tyr Lys
50 55 60

Cys Gln Phe Cys Cys Ser Pro Ala Thr Phe Phe Cys Phe Gly Ala Thr
65 70 75 80

Arg Phe Cys Asn Pro Cys His Asn Ile Ala Cys Ser Ala Val Ala Lys
85 90 95

Pro Cys Leu Gly Lys Glu Gly Gly Cys Glu Phe Asn Gly Asp His Leu
100 105 110

Pro Asn Gly Thr Pro Tyr His Ala Gly Cys Lys Met Cys Lys Val Leu
115 120 125

<210> SEQ ID NO 74
<211> LENGTH: 128
<212> TYPE: PRT
<213> ORGANISM: Oxytricha trifallax

<400> SEQUENCE: 74

Lys Leu Ala Met Tyr Arg Cys Phe Gln Cys Gln Thr Ile Tyr Cys Gly
1 5 10 15

Gly Arg Arg Asp Cys Glu Ala Glu Met Asn Glu Ala Asn Arg Pro Pro
20 25 30

Pro Glu Asp Ile Leu Cys Ile Tyr Cys Asn Ala Tyr Lys His Gly Asp
35 40 45

Lys Leu Lys Pro Cys Glu Thr His Gly Thr Glu Tyr Ile Asp Tyr Lys
50 55 60

Cys Gln Phe Cys Cys Thr Pro Ala Thr Phe Phe Cys Phe Gly Ala Thr
65 70 75 80

Arg Tyr Cys Asp Pro Cys His Asn Asn Ala Cys Gln Val Phe Gly Lys
85 90 95

Pro Cys Leu Gly Lys Glu Gly Gly Cys Ala Phe Asn Gly Asp His Leu
100 105 110

Pro Asn Gly Thr Pro Tyr His Ala Gly Cys Lys Met Cys Lys Val Leu
115 120 125

<210> SEQ ID NO 75
<211> LENGTH: 128
<212> TYPE: PRT
<213> ORGANISM: Oxytricha trifallax

<400> SEQUENCE: 75

Lys Leu Ala Met Tyr Lys Cys Phe Asn Cys Ser Lys Ile Tyr Cys Gly
1 5 10 15

Gly Arg Arg Asp Cys Glu Ala Glu Ile Asn Glu Ala Asn Leu Pro Leu
20 25 30

Pro Glu Asn Ile Leu Cys Ile Tyr Cys Asn Ala Thr Lys His Gly Asp
35 40 45

Thr Leu Lys Pro Cys Glu Thr His Gly Thr Glu Tyr Ile Asp Phe Lys
50 55 60

Cys Gln Phe Cys Cys Thr Pro Ala Lys Phe Phe Cys Phe Gly Ala Thr
65 70 75 80

Arg Tyr Cys Glu Pro Cys His Ser Asn Ala Cys Glu Ala Leu Ala Lys
85 90 95

Pro Cys Leu Gly Lys Glu Gly Gly Cys Ala Phe Asn Gly Asp His Leu
100 105 110

Pro Asn Gly Thr Pro Tyr His Ala Gly Cys Lys Met Cys Lys Val Leu
115 120 125

<210> SEQ ID NO 76
<211> LENGTH: 128
<212> TYPE: PRT
<213> ORGANISM: Oxytricha trifallax

<400> SEQUENCE: 76

Lys Leu Ala Met Tyr Lys Cys His Arg Cys Ser Thr Thr Phe Cys Gly
1 5 10 15

Gly Arg Arg Asp Cys Glu Ala Glu Met Asn Asp Glu Asn Gln Pro Lys
20 25 30

Pro Glu Asp Ile Met Cys Val Tyr Cys Ala Gly Leu Ala Gln Gly Asp
35 40 45

Lys Ile Lys Val Cys Asp Thr His Gly Gln Glu Tyr Met Asn His Lys
50 55 60

-continued

```
Cys Gln Phe Cys Cys Thr Pro Ala Arg Trp Phe Cys Phe Gly Ala Val
65                  70                  75                  80

Arg Tyr Cys Glu Pro Cys His Asn Ile Ala Thr Thr Val Ile Ala Lys
                85                  90                  95

Lys Cys Pro Gly Lys Glu Gly Gly Cys Pro Tyr Asp Gly Asp His Leu
            100                 105                 110

Pro Asn Gly Lys Pro Tyr Ser Ala Gly Cys Lys Met Cys Lys Ile Leu
        115                 120                 125


<210> SEQ ID NO 77
<211> LENGTH: 128
<212> TYPE: PRT
<213> ORGANISM: Oxytricha trifallax

<400> SEQUENCE: 77

Lys Leu Ala Met Tyr Glu Cys Phe Gln Cys Lys Ser Ile Tyr Cys Gly
1               5                   10                  15

Gly Arg Arg Asp Cys Glu Leu Asp Met Ser Ile Asp Asn Phe Leu Pro
            20                  25                  30

Gln Glu Asn Ile Leu Cys Leu Phe Cys Thr Ala Glu Asn Tyr Ser Asp
        35                  40                  45

Gln Leu Lys Pro Cys Glu Thr His Gly Thr Glu Tyr Leu Asp Tyr Lys
    50                  55                  60

Cys Gln Phe Cys Cys Thr Pro Ala Lys Phe Tyr Cys Phe Asn Ala Thr
65                  70                  75                  80

Ser Tyr Cys Glu Glu Cys His Thr Val Ala Cys Ser Ala Ile Pro Lys
                85                  90                  95

Leu Cys Lys Gly Asn Ile Gln Gly Cys Ser Tyr Lys Gly Asn His Pro
            100                 105                 110

Pro Asn Gly Thr Pro Tyr His Ala Gly Cys Lys Met Cys Lys Ile Gln
        115                 120                 125


<210> SEQ ID NO 78
<211> LENGTH: 126
<212> TYPE: PRT
<213> ORGANISM: Oxytricha trifallax

<400> SEQUENCE: 78

Lys Met Ala Ile Tyr Gln Cys Asn Asp Cys Gly Gly Cys Phe Tyr Gly
1               5                   10                  15

Gly Arg Arg Asp Cys Glu Ala Glu Leu Asp Glu Ala Lys Gln Pro Lys
            20                  25                  30

Pro Glu Asp Leu Leu Cys Ile Val Cys Thr Ser Tyr Arg Tyr Lys Ile
        35                  40                  45

Leu Asp Asp Asn Cys Val His His Gly Val Glu Tyr Ile Glu Tyr Lys
    50                  55                  60

Cys Gln Phe Cys Cys Glu Thr Ala Val Trp Tyr Cys Trp Gly Gly Thr
65                  70                  75                  80

Arg Met Cys Glu Thr Cys His Asp Ile Ala Gly Glu Asn Ile Pro Lys
                85                  90                  95

Val Cys Asn Glu Asp Ile Cys Pro Tyr Lys Gly Gln His Pro Gln Asn
            100                 105                 110

Gly Lys His His Ser Phe Gly Cys Asn Leu Cys Lys Ile Leu
        115                 120                 125


<210> SEQ ID NO 79
<211> LENGTH: 126
```

<212> TYPE: PRT
<213> ORGANISM: Oxytricha trifallax

<400> SEQUENCE: 79

Lys Leu Ala Ile Tyr Lys Cys His Asp Cys Gln Ile Phe Tyr Cys Gly
1 5 10 15

Gly Arg Arg Asp Cys Glu Ala Glu Leu Asp Glu Ala Lys Gln Pro Lys
20 25 30

Pro Gln Asp Leu Leu Cys Val Val Cys Thr Ser Phe Arg Tyr Glu Ile
35 40 45

Gln Asn Asp Asn Cys Val His His Gly Asp Glu Tyr Ile Glu Tyr Lys
50 55 60

Cys Gln Phe Cys Cys Glu Thr Ala Val Trp Tyr Cys Trp Gly Gly Thr
65 70 75 80

Arg Met Cys Glu Pro Cys His Asn Ile Ala Gly Glu Asn Ile Pro Lys
85 90 95

Ile Cys Asn Glu Asn Thr Cys Pro Tyr Lys Gly Gln His Pro Glu Asn
100 105 110

Gly Lys His His Ser Phe Gly Cys Asn Leu Cys Lys Ile Leu
115 120 125

<210> SEQ ID NO 80
<211> LENGTH: 129
<212> TYPE: PRT
<213> ORGANISM: Stylonychia lemnae

<400> SEQUENCE: 80

Lys Leu Ala Phe Tyr Gln Cys Phe Asp Cys Lys Lys Pro Tyr Phe Gly
1 5 10 15

Gly Lys Arg Asp Cys Glu Gln Glu Ala Leu Gln Glu Asn Ile Pro Asn
20 25 30

Lys Glu Asp Tyr Lys Cys Gly Arg Cys Lys Ala Leu Thr Phe Lys Ser
35 40 45

Gly Ile Thr Asn Cys Asp Val His Gly Glu Asp Phe Ile Glu Tyr Lys
50 55 60

Cys Gln Tyr Cys Cys His Val Ala Leu Trp Phe Cys Trp Gly Thr His
65 70 75 80

Arg Phe Cys Glu Pro Cys His Asp Asp Ala Ala Asn Gly His Asn Glu
85 90 95

Val Val Pro Cys Lys Gly Ser Lys Glu Cys Pro Leu Asn Gly His His
100 105 110

Asn Thr Asn Gly Gln Glu Tyr Ala Ile Gly Cys Arg Leu Cys Arg Asn
115 120 125

Asp

<210> SEQ ID NO 81
<211> LENGTH: 127
<212> TYPE: PRT
<213> ORGANISM: Stylonychia lemnae

<400> SEQUENCE: 81

Lys Leu Ala Phe Tyr Glu Cys Phe Lys Cys Lys Leu Pro Tyr Phe Gly
1 5 10 15

Gly Met Arg Asp Cys Ile Gln Glu Ala Gln Gln Asp Thr Gln His Asn
20 25 30

Lys Glu Asp Tyr Met Cys Gly Lys Cys Lys Ala Leu Thr His Gln Tyr
35 40 45

```
Gly Leu Thr Asn Cys Asp Thr His Gly Glu Asp Tyr Ile Glu Tyr Lys
    50                  55                  60

Cys Gln Tyr Cys Cys Glu Leu Ala Thr Trp Tyr Cys Glu Gly Leu Ala
65                  70                  75                  80

Arg Phe Cys Asn Pro Cys His Asp His Ala Cys Asp Asn Glu Ile Phe
                85                  90                  95

Pro Cys Lys Gly Pro Lys Glu Cys Pro Leu Asn Gly Asn His Glu Pro
            100                 105                 110

Asn Gly Asn Glu Tyr Ala Ile Gly Cys Arg Leu Cys Arg Ile Glu
        115                 120                 125


<210> SEQ ID NO 82
<211> LENGTH: 127
<212> TYPE: PRT
<213> ORGANISM: Stylonychia lemnae

<400> SEQUENCE: 82

Arg Tyr Gln Phe Phe Glu Cys Phe Gln Cys Lys Asp Pro Phe Phe Gly
1               5                   10                  15

Gly Val Arg Asp Cys Ala Ile Gln Ala Asn Gln Leu Gln Ala Pro Asn
            20                  25                  30

Pro Glu Glu Ile Leu Cys Asn Phe Cys Thr Ala Val Lys Leu Gly Ser
        35                  40                  45

Gly Lys Lys Ile Cys Glu Thr His Gly Val Glu Phe Ile Glu Phe Lys
    50                  55                  60

Cys Lys Tyr Cys Cys Asp Met Ser Gln Trp Phe Cys Phe Gly Thr Thr
65                  70                  75                  80

His Phe Cys His Lys Cys His Asp Met Ala Gly Ser Asn Val Thr Lys
                85                  90                  95

Asp Cys Pro Gly Asp Glu Lys Cys Pro Leu Lys Gly Lys His Pro Pro
            100                 105                 110

Asn Gly Gln Glu His Ala Leu Gly Cys Ala Val Cys Arg Gln Leu
        115                 120                 125


<210> SEQ ID NO 83
<211> LENGTH: 127
<212> TYPE: PRT
<213> ORGANISM: Stylonychia lemnae

<400> SEQUENCE: 83

Arg Tyr Gln Phe Phe Glu Cys Tyr Gln Cys Lys Asp Pro Phe Phe Gly
1               5                   10                  15

Gly Val Arg Asp Cys Ala Val Gln Ala Asn Gln Leu Gln Ala Pro Asn
            20                  25                  30

Pro Glu Asp Ile Met Cys Asn Phe Cys Thr Ala Met Lys Phe Gly Phe
        35                  40                  45

Gly Lys Asn Ile Cys Asp Thr His Gly Val Glu Phe Ile Glu Phe Lys
    50                  55                  60

Cys Lys Tyr Cys Cys Asp Leu Ser Ser Trp Phe Cys Phe Gly Thr Thr
65                  70                  75                  80

His Phe Cys Asn Gln Cys His Glu Arg Ala Gly Asn Asn Val Val Lys
                85                  90                  95

Asp Cys Ile Gly Asp Gln Lys Cys Pro Leu Lys Gly Lys His Pro Ala
            100                 105                 110

Asn Gly Gln Glu Tyr Ala Leu Gly Cys Ala Ile Cys Arg Gln Val
        115                 120                 125
```

<210> SEQ ID NO 84
<211> LENGTH: 125
<212> TYPE: PRT
<213> ORGANISM: Ichthyophthirius multifiliis

<400> SEQUENCE: 84

```
Ile Tyr Ser Tyr Tyr Met Cys Phe Lys Cys Lys Asn Pro Tyr Phe Gly
1               5                   10                  15

Gly Leu Lys Asp Cys Glu Arg Gln Leu Asn Glu Asn Gln Lys Glu Tyr
            20                  25                  30

Asn Pro Lys Asp Leu Val Cys Pro Asn Cys Cys Asp Ile Pro Val Lys
        35                  40                  45

Asn Cys Leu Lys His Gly Gln Asp Phe Leu Glu Phe Lys Cys Arg Tyr
    50                  55                  60

Cys Cys Ser Ile Ala Val Trp Phe Cys Phe Gly Thr Thr His Phe Cys
65                  70                  75                  80

Asp Pro Cys His Ile Lys Ala Gly Ile Ile Gln Asn Gln Ile Pro Lys
                85                  90                  95

Cys Lys Gly Lys Asp Cys Pro Phe Lys Glu Lys His Asn Pro Asn Gly
            100                 105                 110

Gln Glu Thr Pro Leu Gly Cys Ser Leu Cys Arg Asn Tyr
        115                 120                 125
```

<210> SEQ ID NO 85
<211> LENGTH: 130
<212> TYPE: PRT
<213> ORGANISM: Tetrahymena thermophila

<400> SEQUENCE: 85

```
Ile Tyr Ser Tyr Tyr Met Cys Tyr Lys Cys Lys Ala Pro Tyr Phe Gly
1               5                   10                  15

Gly Leu Lys Asp Cys Glu Arg Ala Leu Asn Asp Asp Lys Lys Asp Phe
            20                  25                  30

Gln Pro Lys Asp Leu Ile Cys Pro Asn Cys Cys Glu Ile Pro Val Glu
        35                  40                  45

Lys Cys Lys Gln His Gly Thr Glu Phe Ile Glu Phe Lys Cys Arg Tyr
    50                  55                  60

Cys Cys Ser Ile Ala Val Trp Phe Cys Phe Gly Thr Thr His Phe Cys
65                  70                  75                  80

Glu Pro Cys His Asn Asn Val Ser Asn Leu Gln Arg Met Lys Pro Lys
                85                  90                  95

Asp Tyr Pro Ile Cys Lys Gly Lys Lys Gly Cys Pro Phe Gln Gly Glu
            100                 105                 110

His Asn Pro Asn Gly Gln Glu Thr Pro Leu Gly Cys Ser Ile Cys Arg
        115                 120                 125

Asn Ile
    130
```

<210> SEQ ID NO 86
<211> LENGTH: 132
<212> TYPE: PRT
<213> ORGANISM: Stentor coeruleus

<400> SEQUENCE: 86

```
Arg Tyr Ser Tyr Tyr Met Cys Phe Lys Cys Lys Lys Pro Tyr Phe Gly
1               5                   10                  15
```

```
Gly Lys Lys Asp Cys Glu Gln Asn Asn Asp Gln Ala Lys Phe Asn Pro
            20                  25                  30

Glu Glu Leu Val Cys Pro Ser Cys Ser Ala Ile Gly Met Glu Gly Ser
        35                  40                  45

Asp Cys Lys Val His Gly Lys Asp Phe Ile Glu Phe Lys Cys Lys Phe
    50                  55                  60

Cys Cys Ser Val Ser Ala Trp Phe Cys Trp Gly Thr Thr His Phe Cys
65                  70                  75                  80

Asp Gln Cys His Thr Arg Gln Asn Asn Gly Asp Tyr Leu Ser Lys Lys
                85                  90                  95

Ser Lys Ser Glu Leu Pro Val Cys Pro Gly Lys Thr Cys Pro Leu Lys
            100                 105                 110

Ile Thr His Pro Pro Asn Gly Glu Glu Phe Pro Leu Gly Cys Thr Leu
        115                 120                 125

Cys Arg Asn Met
    130


<210> SEQ ID NO 87
<211> LENGTH: 133
<212> TYPE: PRT
<213> ORGANISM: Stentor coeruleus

<400> SEQUENCE: 87

Arg Tyr Ser Tyr Tyr Met Cys Phe Lys Cys Lys Lys Pro Tyr Phe Gly
1               5                   10                  15

Gly Lys Lys Asp Cys Glu Gln Asn Asn Asp Gln Ala Lys Phe Asp Ala
            20                  25                  30

Lys Glu Leu Val Cys Pro Ala Cys Ser Ala Val Gly Met Glu Gly Ala
        35                  40                  45

Asp Cys Lys Val His Gly Lys Asp Phe Ile Glu Phe Lys Cys Lys Phe
    50                  55                  60

Cys Cys Asn Ile Ser Ala Trp Phe Cys Trp Gly Thr Thr His Phe Cys
65                  70                  75                  80

Asp Thr Cys His Thr Lys Gln Asn Asn Gly Asp Tyr Ile Ser Lys Lys
                85                  90                  95

Pro Arg Ser Glu Leu Pro Ala Cys Pro Gly Lys Asp Thr Cys Pro Leu
            100                 105                 110

Lys Ile Arg His Pro Ala Asn Gly Glu Glu Phe Ala Leu Gly Cys Thr
        115                 120                 125

Leu Cys Arg Asn Met
    130


<210> SEQ ID NO 88
<211> LENGTH: 133
<212> TYPE: PRT
<213> ORGANISM: Pseudocohnilembus persalinus

<400> SEQUENCE: 88

Ile Tyr Ala Tyr Tyr Glu Cys Tyr Lys Cys Lys Lys Ser Tyr Phe Gly
1               5                   10                  15

Gly His Lys Asp Cys Gln Gln Ala Ile Asp Asp Gly Gln Arg Asp Phe
            20                  25                  30

Asn Pro Lys Asp Leu Val Cys Ala Asn Cys Cys Asp Ile Pro Ile Glu
        35                  40                  45

Asn Cys Lys Lys His Gly Lys Asp Phe Ile Glu Phe Lys Cys Lys Phe
    50                  55                  60
```

```
Cys Cys Ser Val Ser Gln Trp Phe Cys Trp Gly Thr Thr His Phe Cys
65                  70                  75                  80

Asp Ser Cys His Lys Lys Gln Cys Ser Gly Asp Tyr Val Ser Lys Tyr
                85                  90                  95

Thr Lys Glu Gln Leu Pro Lys Cys Pro Gly Lys Gln Lys Cys Pro Leu
            100                 105                 110

Lys Met Asp His Lys Pro Asn Gly Glu Glu Cys Ser Leu Gly Cys Met
        115                 120                 125

Met Cys Arg Asn Ala
    130


<210> SEQ ID NO 89
<211> LENGTH: 133
<212> TYPE: PRT
<213> ORGANISM: Tetrahymena thermophila

<400> SEQUENCE: 89

Ile Tyr Ala Tyr Phe Met Cys Phe Lys Cys Lys Lys Pro Tyr Phe Gly
1               5                   10                  15

Gly Leu Lys Asp Cys Gln Arg Gly Met Asp Glu Asp Lys Arg Glu Phe
            20                  25                  30

Asp Pro Lys Glu Leu Ile Cys Ala Asn Cys Cys Glu Ile Pro Val Glu
        35                  40                  45

Asn Cys Pro Lys His Gly Lys Asp Tyr Ile Glu Phe Lys Cys Lys Phe
    50                  55                  60

Cys Cys Ser Val Ala Gln Trp Phe Cys Trp Gly Thr Thr His Phe Cys
65                  70                  75                  80

Glu Pro Cys His Lys Arg Gln Cys Asn Gly Asp Tyr Val Ser Lys Tyr
                85                  90                  95

Pro Lys Glu Lys Leu Pro Lys Cys Ala Gly Gly Ser Lys Cys Pro Val
            100                 105                 110

Gly Gly Ser His Lys Pro Asn Gly Glu Glu Ser Ala Leu Gly Cys Ser
        115                 120                 125

Leu Cys Arg Asn Ala
    130


<210> SEQ ID NO 90
<211> LENGTH: 133
<212> TYPE: PRT
<213> ORGANISM: Ichthyophthirius multifiliis

<400> SEQUENCE: 90

Ile Tyr Ala Tyr Phe Met Cys Phe Lys Cys Lys Lys Pro Tyr Phe Gly
1               5                   10                  15

Gly Leu Lys Asp Cys Gln Arg Gly Met Asp Glu Asp Lys Arg Glu Phe
            20                  25                  30

Asn Pro Lys Glu Leu Val Cys Ala Asn Cys Cys Glu Ile Pro Ile Glu
        35                  40                  45

Asn Cys Thr Lys His Gly Lys Asp Tyr Ile Glu Phe Lys Cys Lys Phe
    50                  55                  60

Cys Cys Ser Thr Ala Gln Trp Phe Cys Trp Gly Thr Thr His Phe Cys
65                  70                  75                  80

Glu Thr Cys His Lys Arg Gln Cys Ser Gly Asp Tyr Val Ser Lys Tyr
                85                  90                  95

Thr Lys Asp Lys Leu Pro Lys Cys Gln Gly Pro Gly Lys Cys Ser Leu
            100                 105                 110
```

```
Gly Gly Asn His Lys Glu Asn Gly Glu Glu Cys Ser Leu Gly Cys Ala
        115                 120                 125

Leu Cys Arg Asn Ile
    130


<210> SEQ ID NO 91
<211> LENGTH: 134
<212> TYPE: PRT
<213> ORGANISM: Paramecium tetraurelia

<400> SEQUENCE: 91

Ile Tyr Cys Tyr Tyr Gln Cys Phe Lys Cys Lys Thr Pro Tyr Phe Gly
1               5                   10                  15

Gly Ala Lys Asp Cys Gln Arg Ala Leu Glu Glu Gly Asp Lys Gln Tyr
            20                  25                  30

Lys Pro Glu Glu Leu Ile Cys Ala Asn Cys Cys Asp Val Pro Val Gly
        35                  40                  45

Glu Thr Cys Gln Ile His Gly Lys Glu Tyr Ile Glu Phe Lys Cys Lys
    50                  55                  60

Phe Cys Cys Gln Ile Ala Val Trp Phe Cys Trp Gly Thr Thr His Phe
65                  70                  75                  80

Cys Glu Asp Cys His Lys Arg Gln Cys Asn Gly Asp Tyr Val Ser Lys
                85                  90                  95

Ile Pro Lys Glu Lys Leu Pro Lys Cys Pro Gly Lys Asp Lys Cys Pro
            100                 105                 110

Ile Lys Met Glu His Lys Pro Asn Gly Glu Glu Gln Ala Leu Gly Cys
        115                 120                 125

Ala Ile Cys Arg Asn Gln
    130


<210> SEQ ID NO 92
<211> LENGTH: 138
<212> TYPE: PRT
<213> ORGANISM: Stylonychia lemnae

<400> SEQUENCE: 92

Lys Leu Ser Tyr Tyr Glu Cys Phe Lys Cys Lys Gln Pro Tyr Phe Gly
1               5                   10                  15

Gly Met Lys Asp Cys Glu Asn Asn Gln Glu Glu Asn Lys Gln Gln Glu
            20                  25                  30

Tyr Lys Lys Glu Asp Leu Val Cys Ala Ser Cys Ser Ala Val Ala Val
        35                  40                  45

Gly Gly Gly Val Gln Asn Cys Pro Lys His Gly Leu Asp Tyr Ile Glu
    50                  55                  60

Phe Lys Cys Lys Phe Cys Cys Asn Ile Ala Gln Trp Phe Cys Trp Gly
65                  70                  75                  80

Thr Thr His Phe Cys Glu Ser Cys His Thr Lys Gln Asn Asn Gly Asp
                85                  90                  95

Tyr Val Ser Arg Lys Lys Arg Ser Glu Leu Pro Arg Cys Ser Gly Pro
            100                 105                 110

Ala Lys Cys Pro Leu Lys Ile Gln His Pro Glu Asn Gly Glu Glu Phe
        115                 120                 125

Pro Leu Gly Cys Ala Leu Cys Arg Asn Leu
    130                 135


<210> SEQ ID NO 93
<211> LENGTH: 136
```

-continued

<212> TYPE: PRT
<213> ORGANISM: Stylonychia lemnae

<400> SEQUENCE: 93

```
Lys Leu Ala Tyr Tyr Gln Cys Phe Gln Cys Lys Ile Pro Tyr Phe Gly
1               5                   10                  15

Gly Met Lys Asp Cys Ile Gln Ala Gln Gln Glu Gly Gln Gln Tyr Lys
            20                  25                  30

Leu Glu Glu Leu Val Cys Gly Lys Cys Ser Ala Val Ser Ile Gly Ala
        35                  40                  45

Gly Ile Ala Asn Cys Gln Lys His Gly Thr Asp Tyr Ile Glu Phe Lys
    50                  55                  60

Cys Arg Phe Cys Cys Ser Leu Ala Gln Trp Phe Cys Trp Gly Thr Thr
65                  70                  75                  80

His Phe Cys Glu Pro Cys His Lys Arg Gln Val Asp Gly Asp Tyr Val
                85                  90                  95

Ser Lys Lys Thr Lys Ala Glu Leu Pro Gln Cys Gly Ser Ala Glu Lys
            100                 105                 110

Cys Pro Leu Lys Leu Lys His Pro Glu Asn Gly Asp Glu Phe Ala Met
        115                 120                 125

Gly Cys Ala Val Cys Arg Asn Glu
    130                 135
```

<210> SEQ ID NO 94
<211> LENGTH: 136
<212> TYPE: PRT
<213> ORGANISM: Oxytricha trifallax

<400> SEQUENCE: 94

```
Lys Leu Ala Tyr Tyr Gln Cys Phe Lys Cys Lys Thr Pro Tyr Phe Gly
1               5                   10                  15

Gly Leu Lys Asp Cys Ile Gln Ala Gln Gln Glu Gly Gln Gln Tyr Lys
            20                  25                  30

Ile Glu Glu Leu Val Cys Gly Lys Cys Ala Ala Val Ser Met Gly Ala
        35                  40                  45

Gly Ile Ala Asn Cys Gln Lys His Gly Thr Asp Tyr Ile Glu Phe Lys
    50                  55                  60

Cys Arg Phe Cys Cys Ser Ile Ala Gln Trp Phe Cys Trp Gly Ser Thr
65                  70                  75                  80

His Phe Cys Glu Pro Cys His Lys Lys Gln Val Glu Gly Asp Tyr Val
                85                  90                  95

Ser Lys Lys Ser Lys Ala Glu Leu Leu Gln Cys Lys Thr Lys Glu Asn
            100                 105                 110

Cys Pro Leu Lys Val Gln His Pro Glu Asn Gly Asp Glu Phe Ala Leu
        115                 120                 125

Gly Cys Ala Ile Cys Arg Asn Glu
    130                 135
```

<210> SEQ ID NO 95
<211> LENGTH: 120
<212> TYPE: PRT
<213> ORGANISM: Cavenderia fasciculata

<400> SEQUENCE: 95

```
Arg Leu Ser Phe Phe Pro Cys Phe Lys Cys Lys Lys Pro Tyr Phe Gly
1               5                   10                  15

Gly Glu Lys Ala Cys Gly Glu Asn Asn Val Asp Phe Lys Pro Glu Glu
```

```
            20                  25                  30

Leu Leu Cys Gly Gly Cys Ser Cys Asp Gly Ala Asp Asn Cys Lys Thr
        35                  40                  45

His Gly Lys Glu Tyr Ile Glu Tyr Lys Cys Lys Phe Cys Cys Asn Met
    50                  55                  60

Ser Val Phe Phe Cys Trp Gly Lys Thr His Phe Cys Asn Ser Cys His
65                  70                  75                  80

Ser Gln Ser Thr Thr Ile Val Lys Thr Pro Lys Asp Gln Leu Pro Lys
                85                  90                  95

Cys Ser Cys Gly Val Pro His Pro Pro Asn Gly Glu Glu His Ser Phe
            100                 105                 110

Gly Cys Ser Leu Cys Arg Ile Asn
        115                 120


<210> SEQ ID NO 96
<211> LENGTH: 120
<212> TYPE: PRT
<213> ORGANISM: Polysphondylium pallidum

<400> SEQUENCE: 96

Arg Leu Ser Tyr Phe Pro Cys Phe Lys Cys Lys Lys Pro Tyr Phe Gly
1               5                   10                  15

Gly Glu Lys Ala Cys Gly Glu Asn Asn Val Asp Phe Lys Ala Glu Glu
            20                  25                  30

Leu Leu Cys Gly Gly Cys Ser Cys Asp Gly Lys Asp Asn Cys Glu Lys
        35                  40                  45

His Gly Lys Asp Tyr Ile Glu Tyr Lys Cys Lys Phe Cys Cys Asn Thr
    50                  55                  60

Ser Val Phe Phe Cys Trp Gly Lys Thr His Phe Cys Asp Asp Cys His
65                  70                  75                  80

Lys Lys Ser Thr Glu Met Val Arg Thr Pro Arg Ala Asp Leu Pro Lys
                85                  90                  95

Cys Thr Cys Gly Asn Ile His Pro Leu Asn Gly Glu Glu His Cys Tyr
            100                 105                 110

Gly Cys Ser Ile Cys Arg Ile Asn
        115                 120


<210> SEQ ID NO 97
<211> LENGTH: 121
<212> TYPE: PRT
<213> ORGANISM: Dictyostelium purpureum

<400> SEQUENCE: 97

Arg Phe Ser Tyr Phe Met Cys Phe Lys Cys Lys Lys Pro Tyr Phe Gly
1               5                   10                  15

Gly Glu Lys Ala Cys Gly Asp Asn Arg Gln Asp Phe Lys Pro Glu Glu
            20                  25                  30

Leu Ile Cys Gly Gly Cys Ser Ala Asn Gly Asn Glu Ile Cys Lys Ile
        35                  40                  45

His Gly Lys Glu Phe Ile Glu Tyr Lys Cys Lys Tyr Cys Cys Asn Ile
    50                  55                  60

Ser Ile Phe Phe Cys Trp Gly Lys Thr His Phe Cys Ala Asp Cys His
65                  70                  75                  80

Lys Lys Val Asn Glu Val Thr Lys Thr Pro Lys His Leu Leu Pro Gln
                85                  90                  95

Cys Lys Cys Asp Val Glu Val Lys His Gln Val Gly Glu Glu Phe Cys
```

```
            100                 105                 110

Phe Gly Cys Thr Leu Cys Ile Ile Ser
        115                 120


<210> SEQ ID NO 98
<211> LENGTH: 119
<212> TYPE: PRT
<213> ORGANISM: Tieghemostelium lacteum

<400> SEQUENCE: 98

Arg Phe Ser Tyr Phe Gln Cys Phe Lys Cys Asn Lys Pro Tyr Phe Gly
1               5                   10                  15

Gly Glu Lys Ala Cys Gly Glu Asn Arg Leu Asp Phe Lys Ala Glu Glu
            20                  25                  30

Leu Ile Cys Gly Gly Cys Ser Ser Asp Gly Asn Asp His Cys Lys Ile
        35                  40                  45

His Gly Lys Glu Tyr Ile Glu Tyr Lys Cys Lys Trp Cys Cys Asn Val
    50                  55                  60

Ser Thr Phe Phe Cys Trp Gly Lys Thr His Met Cys Asp Ser Cys His
65                  70                  75                  80

Arg Arg Val Thr Glu Val Ala Arg Thr Pro Lys Ala Gln Leu Pro Arg
                85                  90                  95

Cys Lys Cys Asp Gln Lys His Glu Glu Gly Glu Glu Phe Cys Phe Gly
            100                 105                 110

Cys Ser Leu Cys Arg Ile Leu
        115


<210> SEQ ID NO 99
<211> LENGTH: 125
<212> TYPE: PRT
<213> ORGANISM: Dictyostelium discoideum

<400> SEQUENCE: 99

Arg Phe Ser Tyr Phe Met Cys Phe Lys Cys Lys Lys Pro Tyr Phe Gly
1               5                   10                  15

Gly Glu Lys Val Cys Ala Ile Ala Asp Glu Asn Arg Ile Ala Gly Glu
            20                  25                  30

His Lys Pro Glu Glu Leu Val Cys Gly Gly Cys Ser Ser Ser Gly Asn
        35                  40                  45

Glu Asn Cys Lys Ile His Gly Lys Glu Phe Ile Glu Tyr Lys Cys Lys
    50                  55                  60

Tyr Cys Cys Arg Ile Ser Ala Phe Phe Cys Trp Gly Asn Ser His Phe
65                  70                  75                  80

Cys Val Glu Cys His Arg Asn Val Asn His Val Ala Gln Ile Pro Lys
                85                  90                  95

Thr Gln Leu Pro Gln Cys Cys Glu Gly Ser Glu Lys His Ile Ser Gly
            100                 105                 110

Glu Glu Phe Cys Tyr Gly Cys Ser Met Cys Lys Ile Ile
        115                 120                 125


<210> SEQ ID NO 100
<211> LENGTH: 123
<212> TYPE: PRT
<213> ORGANISM: Spongospora subterranea

<400> SEQUENCE: 100

Arg Phe Ala Phe Tyr Leu Cys Phe Lys Cys Gln Lys Pro Tyr Phe Gly
1               5                   10                  15
```

```
Gly Arg Arg Gln Cys Gly Asn Leu Ala Gly Met Asp Glu Glu Lys Phe
            20                  25                  30

Asn Ala Ala Glu Leu Val Cys Gly Gly Cys Ser Gly Asn Ala Val Asn
        35                  40                  45

Cys Pro Thr His Gly Thr Asp Phe Ile Glu Tyr Lys Cys His Phe Cys
    50                  55                  60

Cys Lys Val Ala Val Trp Phe Cys Trp Gly Thr Thr His Phe Cys Asp
65                  70                  75                  80

Pro Cys His Arg Phe Ser Lys Gly Ala Arg Ile Val Lys Cys Pro Gly
                85                  90                  95

Pro Thr Val Cys Pro Leu Gly Ile Asp His Pro Pro Asn Gly Arg Glu
            100                 105                 110

Phe Ser Leu Gly Cys Ala Ile Cys Asn Arg Cys
        115                 120


<210> SEQ ID NO 101
<211> LENGTH: 129
<212> TYPE: PRT
<213> ORGANISM: Reticulomyxa filosa

<400> SEQUENCE: 101

Arg Tyr Ala Phe Tyr Cys Cys Phe Val Cys Lys Lys Pro Tyr Tyr Gly
1               5                   10                  15

Gly Leu Gly Arg Cys Ala Asp Gly Leu His Glu Met Asn Pro Ser Asp
            20                  25                  30

Phe Ile Cys Pro Ala Cys Ser Gly Ile Gly Leu Asp Ser Cys Ser Val
        35                  40                  45

His Gly Arg Asp Tyr Met Ile Tyr Lys Cys Arg Phe Cys Cys Ser Val
    50                  55                  60

Ala Ser Tyr Phe Cys Trp Gly Thr Thr His Phe Cys Pro Asp Cys His
65                  70                  75                  80

Lys Leu Ser Ala Leu Phe Gly Asp Tyr Arg Thr Lys Thr Lys Glu Asn
                85                  90                  95

Leu Pro Gln Cys Glu Gly Pro Asp Lys Cys Pro Leu Gly Leu Glu His
            100                 105                 110

Pro Ala Asn Gly Glu Glu Phe Ser Leu Gly Cys Ser Leu Cys Arg Gly
        115                 120                 125

Ala


<210> SEQ ID NO 102
<211> LENGTH: 130
<212> TYPE: PRT
<213> ORGANISM: Polysphondylium pallidum

<400> SEQUENCE: 102

His Tyr Ser Tyr Tyr Leu Cys Phe Lys Cys Lys Ile Pro Tyr Phe Ala
1               5                   10                  15

Gly Gln Val Arg Cys Asp Gln Gly Asn Glu Asn Asp Glu Phe Asn Ser
            20                  25                  30

Gln Asp Leu Ile Cys Pro Ser Cys Arg Gly Glu Cys Tyr Gln Lys Cys
        35                  40                  45

Asn Ile His Gly Trp Asp Phe Met Glu Phe Lys Cys His Phe Cys Cys
    50                  55                  60

Ser Ile Ala Ser Phe Phe Cys Trp Gly Lys Ile His Phe Cys Asp Thr
65                  70                  75                  80
```

-continued

```
Cys His Thr Lys Gln Gln Lys Gly Asp Tyr Leu Thr Lys Lys Pro Lys
                85                  90                  95

Ser Met Ile Pro Met Cys Pro Gly Ile Glu Ser Cys Pro Leu Lys Ile
            100                 105                 110

Ala His Pro His Cys Glu Glu Phe Ser Leu Gly Cys Ser Ile Cys Lys
        115                 120                 125

Met Ile
    130


<210> SEQ ID NO 103
<211> LENGTH: 129
<212> TYPE: PRT
<213> ORGANISM: Cavenderia fasciculata

<400> SEQUENCE: 103

Arg Tyr Gln Tyr Tyr Pro Cys Tyr Lys Cys Lys Ser Pro Tyr Phe Ala
1               5                   10                  15

Gly Met Val Arg Cys Asp Gln Gly Ile Asp Thr Tyr Lys Leu Asp Glu
            20                  25                  30

Leu Leu Cys Glu Asn Cys Arg Pro Thr Thr Thr Gly Ser Thr Cys Thr
        35                  40                  45

Val His Gly Val Glu Tyr Met Glu Phe Lys Cys His Tyr Cys Cys Ser
    50                  55                  60

Lys Ala Ser Trp Val Cys Trp Ser Lys Ile Arg Phe Cys Asp Asp Cys
65                  70                  75                  80

His Lys Lys Gln Gln Gly Gly Asp Tyr Leu Thr Lys Lys Pro Ile Glu
                85                  90                  95

Glu Ile Pro Lys Cys Pro Gly Lys Glu His Cys Pro Leu Lys Ile Asp
            100                 105                 110

His Pro His Leu Glu Glu Val Pro Leu Gly Cys Thr Ile Leu Phe Gly
        115                 120                 125

Lys


<210> SEQ ID NO 104
<211> LENGTH: 128
<212> TYPE: PRT
<213> ORGANISM: Dictyostelium purpureum

<400> SEQUENCE: 104

Arg Tyr Val Tyr Tyr Ser Cys Phe Lys Cys Lys Lys Phe Tyr Phe Ala
1               5                   10                  15

Gly Gln Ala Arg Cys Asp Glu Gly Gly Glu Gly Tyr Asn Glu Glu Asp
            20                  25                  30

Leu Ile Cys Gly Ser Cys Arg Gly Ser Asp Gly Lys Glu Cys Lys Ile
        35                  40                  45

His Gly Trp Asp Tyr Leu Ile Trp Lys Cys Gln Phe Cys Cys Ser Pro
    50                  55                  60

Ser Gln Trp Tyr Cys Trp Ser Lys Thr His Phe Cys Asn Glu Cys His
65                  70                  75                  80

Thr Lys Gln Gln Lys Gly Asp Tyr Leu Asn Lys Lys Pro Lys Thr Ala
                85                  90                  95

Phe Pro Val Cys Glu Gly Pro Glu Lys Cys Pro Leu Lys Val Ala His
            100                 105                 110

Pro His Val Ala Glu Phe Ile Leu Gly Cys Ser Leu Cys Asn Asn Leu
        115                 120                 125
```

<210> SEQ ID NO 105
<211> LENGTH: 129
<212> TYPE: PRT
<213> ORGANISM: Dictyostelium discoideum

<400> SEQUENCE: 105

Arg Tyr Val Tyr Tyr Ser Cys Phe Lys Cys Lys Gly Phe Tyr Phe Ala
1               5                   10                  15

Gly Gln Ala Arg Cys Asp Glu Gly Val Glu Gly Gly Tyr Lys Asp Glu
            20                  25                  30

Asp Leu Ile Cys Gly Ser Cys Arg Gly Ser Asp Gly Lys Glu Cys Lys
        35                  40                  45

Val His Gly Trp Asp Tyr Ile Ile Trp Lys Cys Gln Phe Cys Cys Ser
    50                  55                  60

Ile Ala Gln Trp Tyr Cys Trp Ser Lys Thr His Phe Cys Ser Gln Cys
65                  70                  75                  80

His Ala Ile Gln Asn Gly Gly Lys Tyr Leu Asn Lys Ile Pro Lys Thr
                85                  90                  95

Glu Ile Pro Arg Cys Glu Gly Pro Asp Lys Cys Pro Leu Lys Val Asp
            100                 105                 110

His Pro His Val Glu Glu Phe Ile Leu Gly Cys Thr Leu Cys Lys Asn
        115                 120                 125

Leu

<210> SEQ ID NO 106
<211> LENGTH: 129
<212> TYPE: PRT
<213> ORGANISM: Tieghemostelium lacteum

<400> SEQUENCE: 106

Arg Tyr Val Tyr Tyr Gln Cys Phe Lys Cys Ala Asn Pro Tyr Phe Ala
1               5                   10                  15

Gly Ala Ala Arg Cys Asp Glu Gly Ile Asp Gly Tyr Lys Glu Glu Glu
            20                  25                  30

Leu Leu Cys Asn Ser Cys Gln Gly Val Asp Lys Asn Gly Glu Cys Lys
        35                  40                  45

Leu His Gly Leu Asp Tyr Ile Thr Trp Lys Cys Lys Phe Cys Cys Asn
    50                  55                  60

Glu Ala Ser Phe Phe Cys Trp Asn Lys Thr His Phe Cys Ser Ser Cys
65                  70                  75                  80

His Thr Lys Gln Gln Gly Gly Asp Tyr Leu Asn Lys Lys Pro Ile Glu
                85                  90                  95

Gln Ile Pro Lys Cys Pro Gly Pro Asp Gln Cys Pro Leu Lys Ile Ser
            100                 105                 110

His Pro His Cys Glu Glu Tyr Val Leu Gly Cys Ser Leu Cys Lys Asn
        115                 120                 125

Leu

<210> SEQ ID NO 107
<211> LENGTH: 131
<212> TYPE: PRT
<213> ORGANISM: Selaginella moellendorffii

<400> SEQUENCE: 107

Gln Tyr Gln Tyr Tyr Met Cys Ser Lys Cys Lys Asn Pro Tyr Tyr Gly
1               5                   10                  15

Gly Lys Arg Asn Cys Gly Pro Asn Leu Ala Glu Asp Gln Gly Arg Gln

```
            20                  25                  30

Tyr Asp Pro Ser Glu Leu Val Cys Gly Gly Cys Ser Ala Gly Ala Asp
        35                  40                  45

Gly Lys Cys Lys Leu Gly His Gly Asn Gln Phe Val Glu Phe Lys Cys
    50                  55                  60

Arg Phe Cys Cys Ser Ile Ala Thr Phe Phe Cys Phe Gly Thr Ile His
65                  70                  75                  80

Phe Cys Asp Ser Cys His Gly Ile Trp Pro Gln Gln His Ser Ser Ser
                85                  90                  95

Tyr Val Leu Pro Gln Cys Lys Gly Pro Gln His Cys Pro Leu Gly Ile
            100                 105                 110

Ala His Ala Pro Asn Gly Lys Glu His Cys Leu Gly Cys Ser Met Cys
        115                 120                 125

Arg Ser Gln
    130


<210> SEQ ID NO 108
<211> LENGTH: 131
<212> TYPE: PRT
<213> ORGANISM: Micromonas commoda

<400> SEQUENCE: 108

Arg Phe Asn Tyr Tyr Lys Cys Gly Lys Cys Gly Glu Pro Tyr Phe Gly
1               5                   10                  15

Gly Leu Arg Glu Cys Gly Gly Glu Pro Gly Gly Gly Gly Gly Asp Ala
            20                  25                  30

Asn Gly Asp Ala Glu Leu Met Cys Gly Gly Cys Ser Ala Thr Val Ser
        35                  40                  45

Gly Leu Ser Gly Ala Cys Ala Lys His Gly Arg Asp Glu Leu Gln Phe
    50                  55                  60

Lys Cys Arg Phe Cys Cys Ser Pro Ala Val Phe Phe Cys Phe Gly Ser
65                  70                  75                  80

Thr His Phe Cys Glu Arg Cys His Val Thr Arg Pro Asp Trp Lys Pro
                85                  90                  95

Gln Pro Pro Pro Lys Thr Cys Thr Arg Ala Thr Cys Pro Leu Gly Val
            100                 105                 110

Asp His Pro Pro His Gly Gln Glu Phe Cys Leu Gly Cys Ala Leu Cys
        115                 120                 125

Arg Ala Thr
    130


<210> SEQ ID NO 109
<211> LENGTH: 136
<212> TYPE: PRT
<213> ORGANISM: Gonium pectorale

<400> SEQUENCE: 109

Arg Leu Leu Phe Tyr Lys Cys Ser Arg Cys Ser Lys Pro Tyr Tyr Gly
1               5                   10                  15

Gly Gln Arg Ala Cys Gly Val Ala Gly Ala Gly Ala Ala Gln Ala Ala
            20                  25                  30

Gly Gly Ala Ala Ala Gly Gln Ala Gln Asp Leu Val Cys Gly Glu Cys
        35                  40                  45

Cys Ala Leu Ala Thr Gly Asn Asn Cys Pro Arg His Gly Thr Thr Tyr
    50                  55                  60

Ile Glu Trp Lys Cys Arg Tyr Cys Cys Ser Leu Ala Ser Trp Phe Cys
```

```
65                  70                  75                  80

Phe Gly Thr Thr His Phe Cys Glu Pro Cys His Ala Val Ala Gly Thr
                85                  90                  95

Arg Met Ala Gly Pro Phe Asp Lys Gly Asp Thr Cys Arg Asp Pro Lys
            100                 105                 110

Cys Thr Leu Gly Ile Lys His Pro Pro Pro Gly Gln Glu Ala Cys Leu
        115                 120                 125

Gly Cys Gly Met Cys Arg Ala Gly
    130                 135


<210> SEQ ID NO 110
<211> LENGTH: 122
<212> TYPE: PRT
<213> ORGANISM: Aureococcus anophagefferens

<400> SEQUENCE: 110

Phe Tyr Glu Cys Gly Asp Cys Gly Arg Ala Phe Val Gly Gly Ala Arg
1               5                   10                  15

Ala Cys Gly Ala Met Ala Glu Gly Glu Gly Pro Gly Ala Thr Arg Arg
            20                  25                  30

Cys Gly Ala Cys Gln Val Val Gly Arg Gly Cys Ala Arg Gly His Gly
        35                  40                  45

Asp Ala Ala Ile Ala Trp Lys Cys Arg Tyr Cys Cys Ala Glu Ala Ser
    50                  55                  60

Phe Phe Cys Phe Gly Thr Thr Ser Phe Cys Ser Ser Cys His Gly Ala
65                  70                  75                  80

Ala Asn Arg Gly Ala Leu Asp Ala Asp Arg Ala Pro Cys Arg Gly Pro
                85                  90                  95

Arg His Cys Pro Leu Gly Val Lys His Pro Pro His Gly Val Glu Phe
            100                 105                 110

Ser Leu Gly Cys Ser Leu Cys Arg Ser Glu
        115                 120


<210> SEQ ID NO 111
<211> LENGTH: 121
<212> TYPE: PRT
<213> ORGANISM: Capsaspora owczarzaki

<400> SEQUENCE: 111

Ser Tyr Ser Tyr Tyr Lys Cys Phe Lys Cys Pro Ser Trp Tyr Tyr Gly
1               5                   10                  15

Gly Arg Val Glu Cys Gly Glu Asn Ala Asp Ala Pro Phe Asn Pro Glu
            20                  25                  30

Glu Leu Val Cys Ala Gly Cys Ser Thr Ala Gly Leu Ser Asn Cys Pro
        35                  40                  45

Thr His Gly Ala Glu Tyr Ile Gly Phe Lys Cys Lys Phe Cys Cys Glu
    50                  55                  60

Leu Ser Thr Phe Phe Cys Ala Gly Thr Thr His Phe Cys Glu Pro Cys
65                  70                  75                  80

His Arg Ala Gly Phe Gly Ala Pro Val Lys Pro Cys Arg Gly Ala Pro
                85                  90                  95

His Cys Leu Leu Gly Pro Asn His Ile Pro Asn Gly Gln Glu Tyr Ala
            100                 105                 110

Val Gly Cys Ala Leu Cys Ser Asn Leu
        115                 120
```

```
<210> SEQ ID NO 112
<211> LENGTH: 131
<212> TYPE: PRT
<213> ORGANISM: Ectocarpus siliculosus

<400> SEQUENCE: 112

Lys Tyr Ser Tyr Tyr Gln Cys His Ser Cys Arg Lys Pro Tyr Phe Gly
1               5                   10                  15

Gly Leu Val Ser Cys Glu Pro Ala Pro Pro Pro Ala Gly Gly Ala Glu
            20                  25                  30

Arg Ala Leu Ala Asp Ile Lys Pro Ser Glu Leu Leu Cys Gly Lys Cys
        35                  40                  45

Ser Ala Gly Ser Gly Gly Ala Ser Cys Ser Glu His Gly Gln Glu Phe
    50                  55                  60

Met Glu His Lys Cys Tyr Trp Cys Cys Lys Val Ala Ser Tyr Phe Cys
65                  70                  75                  80

Gly Gly Val Met His Phe Cys Asp Ala Cys His Leu His Gly Phe Ala
                85                  90                  95

Ala Lys Pro Lys Pro Cys Leu Gly Gly Ala His Cys Leu Phe Gly Gly
            100                 105                 110

Gln His Pro Asp Lys Ala Lys Glu Tyr Val Leu Gly Cys Gly Ile Cys
        115                 120                 125

Arg Pro Lys
    130


<210> SEQ ID NO 113
<211> LENGTH: 138
<212> TYPE: PRT
<213> ORGANISM: Acanthamoeba castellanii

<400> SEQUENCE: 113

Thr Phe Ala Phe Tyr Leu Cys Tyr Gln Cys Lys Ala Pro Tyr Phe Gly
1               5                   10                  15

Gly Lys Lys Glu Cys Gly Arg Met Leu Gly Asp Gly Gly Gly Glu Gly
            20                  25                  30

Gly Pro Ala Pro Ala Phe Asn Pro Lys Glu Leu Ile Cys Gly Ala Cys
        35                  40                  45

Ser Asn Thr Leu Gly Gln Ala Asp Cys Arg Val His Gly Asp Ala Tyr
    50                  55                  60

Met Glu Trp Lys Cys Arg Phe Cys Cys Ser Leu Ala Thr Tyr Phe Cys
65                  70                  75                  80

Gly Gly Lys Ala Arg Phe Cys Thr Pro Cys His Asp Arg Pro Ala Glu
                85                  90                  95

Arg Val Glu Phe Ala Thr Leu Asp Thr Phe Lys Ala Pro Ala Cys Gly
            100                 105                 110

Gly Ala Ala Ser Cys Pro Leu His Val Asp His Pro Pro Asn Gly Glu
        115                 120                 125

Glu Phe Cys Leu Gly Cys Ser Met Cys Lys
    130                 135


<210> SEQ ID NO 114
<211> LENGTH: 138
<212> TYPE: PRT
<213> ORGANISM: Acanthamoeba castellanii

<400> SEQUENCE: 114

Thr Phe Ala Phe Tyr Met Cys Tyr Arg Cys Arg Ser Pro Tyr Phe Gly
1               5                   10                  15
```

```
Gly Lys Lys Glu Cys Ala Asn Met Gly Gly Pro Pro Gly Ala Gly Ala
            20                  25                  30

Gln Gly Gly Ala Phe Asn Pro Lys Glu Leu Val Cys Gly Ala Cys Ser
        35                  40                  45

Asn Thr Ser Gly Gln Thr Cys Leu Ile His Gly Glu Glu Tyr Met Glu
    50                  55                  60

Trp Lys Cys Arg Phe Cys Cys Arg Leu Ala Thr Tyr Phe Cys Ala Gly
65                  70                  75                  80

Lys Ala Arg Phe Cys Asp Pro Cys His Gly Val Pro Ala Glu Arg Val
                85                  90                  95

Asp Phe Asn Pro Glu Tyr Leu Lys Ser Ala Pro Lys Cys Asn Gly Pro
            100                 105                 110

Ser Asp Cys Pro Leu Gly Val Tyr His Pro Pro Asn Gly Glu Glu Phe
        115                 120                 125

Cys Leu Gly Cys Val Leu Cys Arg Ala Ile
    130                 135


<210> SEQ ID NO 115
<211> LENGTH: 134
<212> TYPE: PRT
<213> ORGANISM: Oxytricha trifallax

<400> SEQUENCE: 115

Lys Leu Ser Phe Tyr Gln Cys Phe Gln Cys Lys His Pro Tyr Tyr Gly
1               5                   10                  15

Gly Met Asn Ala Cys Asp Asn Ile Asp Val Gln Asn Asn Asn Gly Asp
            20                  25                  30

Gln Ala Gly Phe Lys Val Lys Pro Glu Asp Leu Ile Cys Gly Ser Cys
        35                  40                  45

Ser Ala Leu Lys Leu Gly Ala Gly Val Thr Asp Cys Lys Lys His Gly
    50                  55                  60

Lys Asp Phe Ile Glu Phe Lys Cys Arg Tyr Cys Cys Thr Val Ala Leu
65                  70                  75                  80

Trp Phe Cys Phe Gly Thr Thr His Phe Cys Glu Pro Cys His Gln Val
                85                  90                  95

Ala Asn Asp Ser Arg Lys Lys Glu Cys Pro Gly Ile Glu Gln Cys Pro
            100                 105                 110

Leu Lys Ile Asp His Pro Pro Thr Gly Ala Glu Tyr Ala Leu Gly Cys
        115                 120                 125

Gly Leu Cys Arg Asn Asn
    130


<210> SEQ ID NO 116
<211> LENGTH: 134
<212> TYPE: PRT
<213> ORGANISM: Stylonychia lemnae

<400> SEQUENCE: 116

Lys Leu Ser Phe Tyr Gln Cys Phe Lys Cys Lys Ser Pro Tyr Tyr Gly
1               5                   10                  15

Gly Arg Tyr Glu Cys Gly Glu Gly Glu Glu Gln Lys Glu Asn Asn Ala
            20                  25                  30

Gly Pro Gln Arg Glu Pro Lys Pro Glu Asp Tyr Ile Cys Ser Ser Cys
        35                  40                  45

Ser Ala Leu Lys Leu Gly Ala Gly Val Thr Asp Cys Lys Lys His Gly
    50                  55                  60
```

Lys Asp Tyr Ile Glu Phe Lys Cys Arg Tyr Cys Cys Thr Val Ala Leu
65 70 75 80

Trp Phe Cys Phe Gly Thr Thr His Phe Cys Glu Pro Cys His Gln Val
85 90 95

Ala Asn Asp Ser Arg Lys Lys Glu Cys Pro Gly Leu Asp Gln Cys Pro
100 105 110

Leu Gly Val Glu His Pro Lys Thr Gly Thr Glu Phe Ala Leu Gly Cys
115 120 125

Gly Leu Cys Arg Asn Asn
130

<210> SEQ ID NO 117
<211> LENGTH: 127
<212> TYPE: PRT
<213> ORGANISM: Oxytricha trifallax

<400> SEQUENCE: 117

Arg Leu Ser Phe Tyr Gln Cys Phe Glu Cys Gln Gln Pro Tyr Tyr Gly
1 5 10 15

Gly Arg Arg Glu Cys Gly Gln Asn Glu Glu Gln Gln Asn Glu Phe Lys
20 25 30

Lys Glu Asp Leu Val Cys Gly Ser Cys Thr Ser Lys Lys Met Gly Leu
35 40 45

Gly Lys Gly Glu Cys Leu Lys His Gly Asn Asp Tyr Ile Glu Phe Lys
50 55 60

Cys Arg Tyr Cys Cys Lys Val Ala Leu Trp Phe Cys Phe Gly Thr Thr
65 70 75 80

His Phe Cys Glu Ser Cys His Gln Arg Ala Ser Asn Pro Val Val Thr
85 90 95

Gln Cys Leu Gly Met Gly Glu Cys Pro Leu Gly Ile Gly His Pro Ala
100 105 110

Asn Gly Gln Glu Phe Ala Leu Gly Cys Gly Leu Cys Lys Asn Asn
115 120 125

<210> SEQ ID NO 118
<211> LENGTH: 140
<212> TYPE: PRT
<213> ORGANISM: Oxytricha trifallax

<400> SEQUENCE: 118

His Leu Asn Tyr Tyr Glu Cys Tyr Glu Cys Lys Asp Pro Tyr Phe Gly
1 5 10 15

Gly His Lys Gln Cys Gly Ala Gly Ala Ala Asn Gln Gln Arg Glu Met
20 25 30

Lys Gln Gln Leu Glu His Lys Pro Glu Gln Leu Ile Cys Pro Lys Cys
35 40 45

Ala Ser Asn Val Leu Glu Tyr Gly Asn Thr Asn Cys Glu Lys His Lys
50 55 60

Asp Ala Tyr Ile Asp Tyr Lys Cys Arg Phe Cys Cys Ser Val Ala Leu
65 70 75 80

Phe Phe Cys Phe Gly Thr His His Phe Cys Asp Pro Cys His Arg Lys
85 90 95

Ala Trp Glu Met Arg Asn Lys Thr Glu Lys Asp Leu Asp Gln Cys Lys
100 105 110

Gly Lys Asp Glu Cys Pro Leu Lys Ile Asp His Pro Ala Asn Gly Lys
115 120 125

```
Glu Phe Ala Leu Gly Cys Gly Leu Cys Arg Glu Leu
    130                 135                 140


<210> SEQ ID NO 119
<211> LENGTH: 140
<212> TYPE: PRT
<213> ORGANISM: Stylonychia lemnae

<400> SEQUENCE: 119

His Leu Asn Tyr Tyr Glu Cys Phe Glu Cys Lys Asp Pro Tyr Phe Gly
1               5                   10                  15

Gly His Arg Gln Cys Gly Gly Ala Gly Ala Gln Ala Gln Gln Glu Met
            20                  25                  30

Lys Glu Gln Leu Gln His Lys Ala Glu Gln Leu Ile Cys Pro Lys Cys
        35                  40                  45

Val Ser Asn Ile Tyr Asp Ile Gly Asn Thr Asn Cys Gln Lys His Ala
    50                  55                  60

Asp Ala Phe Ile Asp Tyr Lys Cys Arg Phe Cys Cys Ser Leu Ala Leu
65                  70                  75                  80

Phe Phe Cys Phe Gly Thr His His Phe Cys Asp Pro Cys His Arg Lys
                85                  90                  95

Ala Trp Glu Met Arg Asn Lys Thr Glu Lys Asp Leu Asp Gln Cys Lys
            100                 105                 110

Gly Lys Asp Thr Cys Ala Leu Lys Ile Asp His Pro Pro Asn Gly Asn
        115                 120                 125

Glu Phe Ala Leu Gly Cys Ser Leu Cys Arg Glu Gln
    130                 135                 140


<210> SEQ ID NO 120
<211> LENGTH: 141
<212> TYPE: PRT
<213> ORGANISM: Reticulomyxa filosa

<400> SEQUENCE: 120

Met Tyr Val Phe Phe Gln Cys Phe Glu Cys Lys Lys Pro Tyr Phe Gly
1               5                   10                  15

Gly Ala Lys Glu Cys Arg Ala Gln Gly Asp Glu Glu Asp Asn Val Asp
            20                  25                  30

Ala Lys Glu Leu Lys Cys Asn Lys Cys Gln His Ile Glu Ser Val Asp
        35                  40                  45

Glu Cys Lys Asp His Gly Ala Asp Tyr Leu Ala Tyr Lys Cys Arg Tyr
    50                  55                  60

Cys Cys Lys Met Ser Val Phe His Cys Trp Ser Lys Val His Phe Cys
65                  70                  75                  80

Arg Glu Cys His Glu Pro Gly Val Trp Asp Lys Leu Cys Ala Ser Trp
                85                  90                  95

Asn Thr Trp Thr Val Glu Glu Gln Glu Lys Lys Ala Tyr Glu Ile Arg
            100                 105                 110

Ala Asp Ala Asp Val Cys Pro Leu His Val Lys His Pro Pro Asn Gly
        115                 120                 125

Phe Glu Phe Gly Leu Gly Cys Thr Leu Cys Ala Asp Lys
    130                 135                 140


<210> SEQ ID NO 121
<211> LENGTH: 141
<212> TYPE: PRT
<213> ORGANISM: Reticulomyxa filosa
```

<400> SEQUENCE: 121

```
Ile Tyr Ala Phe Phe Gln Cys Phe Glu Cys Lys Lys Pro Tyr Phe Gly
1               5                   10                  15

Gly Ala Lys Glu Cys Lys Ala Gln Asp Asp Asp Asp Asn Lys Ile Glu
            20                  25                  30

Lys Lys Asp Leu Ile Cys Asn Lys Cys Gln Lys Ile Glu Ser Ile Asp
        35                  40                  45

Glu Cys Lys Glu His Gly Ala Glu Tyr Leu Ala His Lys Cys Arg Tyr
    50                  55                  60

Cys Cys Thr Met Ser Val Phe His Cys Trp Gly Lys Val His Phe Cys
65                  70                  75                  80

Arg Glu Cys His Glu Pro Gly Val Trp Asp Lys Met Ser Thr Ala Trp
                85                  90                  95

Asn Asn Trp Thr Leu Glu Glu Gln Asp Lys Lys Ser Tyr Glu Val Arg
            100                 105                 110

Ala Asp Pro Glu Thr Cys Pro Leu His Val Arg His Pro Pro Asn Gly
        115                 120                 125

Phe Glu Phe Gly Leu Gly Cys Thr Leu Cys Ala Asp Lys
    130                 135                 140
```

<210> SEQ ID NO 122
<211> LENGTH: 142
<212> TYPE: PRT
<213> ORGANISM: Reticulomyxa filosa

<400> SEQUENCE: 122

```
Ile Tyr Ala Phe Phe Gln Cys Phe Gln Cys Lys Lys Pro Tyr Phe Gly
1               5                   10                  15

Gly Ala Lys Glu Cys Lys Ala Gln Asp Glu Glu Glu Asn Asn Gln Val
            20                  25                  30

Glu Lys Lys Asp Leu Ile Cys Asn Lys Cys Gln Lys Ile Glu Ser Val
        35                  40                  45

Asp Glu Cys Lys Glu His Gly Ala Asp Tyr Leu Ala Tyr Lys Cys Arg
    50                  55                  60

Tyr Cys Cys Thr Met Ser Val Phe His Cys Trp Gly Lys Val His Phe
65                  70                  75                  80

Cys Arg Glu Cys His Glu Pro Gly Val Trp Asp Lys Leu Cys Thr Ser
                85                  90                  95

Trp Asn Asn Leu Thr Leu Glu Glu Gln Glu Lys Lys Ala Tyr Glu Thr
            100                 105                 110

Arg Ala Asp Pro Asp Leu Cys Ser Leu Arg Val Arg His Pro Pro Asn
        115                 120                 125

Gly Phe Glu Phe Gly Leu Gly Cys Thr Leu Cys Ala Asp Lys
    130                 135                 140
```

<210> SEQ ID NO 123
<211> LENGTH: 133
<212> TYPE: PRT
<213> ORGANISM: Stylonychia lemnae

<400> SEQUENCE: 123

```
His Leu Asn Tyr Tyr Gln Cys Tyr Arg Cys Gln Leu Pro Tyr Phe Gly
1               5                   10                  15

Gly Leu Arg Gln Cys Asp Gln Asn Pro Asn Leu Gln Gln Asn Gln Ala
            20                  25                  30
```

```
Phe Val Gln Phe Asn Asn Asn Ala Trp Asp Leu Ile Cys Ser Lys Cys
        35                  40                  45

Lys Phe Tyr Gly Asn Gly Ile Ala Phe Cys Glu Thr Lys Gly His Gly
    50                  55                  60

Asp Ser Tyr Ile Gln Tyr Lys Cys Asn Phe Cys Cys Asn Ile Ala Ala
65                  70                  75                  80

Tyr His Cys Gly Gly Asn Asn Tyr Tyr Cys Met Gln Cys His Asp Arg
                85                  90                  95

Lys Gly Pro Val Gly Pro Lys Cys Ser Ser Lys Glu Asp Cys Pro Leu
            100                 105                 110

Gly Ile Glu His Pro Pro Asn Gly Ser Asn Phe Ala Val Gly Cys Gly
        115                 120                 125

Met Cys Arg Asp Leu
    130
```

<210> SEQ ID NO 124
<211> LENGTH: 133
<212> TYPE: PRT
<213> ORGANISM: Oxytricha trifallax

<400> SEQUENCE: 124

```
His Leu Asn Tyr Tyr Lys Cys Tyr Thr Cys His Asn Pro Phe Phe Gly
1               5                   10                  15

Gly Leu Lys Gln Cys Asp Gln Asn Pro Asn Leu Gln Gly Gly Asn Val
            20                  25                  30

Val Ile Gln Gln Asn Asn Asn His His Asp Leu Gln Cys Ser Lys Cys
        35                  40                  45

Lys Phe Phe Ser Asn Gly Ile Thr Tyr Cys Gln Val Lys Gly His Gly
    50                  55                  60

Gln Thr Tyr Ile Gln Tyr Lys Cys Asn Tyr Cys Cys Asn Ile Ala Ala
65                  70                  75                  80

Tyr His Cys Gly Gly Gln Asp Tyr Tyr Cys Met Arg Cys His Asp Gly
                85                  90                  95

Ser Gly Pro Ile Gly Pro Met Cys Ser Gly Pro Asp Asp Cys Pro Leu
            100                 105                 110

Arg Leu Glu His Pro Pro Asn Asn Lys Ser Phe Ala Val Gly Cys Gly
        115                 120                 125

Met Cys Lys Glu Leu
    130
```

<210> SEQ ID NO 125
<211> LENGTH: 133
<212> TYPE: PRT
<213> ORGANISM: Oxytricha trifallax

<400> SEQUENCE: 125

```
His Leu Asn Tyr Tyr Lys Cys Tyr Thr Cys Gln Asn Pro Phe Phe Gly
1               5                   10                  15

Gly Leu Lys Gln Cys Asp Gln Asp Pro Asn Leu Gln Gln Gln Val Asn
            20                  25                  30

Gln Ile Gln Trp Asn Gln Asn Leu Trp Asp Leu Lys Cys Pro Lys Cys
        35                  40                  45

Lys Phe Phe Gly Glu Gly Ile Ser Tyr Cys Glu Gln Lys Gly His Gly
    50                  55                  60

Ala Thr Tyr Ile Gln Tyr Lys Cys Asn Phe Cys Cys Asn Ile Ala Ala
65                  70                  75                  80
```

-continued

```
Tyr His Cys Gly Gly Ser Cys Tyr Tyr Cys Met His Cys His Asp Arg
                85                  90                  95

Lys Gly Pro Ala Gly Pro Ser Cys Ser Gly Pro Glu Asp Cys Pro Leu
            100                 105                 110

Gly Leu Glu His Pro Pro Asn Gly Lys Ala Phe Ala Val Gly Cys Gly
        115                 120                 125

Met Cys Lys Glu Leu
    130


<210> SEQ ID NO 126
<211> LENGTH: 126
<212> TYPE: PRT
<213> ORGANISM: Paramecium tetraurelia

<400> SEQUENCE: 126

Lys Phe Cys Phe Tyr Glu Cys Phe Lys Cys Lys Lys Pro Tyr Phe Gly
1               5                   10                  15

Gly Met Lys Asn Cys Gln Ala Ala Ala Glu Asn Asn Asp Arg Ala Gln
            20                  25                  30

Phe Asn Lys Glu Asp Leu Ile Cys Ser Ser Cys Cys Pro Ile Ser Phe
        35                  40                  45

Glu Ala Lys Cys Asn Lys His Gly Val Lys Tyr Ile Glu Phe Lys Cys
    50                  55                  60

Arg Phe Cys Cys Ser Val Ala Val Trp Phe Cys Gly Gly Thr Thr His
65                  70                  75                  80

Tyr Cys Glu Pro Cys His Ser Gly Arg Asn Pro Asn Met Asn Lys Pro
                85                  90                  95

Cys Pro Gly Gln Glu Lys Cys Pro Leu Gly Val Asn His Lys Pro Thr
            100                 105                 110

Gly Gln Glu Asn Ala Leu Gly Cys Ala Leu Cys Arg Ser Gln
        115                 120                 125


<210> SEQ ID NO 127
<211> LENGTH: 127
<212> TYPE: PRT
<213> ORGANISM: Paramecium tetraurelia

<400> SEQUENCE: 127

Ile Tyr Cys Tyr Tyr Leu Cys Phe Lys Cys Lys Lys Pro Tyr Phe Gly
1               5                   10                  15

Gly Leu Lys Asn Cys Gln Gln Ala Ala Asp Gln Asp Pro Lys Val Glu
            20                  25                  30

Phe Lys Gln Glu Asp Leu Val Cys Thr Lys Cys Cys Pro Leu Leu Thr
        35                  40                  45

Leu Glu Asp Lys Cys Lys Lys His Gly Val Asp Phe Ile Asp Phe Lys
    50                  55                  60

Cys Arg His Cys Cys Ser Ile Ala Leu Trp Trp Cys His Gly Thr Thr
65                  70                  75                  80

His Tyr Cys Asp Pro Cys His Arg Asn Ile Lys Thr Asn Met Thr Lys
                85                  90                  95

Pro Cys Pro Gly Pro Gly Lys Cys Pro Leu Gly Ile Pro His Lys Pro
            100                 105                 110

Asn Gly Gln Glu Met Ser Leu Gly Cys Ser Leu Cys Arg Ala Glu
        115                 120                 125


<210> SEQ ID NO 128
<211> LENGTH: 128
```

<212> TYPE: PRT
<213> ORGANISM: Vitrella brassicaformis

<400> SEQUENCE: 128

```
Lys Tyr Ala Phe Tyr Lys Cys Ser Lys Cys Arg Arg Val Tyr Cys Gly
1               5                   10                  15

Gly Arg Leu Asp Cys Glu Arg Asp Leu Arg Gln Glu Glu Asp Gly Ala
            20                  25                  30

Gly Gly Val Arg Pro Asn Lys Lys Asp Glu Leu Val Cys Pro Ala Cys
        35                  40                  45

Ala Ile Gly Gln Ala Gly Gln Cys Pro Lys His Gly His Gly Phe Val
    50                  55                  60

Glu Phe Lys Cys Arg Tyr Cys Cys Glu Pro Ala Val Trp Phe Cys Phe
65                  70                  75                  80

Gly Thr Thr His Phe Cys Asp Lys Cys His Asn Thr Asn Arg Ile Gly
                85                  90                  95

Lys Pro Cys Pro Gly Pro His Lys Cys Ala Leu Gly Gly Asn His Pro
            100                 105                 110

Pro Asn Pro Cys Glu Met Pro Ile Gly Cys Ala Leu Cys Lys Glu Glu
        115                 120                 125
```

<210> SEQ ID NO 129
<211> LENGTH: 149
<212> TYPE: PRT
<213> ORGANISM: Chromera velia

<400> SEQUENCE: 129

```
Val Tyr Ala Tyr Tyr Leu Cys His Arg Cys Asn Glu Pro Tyr Trp Gly
1               5                   10                  15

Gly Lys Lys Glu Cys Glu Ala Ala Gly Ala Pro Asp Pro Pro Asp Ala
            20                  25                  30

Ala Arg Arg Gly Val Lys Glu Asp Asp Arg Leu Leu Cys Pro Ala Cys
        35                  40                  45

Val Ser Ile Val Thr Gly Val Pro Ser Asn Glu Cys Ser Ile His Gly
    50                  55                  60

Thr Lys Tyr Met Asn Phe Lys Cys Lys Tyr Cys Cys Gly Thr Gly Ala
65                  70                  75                  80

Trp Phe Cys Phe Gly His Thr His Phe Cys Asp Pro Cys His Lys Arg
                85                  90                  95

Val Met Thr Glu Gly Ser Gly Ala Tyr Gln Thr Leu Val Lys Gln Cys
            100                 105                 110

Pro Gly Asp Ser Ser Gly Arg Val Val Asp Val Thr Lys Cys Pro Leu
        115                 120                 125

Gly Ile Pro His Gly Lys Asn Pro Cys Glu Arg Ser Leu Gly Cys Thr
    130                 135                 140

Leu Cys Leu Ala Ala
145
```

<210> SEQ ID NO 130
<211> LENGTH: 122
<212> TYPE: PRT
<213> ORGANISM: Trypanosoma equiperdum

<400> SEQUENCE: 130

```
Asp Leu Tyr Tyr Tyr Val Cys Cys Arg Cys Glu Lys Pro Tyr Tyr Gly
1               5                   10                  15

Gly Asn Arg Trp Cys Ser Arg Thr Ile Ser Gly Glu Pro Cys Lys Lys
```

```
            20                  25                  30

Pro Ser Glu Leu Ile Cys Ser Asp Cys Asn Asp Asp Phe Leu Cys Pro
        35                  40                  45

Ser His Asn His Asp Phe Val Leu Tyr Lys Cys Arg Tyr Cys Cys Asn
    50                  55                  60

Pro Ala Thr His Leu Ser Phe Gly Asn Arg Tyr Met Cys Asp Ala Cys
65                  70                  75                  80

Asn Lys Lys Trp Glu Gly Thr Glu Pro Glu Pro Met Glu Cys Pro Gly
                85                  90                  95

Ala Glu Lys Cys Pro Leu Gly Gly Ala His Pro Thr Gly Gly Ser Gln
            100                 105                 110

Pro Leu Gly Cys Met Leu Cys Thr Leu Phe
        115                 120


<210> SEQ ID NO 131
<211> LENGTH: 122
<212> TYPE: PRT
<213> ORGANISM: Trypanosoma congolense

<400> SEQUENCE: 131

Asp Leu Tyr Tyr Tyr Val Cys Ser Arg Cys Glu Lys Pro Phe Tyr Gly
1               5                   10                  15

Gly Asn Arg Trp Cys Ser Arg Ser Ile Ser Gly Glu Pro Ser Lys Lys
            20                  25                  30

Pro Asn Glu Leu Ile Cys Ser Asp Cys Asn Asp Asp Phe Leu Cys Pro
        35                  40                  45

Thr His Lys His Gln Phe Val Leu Tyr Lys Cys Arg Tyr Cys Cys Asn
    50                  55                  60

Pro Ala Thr His Leu Ser Phe Gly Asn Arg Tyr Met Cys Glu Asp Cys
65                  70                  75                  80

Asn Lys Lys Trp Glu Gly Ser Glu Pro Glu Arg Ala Glu Cys Pro Gly
                85                  90                  95

Ala Asp Lys Cys Pro Leu Ala Gly Asp His Pro Thr Gly Gly Ser Gln
            100                 105                 110

Pro Leu Gly Cys Met Leu Cys Leu Pro Cys
        115                 120


<210> SEQ ID NO 132
<211> LENGTH: 122
<212> TYPE: PRT
<213> ORGANISM: Trypanosoma cruzi marinkellei

<400> SEQUENCE: 132

Glu Leu Leu Tyr Tyr Ile Cys Cys Arg Cys Glu Asn Pro Phe Tyr Gly
1               5                   10                  15

Gly Glu Arg Arg Cys Phe Arg Ser Asn Asn Val Glu Pro Val Lys Lys
            20                  25                  30

Pro Cys Glu Leu Ile Cys Ser Glu Cys Asn Asp Asp Phe Leu Cys Pro
        35                  40                  45

Tyr His Lys His Asn Tyr Val Leu Tyr Lys Cys Arg Tyr Cys Cys Asn
    50                  55                  60

Pro Ala Thr His Leu Ser Phe Gly Asn Arg Tyr Leu Cys Asn Arg Cys
65                  70                  75                  80

Asp Glu Arg Trp Glu Thr Thr Glu Pro Glu Pro Ile Ala Cys Pro Gly
                85                  90                  95

Pro Ser Glu Cys Pro Leu Lys Gly Ala His Ser Thr Asp Gly Ser Ile
```

```
            100                 105                 110

Pro Leu Gly Cys Met Ile Cys Ala Ser Phe
        115                 120


<210> SEQ ID NO 133
<211> LENGTH: 122
<212> TYPE: PRT
<213> ORGANISM: Trypanosoma rangeli

<400> SEQUENCE: 133

Asp Leu Leu Tyr Tyr Ile Cys Cys Arg Cys Gly Lys Pro Phe Tyr Gly
1               5                   10                  15

Gly Glu Arg Arg Cys Phe Arg Ser Asn Asn Ala Glu Pro Ala Lys Lys
            20                  25                  30

Pro Ser Glu Leu Ile Cys Ser Asp Cys Asn Asp Asp Phe Leu Cys Pro
        35                  40                  45

Asn His Lys His Lys Tyr Val Leu Tyr Lys Cys Arg Tyr Cys Cys Asn
    50                  55                  60

Pro Ala Thr His Leu Ser Phe Gly Asn Arg Tyr Leu Cys Asn Arg Cys
65                  70                  75                  80

Asp Lys Arg Trp Glu Thr Thr Glu Pro Gly Leu Ile Pro Cys Pro Gly
                85                  90                  95

Pro Gly Glu Cys Pro Leu Gln Glu Ser His Ser Ala Asp Gly Ser Ile
            100                 105                 110

Ala Leu Gly Cys Met Met Cys Thr Ser Phe
        115                 120


<210> SEQ ID NO 134
<211> LENGTH: 121
<212> TYPE: PRT
<213> ORGANISM: Angomonas deanei

<400> SEQUENCE: 134

Asp Leu Leu Phe Tyr Ile Cys Asn Lys Cys Gly Glu Pro Phe Tyr Gly
1               5                   10                  15

Gly Glu Lys Ile Cys Phe Arg Met Leu Ser Ser Glu Pro Leu Lys Arg
            20                  25                  30

Lys Glu Asp Val Leu Cys Asp Ala Cys Val Met Asp Phe Lys Cys Lys
        35                  40                  45

Lys His Cys Arg Asn Phe Val Leu Tyr Lys Cys Gln Tyr Cys Cys Asn
    50                  55                  60

Pro Ala Thr His Arg Ser Phe Ala Thr Arg Tyr Met Cys Asp Ala Cys
65                  70                  75                  80

Glu Lys Arg Trp Glu Lys Ser Glu Pro Asp Glu Ile Pro Cys Pro Gly
                85                  90                  95

Ala Ser Lys Cys Pro Leu Gly Gly Asn His Glu Asn Gly Ser Phe Pro
            100                 105                 110

Ile Gly Cys Ala Leu Cys Leu Pro Thr
        115                 120


<210> SEQ ID NO 135
<211> LENGTH: 123
<212> TYPE: PRT
<213> ORGANISM: Phytomonas sp. isolate Hart1

<400> SEQUENCE: 135

Asp Leu Leu Phe Tyr Val Cys Ser Lys Cys Ala Glu Pro Phe Leu Gly
1               5                   10                  15
```

```
Gly Glu Asn Ser Cys Phe Arg Met Gln Gly Gly Glu Pro Ala Lys Asp
            20                  25                  30

Pro Asn Ser Leu Leu Cys Asp Asn Cys Gln Thr Asp Phe Phe Cys Pro
        35                  40                  45

Thr His Gly Arg Lys Tyr Val Ile Tyr Lys Cys Thr Tyr Cys Cys Asn
    50                  55                  60

Pro Ala Thr His Arg Ser Phe Ala Thr Arg Tyr Leu Cys Asp Arg Cys
65                  70                  75                  80

Glu Glu Arg Trp Val Gly Ser Thr Glu Val Asp Lys Ile Ser Cys Pro
                85                  90                  95

Gly Pro Asn Val Cys Pro Leu Gly Gly His His Asp Thr Thr Cys Ala
            100                 105                 110

Tyr Pro Val Gly Cys Leu Leu Cys Leu Pro Glu
        115                 120


<210> SEQ ID NO 136
<211> LENGTH: 123
<212> TYPE: PRT
<213> ORGANISM: Phytomonas sp. isolate EM1

<400> SEQUENCE: 136

Asp Leu Leu Phe Tyr Ile Cys Ser Lys Cys Ser Asn Pro Phe Leu Gly
1               5                   10                  15

Gly Glu Asn Ile Cys Phe Arg Met Gln Gly Gly Glu Pro Ala Lys Asp
            20                  25                  30

Pro Ser Ser Leu Leu Cys Glu Asn Cys Lys Thr Asp Phe His Cys Ser
        35                  40                  45

Lys His Asp Arg Glu Tyr Val Ile Tyr Lys Cys Ser Tyr Cys Cys Asn
    50                  55                  60

Pro Ala Thr His Arg Ser Phe Ala Thr Arg Tyr Leu Cys Asp Arg Cys
65                  70                  75                  80

Asp Glu Arg Trp Thr Gly Ser Ile Glu Val Glu Lys Ile Pro Cys Pro
                85                  90                  95

Gly Pro Asn Ala Cys Pro Leu Gly Gly His His Asn Thr Thr Cys Thr
            100                 105                 110

Tyr Pro Ile Gly Cys Phe Leu Cys Leu Pro Glu
        115                 120


<210> SEQ ID NO 137
<211> LENGTH: 121
<212> TYPE: PRT
<213> ORGANISM: Leptomonas pyrrhocoris

<400> SEQUENCE: 137

Asp Leu Leu Phe Tyr Ile Cys Gly Lys Cys Gly Lys Ala Phe Tyr Gly
1               5                   10                  15

Gly Glu Arg Val Cys Ser Arg Met Gln Gly Arg Ala Pro Ser Ser Ser
            20                  25                  30

Pro Asp Asp Leu Ile Cys Asp Ala Cys Leu Ala Asp Ala His Asp Gly
        35                  40                  45

Cys Asn Thr Phe Ala Pro Val Phe Lys Cys Arg Tyr Cys Cys Asn Pro
    50                  55                  60

Ala Thr Gln Arg Ser Phe Gly Thr Arg Tyr Met Cys Asp Arg Cys Asn
65                  70                  75                  80

Ala Arg Trp Asp Thr Ser Glu Pro Ser Pro Ile Pro Cys Pro Gly Ser
                85                  90                  95
```

```
Gly Glu Cys Pro Phe Asp Gly His His Glu Glu Asp Lys Gly Gly Tyr
            100                 105                 110

Ala Gly Cys Leu Leu Cys Thr Gly Ala
        115                 120


<210> SEQ ID NO 138
<211> LENGTH: 121
<212> TYPE: PRT
<213> ORGANISM: Leptomonas seymouri

<400> SEQUENCE: 138

Asp Leu Leu Tyr Tyr Ile Cys Ala Lys Cys Gly Gly Ala Phe Tyr Gly
1               5                   10                  15

Gly Glu Arg Val Cys Pro Arg Met Gln Gly Gly Glu Pro Ser Ser Ser
            20                  25                  30

Pro Asp Asp Leu Ile Cys Asp Thr Cys Leu Ala Gly Ala His Glu Gly
        35                  40                  45

Cys Asp Thr Phe Ala Pro Val Phe Lys Cys Arg Tyr Cys Cys Asn Pro
    50                  55                  60

Ala Thr Gln Arg Ser Phe Gly Thr Arg Tyr Met Cys Asp Arg Cys Ser
65                  70                  75                  80

Ala Arg Trp Gly Thr Ser Glu Pro Ala Pro Ile Pro Cys Pro Gly Ser
                85                  90                  95

Gly Gly Cys Pro Phe Asp Gly His His Glu Gly Gly Lys Cys Gly Phe
            100                 105                 110

Ala Gly Cys Leu Leu Cys Ser Cys Ala
        115                 120


<210> SEQ ID NO 139
<211> LENGTH: 121
<212> TYPE: PRT
<213> ORGANISM: Leishmania infantum

<400> SEQUENCE: 139

Glu Phe Leu Phe Tyr Leu Cys Gly Arg Cys Gly Gly Ala Phe Tyr Gly
1               5                   10                  15

Gly Asp Gln Val Cys Ser Arg Met Gln Gly His Glu Pro Ser Ser Ser
            20                  25                  30

Pro Gln Glu Leu Ile Cys Asp Thr Cys Leu Arg Lys Asp His Arg Thr
        35                  40                  45

Cys Asp Thr Leu Thr Ala Val Phe Lys Cys Arg Tyr Cys Cys Asn Pro
    50                  55                  60

Ala Thr Gln Arg Ser Phe Gly Thr Arg Phe Met Cys Asp Arg Cys Ile
65                  70                  75                  80

Ala Arg Trp Asp Thr Ala Glu Pro Ala Leu Ile Pro Cys Pro Gly Ala
                85                  90                  95

Asp Ser Cys Pro Phe His Gly Asn His Pro Glu Pro Ala Cys Asp Ile
            100                 105                 110

Ala Ala Cys Leu Thr Cys Leu Asp Pro
        115                 120


<210> SEQ ID NO 140
<211> LENGTH: 121
<212> TYPE: PRT
<213> ORGANISM: Leishmania mexicana

<400> SEQUENCE: 140
```

```
Lys Phe Leu Phe Tyr Leu Cys Gly Arg Cys Gly Gly Val Phe Tyr Gly
1               5                   10                  15

Gly Asp Glu Val Cys Ser Arg Met Gln Gly Arg Glu Pro Ser Ser Ser
            20                  25                  30

Pro Gln Glu Leu Val Cys Asp Thr Cys Leu Ala Lys Gly His Arg Thr
        35                  40                  45

Cys Asp Thr Leu Thr Ala Val Phe Lys Cys Arg Tyr Cys Cys Asn Pro
    50                  55                  60

Ala Thr Gln Arg Ser Phe Gly Thr Arg Phe Ala Cys Asp Arg Cys Ile
65                  70                  75                  80

Ala Arg Trp Asp Asn Ala Glu Pro Ala Phe Ile Pro Cys Pro Gly Ala
                85                  90                  95

Asp Ser Cys Pro Phe Asp Gly Asn His Pro Glu Pro Ala Cys Asp Ile
            100                 105                 110

Ala Ala Cys Leu Thr Cys Leu Asp Pro
        115                 120


<210> SEQ ID NO 141
<211> LENGTH: 121
<212> TYPE: PRT
<213> ORGANISM: Leishmania panamensis

<400> SEQUENCE: 141

Asp Leu Leu Phe Tyr Ile Cys Gly Arg Cys Arg Asn Ala Phe Tyr Gly
1               5                   10                  15

Gly Leu Arg Met Cys Ser Arg Met Gln Gly Arg Glu Pro Ser Ser Pro
            20                  25                  30

Pro Gln Asp Leu Val Cys Asp Thr Cys Leu Thr Lys Gly His Lys Thr
        35                  40                  45

Cys Ser Thr Leu Thr Ala Val Phe Lys Cys Arg Tyr Cys Cys Asn Pro
    50                  55                  60

Ala Thr Gln Arg Ser Phe Gly Thr Arg Phe Thr Cys Asp Arg Cys Ile
65                  70                  75                  80

Ala Arg Trp Asp Thr Ala Glu Pro Ala Leu Ile Pro Cys Ser Gly Ala
                85                  90                  95

Asp Asn Cys Pro Phe Asp Gly Asn His Pro Cys Pro Pro Cys Asn Ile
            100                 105                 110

Ala Gly Cys Leu Thr Cys Leu Asp Pro
        115                 120


<210> SEQ ID NO 142
<211> LENGTH: 140
<212> TYPE: PRT
<213> ORGANISM: Thalassiosira pseudonana

<400> SEQUENCE: 142

Ser Tyr Ala Phe Tyr Leu Cys Gly Ala Cys Asp Glu Pro Phe Phe Gly
1               5                   10                  15

Gly Thr Ile Glu Cys Ala Asp Gln Asp Glu Gly Glu Leu Gln Thr Ala
            20                  25                  30

Asp Asp Arg Ile Cys Asn Val Cys Ser Pro Lys Thr Gln Thr Ile Cys
        35                  40                  45

Gln Lys Ala Tyr Glu His Gly Ala Phe His Val Trp Lys Cys Arg Tyr
    50                  55                  60

Cys Cys Asn Pro Ser Thr Phe Val Cys Tyr Gly Asn Val His Phe Cys
65                  70                  75                  80
```

-continued

```
Lys Ser Cys His Asp Arg Asn Ser Glu Arg Asp Ala Arg Arg Ser Val
                85                  90                  95

Pro Val Leu Glu Gly Ile Pro Cys Val Gly Glu Ser Cys Thr Tyr Pro
            100                 105                 110

Lys Pro Asn Gly Cys Asn Lys His Ala Asn Gly Pro Ser Arg Asp Cys
        115                 120                 125

Glu Gln Val Tyr Tyr Cys Val Cys Cys Leu Ala Thr
    130                 135                 140


<210> SEQ ID NO 143
<211> LENGTH: 149
<212> TYPE: PRT
<213> ORGANISM: Fragilariopsis cylindrus

<400> SEQUENCE: 143

Lys Tyr Ala Phe Tyr Leu Cys Ser His Cys Glu Glu Pro Tyr Phe Gly
1               5                   10                  15

Gly Thr Ile Arg Cys Ala Asp Glu Asn Pro Leu Pro Thr Thr Pro Asp
            20                  25                  30

Gln Tyr Gln Gln Gln Ile Pro Val Glu Lys Arg Leu Cys Pro Gly Cys
        35                  40                  45

Thr Pro Glu Thr Gln Leu Val Cys Gln Asn Pro Ile Glu His Gly Arg
    50                  55                  60

Tyr Leu Leu Trp Lys Cys Arg Tyr Cys Cys Lys Pro Ser Thr His Val
65                  70                  75                  80

Cys Tyr Gly Gln Val His Phe Cys Gln Asp Cys His Asp Lys Asn Ser
                85                  90                  95

Gln Arg Val Ala Thr Ala Pro Lys Pro Pro Ser Ser Ser Leu Ser Phe
            100                 105                 110

Ser Ser Thr Thr Ala Ala Thr Thr Thr Thr Thr Asp Arg Cys Lys Phe
        115                 120                 125

His Ser Asn Gly Pro Thr Lys Asp Cys Glu Gln Val Tyr Ser Cys Ala
    130                 135                 140

Ile Cys Asp Ser Val
145
```